US007875428B2

(12) United States Patent
Pourmand et al.

(10) Patent No.: US 7,875,428 B2
(45) Date of Patent: Jan. 25, 2011

(54) MULTIPLEXED ASSAY AND PROBES FOR IDENTIFICATION OF HPV TYPES

(75) Inventors: Nader Pourmand, San Mateo, CA (US); Baback Gharizadeh, Palo Alto, CA (US); Ronald W. Davis, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 670 days.

(21) Appl. No.: 11/707,832

(22) Filed: Feb. 13, 2007

(65) Prior Publication Data

US 2007/0207456 A1 Sep. 6, 2007

Related U.S. Application Data

(60) Provisional application No. 60/773,601, filed on Feb. 14, 2006.

(51) Int. Cl.
*C12Q 1/68* (2006.01)
*C12P 19/34* (2006.01)
*C12M 3/00* (2006.01)
*C07H 21/04* (2006.01)

(52) U.S. Cl. .................. 435/6; 435/91.2; 435/287.2; 536/24.3

(58) Field of Classification Search .................. None
See application file for complete search history.

(56) References Cited

U.S. PATENT DOCUMENTS

2002/0110828 A1* 8/2002 Ferea et al. .................. 435/6
2004/0175719 A1* 9/2004 Christians .................... 435/6
2008/0287318 A1* 11/2008 Kranewitter et al. ........ 506/17

FOREIGN PATENT DOCUMENTS

WO WO 2005/056839 * 6/2005

OTHER PUBLICATIONS

GenBank record having accession No. U3174 GI: 1020219, dated Oct. 17, 1995, eight pages.*
Baback Gharizadeh, et al., "Viral and microbial genotyping by a combination of multiplex competitive hybridization and specific extension followed by hybridization to generic tag arrays," *Nucleic Acids Research*, 2003, vol. 31, No. 22 e146.

(Continued)

*Primary Examiner*—Juliet C Switzer
(74) *Attorney, Agent, or Firm*—David J. Aston; Peters Verny, LLP

(57) ABSTRACT

A DNA microarray, preferably in the form of a chip, contains probes which hybridize to generate primers capable of amplifying approximately 89 HPV types. These target the E1 region of the gene. The design of the chip allows for the detection of any known HPV type, based on a unique probe sequence derived from the HPV E1 region. The present assay utilizes a number of primers that can amplify from about one to six different types of HPV. A large number of primers can be used together. After amplification, the amplicons are contacted with specific probes that are unique for each HPV type. The array further employs a control sequence, which normalizes variability due to sample size.

11 Claims, 3 Drawing Sheets

OTHER PUBLICATIONS

Girish Nallur, et al., "Signal amplification by rolling circle amplification on DNA microarrays," *Nucleic Acids Research*, 2001, vol. 29, No. 23 e118.

David J. Duggan, et al., "Expression profiling using cDNA microarrays," *Nature Genetics Supplement*, Jan. 1999, vol. 21, 10-14.

P.E. Gravitt, et al., "Genotyping of 27 Human Papillomavirus Types by Using L1 Consensus PCR Products by a Single-Hybridization, Reverse Line Blot Detection Method," *Journal of Clinical Microbiology*, Oct. 1998, vol. 36, No. 10., 3020-3027.

Brooks E. Miner, et al., "Molecular barcodes detect redundancy and contamination in hairpin-bisulfite PCR," *Nucleic Acids Research*, Sep. 30, 2004, vol. 32, No. 17 e135.

* cited by examiner

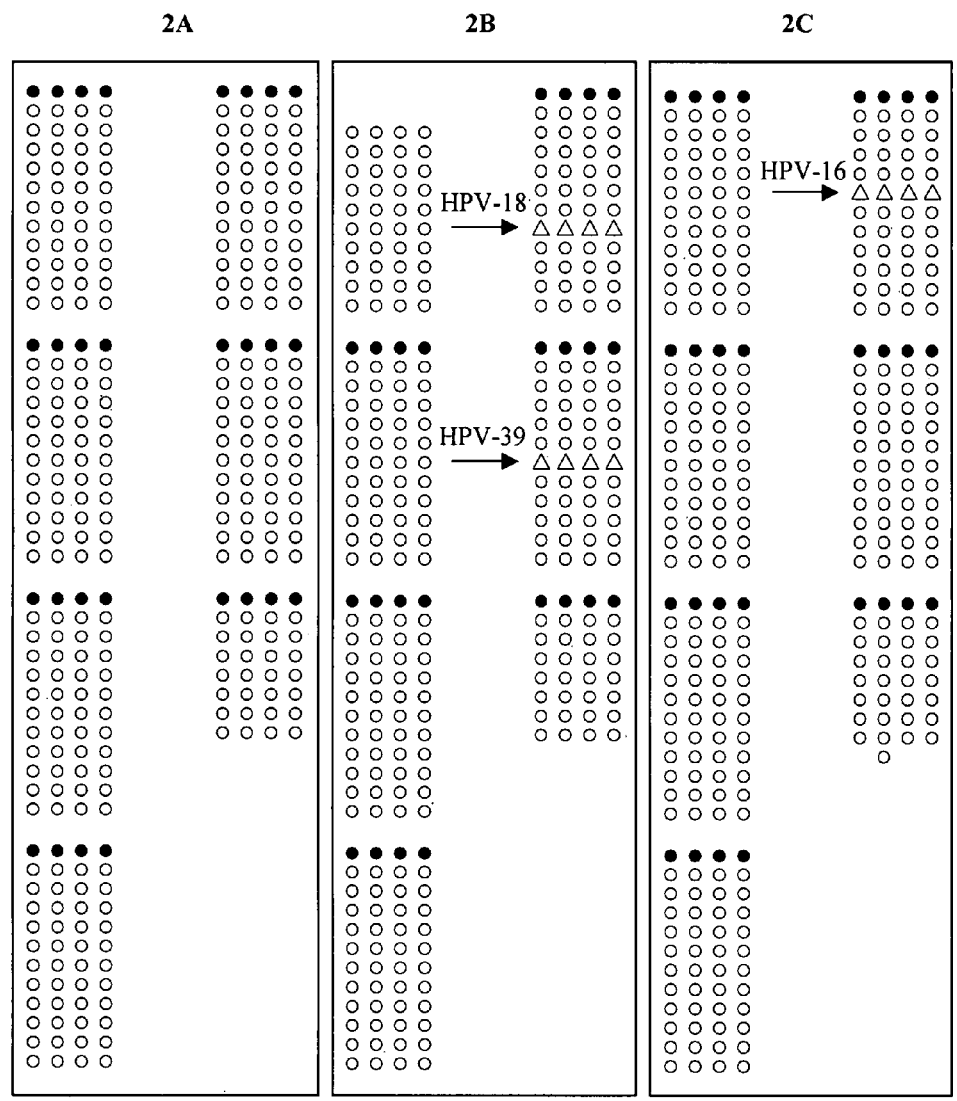
Fig. 2A-C

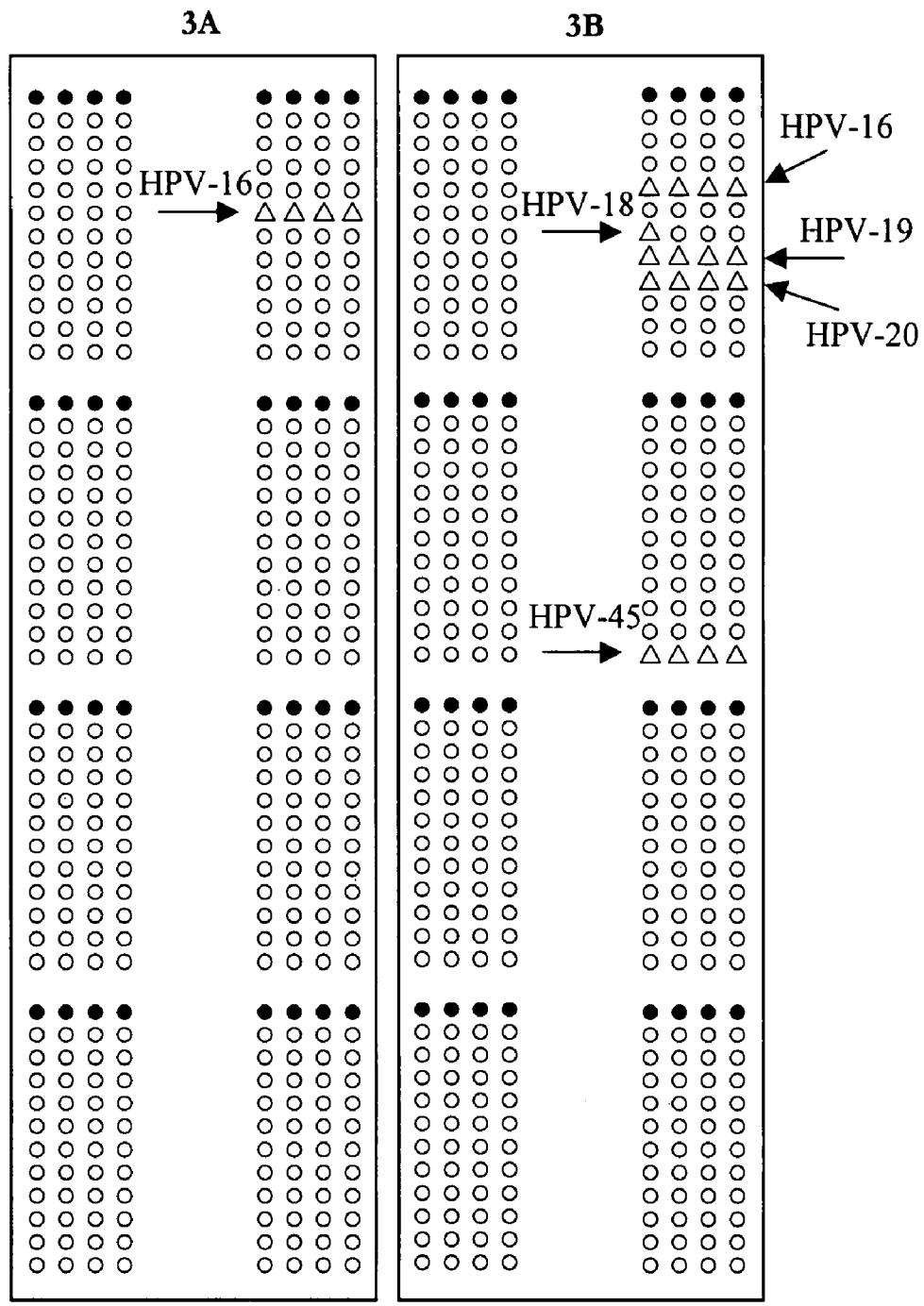
Fig. 3A-B

```
SEQUENCE LISTING

<160> NUMBER OF SEQ ID NOS: 310

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtccmarrg gawactgatc                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcmcagggwc ataayaatgg                                                     20

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
```

```
             primer
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (26)..(26)
<223> OTHER INFORMATION: Inosine
<220> FEATURE:
<221> NAME/KEY: modified_base
<222> LOCATION: (28)..(29)
<223> OTHER INFORMATION: Inosine
<220> FEATURE:
<221> NAME/KEY: modified_base
<222> LOCATION: (33)..(33)
<223> OTHER INFORMATION: Inosine

<400> SEQUENCE: 3 gncagggnc ataanaatgg cgtccnanng ganactgatc                    40

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtaaacgtt ttccctattt ttt                                    23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taccctaaat actctgtatt g                                      21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taccctaaat accctatatt g                                      21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```
tttgttactg tggtagatac                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaaaaataaa ctgtaaatca                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
btcaaatgcc cattgcacca t                                             21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caccagagtg gatagttagg c                                             21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
btcaaatgcc cactgaatca t                                             21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caccagagtg gatagtcagg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
btcatatgcc cactgcacca                                                    20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccagagtg gatagtgaga c                                                  21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
btcgtatgcc cactgcacc                                                     19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacctgaatg gatagtaaga c                                                  21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
bggtcatatg catactgtac cat                                                23

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctccggattg gatagtaaga c                                                  21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
btcgtatgca tactgtacca t                                                  21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
caccagaatg gattgtaaga c                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
btcatatgcg tactgcacca t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
caccagaatg gattgttaga c                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
btcatatgcc cattgcacca t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
caccagaatg gattgtgaga c                                              21

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
btccaatgcc cactgcac                                                  18

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caccagaatg gatagtaagg c                                         21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
btcaaatgcc cactgcac                                             18

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caccagactg gatagtacga c                                         21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
btcaaatgcc cattgtacca t                                         21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caccagaatg gataacacgc c                                         21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
btcatatgcc cattgtacca t                                         21

```
<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caccagaatg gataacaagg c                                             21

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
btcgaaggcc cattggacc                                                19

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caccagaatg gataaaaagg c                                             21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
btcgtaggcc cattgtacca t                                             21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacccgaatg gatacaaaga c                                             21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
btcaaaggcc cattgtacca t                                             21

<210> SEQ ID NO 38
```

```
<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cacctgagtg gatacaaaga c                                             21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
btcaaacgcc cattgaacca t                                             21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caccggaatg gatagctaaa c                                             21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
btcaaatgcc cattgtacca t                                             21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgccagaatg gatacaacga t                                             21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
btcaaatgcc cattgaacca t                                             21

<210> SEQ ID NO 44
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caccagaatg gatagtacga c                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
btgaaatgcc cattggacca t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caccagaatg gattacacga c                                              21

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
btcgaacgcc cattgcac                                                  18

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
caccagaatg gattacaaga c                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
btcatatgcc cattgcacca t                                              21

<210> SEQ ID NO 50
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 50
caccagaatg gatacaaaga c                                              21

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
btcatatgcc cactgcacc                                                 19

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caccagaatg gatagaaaga c                                              21

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
btcaaatgcc cactgcacc                                                 19

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cgccagaatg gatacaaaga c                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
btcgtatgcc cactgtacca t                                              21

<210> SEQ ID NO 56
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 56
ggtacaaccc cagaatggat                                                    20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
btcataagcc cactgaacca t                                                  21

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggtacaaccc caggatgg                                                      18

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
btcaaacgcc cattgtatca t                                                  21

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggtacaactt tggagtggat                                                    20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
btcatatgcc cactgtatca t                                                  21

<210> SEQ ID NO 62
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 62
ggacaaacac ctgattggat                                                   20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
btcataagca aattgtatca t                                                 21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggtccatatc ctgattggat                                                   20

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
btcataagcc cattgtatca t                                                 21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggaccgtttc cagattggtt                                                   20

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
batcataagc ccattgtatc att                                               23

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ggagagtatc ctgagtggat                    20

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
btcaaatgcc cactgtacca t                  21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggctcatatc cagattggat                    20

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
btcatatgcc cactgtacca t                  21

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggaacctatc ctgattggat                    20

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
btcatacgcc cactgcaca                     19

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 74
tctgagccac ttggactgag aacccttatt aatcatcagt tagat              45

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75 ttttttctg agccacttgg actgagattt tgggccataa gagtg               45

<210> SEQ ID NO 76
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76 ttttttctg agccacttgg actgaggaac agttcagact gtcag               45

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ttttctgagc cacttggact gaggtagaac atcagttagc ttcag              45

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ttttttctga gccacttgga ctgagcagtt cagtctgtca gaatg              45

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ttttctgagc cacttggact gagcaatttg acctttctga aatga              45

<210> SEQ ID NO 80
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 80
tttttttctg agccacttgg actgagctgc agagactttt gagtt          45

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tttttctgag ccacttggac tgagtaaatc atcagctagc aactg          45

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ttttctgagc cacttggact gagttgccca acaaactata ttagg          45

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ttttctgagc cacttggact gagaaacgca actacaacat agttt          45

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tttttctgag ccacttggac tgagactgtt attgaacatg ggttg          45

<210> SEQ ID NO 85
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tttctgagcc acttggactg agacaatagc atattcgatt ttgga          45

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
```
tttttttctg agccacttgg actgagcagt tattgaacac gggtt         45

<210> SEQ ID NO 87
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttttctgagc cacttggact gagacagtta caacatagct ttgag         45

<210> SEQ ID NO 88
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ttttctgagc cacttggact gagagcacct tgattttc tgtaa           45

<210> SEQ ID NO 89
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tctgagccac ttggactgag tgtaattgaa tatagcttag cagac         45

<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttttctgagc cacttggact gagcactaat taatcaccaa tctgc         45

<210> SEQ ID NO 91
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tttttttctg agccacttgg actgagcttg gtgacaacca attca         45

<210> SEQ ID NO 92
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92 tttttctga gccacttgga ctgaggttta gcctttcaga gatgg            45

<210> SEQ ID NO 93
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ttctgagcca cttggactga gcagtttaca ggatagtcaa tttga            45

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ttttctgagc cacttggact gagcagaccg ttattgaaca tagtt            45

<210> SEQ ID NO 95
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tttctgagcc acttggactg agagatgagc agttcaaatt atctg            45

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96 tttttctga gccacttgga ctgagaattt tgggccatca aaatg            45

<210> SEQ ID NO 97
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97 ttttctgag ccacttggac tgagcagtgt tacagcatag cttta            45

<210> SEQ ID NO 98
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ttttctgagc cacttggact gagtggactt gcagataatc aattt            45

<210> SEQ ID NO 99
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 99 tttttctga gccacttgga ctgaggagtt gatgatagcg tgttt                    45

<210> SEQ ID NO 100
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 100 tttttctga gccacttgga ctgagcagaa gcaaatgcat ttgat                    45

<210> SEQ ID NO 101
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
tttttctgag ccacttggac tgagctatgt tagaccatga atccg                   45

<210> SEQ ID NO 102
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
ttttctgagc cacttggact gagcaatgat aaatcaccaa acagc                   45

<210> SEQ ID NO 103
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
tttttttctg agccacttgg actgagaatg caagaagcac agttt                   45

<210> SEQ ID NO 104
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
tctgagccac ttggactgag gattgtacat ttgaattatc acaga                   45

<210> SEQ ID NO 105
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tttctgagcc acttggactg agcattgttg aatcatcaat tagca            45

<210> SEQ ID NO 106
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ttctgagcca cttggactga gctatgatta atcatcaaac agcac            45

<210> SEQ ID NO 107
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tttttctgag ccacttggac tgagaaacct tagtaagcca tcaag            45

<210> SEQ ID NO 108
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tctgagccac ttggactgag ggaatagatg atagcaattt tgatt            45

<210> SEQ ID NO 109
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ttctgagcca cttggactga gcagtttaca agacaatcaa tttga            45

<210> SEQ ID NO 110
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ttttctgagc cacttggact gagaagcaag tagttttgat tgtc             45

<210> SEQ ID NO 111
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
tttttctgag ccacttggac tgagggtact gcaacatagt tttga                45

<210> SEQ ID NO 112
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 112 tttttttctga gccacttgga ctgagctatt gttggtcatc agagc                45

<210> SEQ ID NO 113
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
tctgagccac ttggactgag cacaattaga acatagtttt gaaga                45

<210> SEQ ID NO 114
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 114 ttttttctg agccacttgg actgaggaag ccagtgcatt tgata                45

<210> SEQ ID NO 115
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
tttctgagcc acttggactg agaacagtaa tacagcatgg aatag                45

<210> SEQ ID NO 116
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 116 tttttctga gccacttgga ctgagtgtac aatttgacct gtctg                45

<210> SEQ ID NO 117

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 117 tttttttct gagccacttg gactgagaaa ctgtggtagg acaca        45

<210> SEQ ID NO 118
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
ttctgagcca cttggactga gatacaattt gatttgtctc gtatg        45

<210> SEQ ID NO 119
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
tttttctgag ccacttggac tgaggacaca gtttagcctt tctac        45

<210> SEQ ID NO 120
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
tctgagccac ttggactgag tggattatag aacaaacact gatag        45

<210> SEQ ID NO 121
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
tttttctgag ccacttggac tgaggttagt gcagcatagt ttaga        45

<210> SEQ ID NO 122
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
ttttctgagc cacttggact gaggctagta catttgatct atcgg        45

<210> SEQ ID NO 123
<211> LENGTH: 45

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ttttctgagc cacttggact gaggcaattt gatttgtctc aaatg           45

<210> SEQ ID NO 124
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tctgagccac ttggactgag ttgatgatgc tacatttgat ttatc           45

<210> SEQ ID NO 125
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tttctgagcc acttggactg agtgcaattt gacttatctg aaatg           45

<210> SEQ ID NO 126
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tttttctgag ccacttggac tgagtagtat ggaagatgag cagtt           45

<210> SEQ ID NO 127
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tttttttctg agccacttgg actgagattg tgggacatgc tttag           45

<210> SEQ ID NO 128
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tttttttcct gagccacttg gactgaggca cagtttagtc tgtcg           45

<210> SEQ ID NO 129
<211> LENGTH: 45
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 129
ttttctgagc cacttggact gagacaatga taagccatca tacag            45

<210> SEQ ID NO 130
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tttttttctg agccacttgg actgaggtag gtcacgcatt acaag            45

<210> SEQ ID NO 131
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tttttttctg agccacttgg actgagtgca ggaaacacag tttag            45

<210> SEQ ID NO 132
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tttttttctg agccacttgg actgaggttt tcaggactgc caatt            45

<210> SEQ ID NO 133
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ttttctgagc cacttggact gagttttgat gatagcacgt ttgaa            45

<210> SEQ ID NO 134
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134 tttttttctga gccacttgga ctgagcacaa catttgattt gtccc            45

<210> SEQ ID NO 135
<211> LENGTH: 45
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 135
tttctgagcc acttggactg agagaagccc aatttagttt atcaa              45

<210> SEQ ID NO 136
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tttttttctg agccacttgg actgagttgc tttgcagata cacag              45

<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tttttttctg agccacttgg actgaggaca aactgtaatt gggca              45

<210> SEQ ID NO 138
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tctgagccac ttggactgag actgttttac aacatagctt taatg              45

<210> SEQ ID NO 139
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ttctgagcca cttggactga gcatggtata gatgacagtg tattt              45

<210> SEQ ID NO 140
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
tttttttctg agccacttgg actgaggtag tacagcacag cttag              45

<210> SEQ ID NO 141
<211> LENGTH: 45
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 141
tttttctgag ccacttggac tgagcacaat ttagcctatc tgtgt            45

<210> SEQ ID NO 142
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
tttctgagcc acttggactg agatgcaata tttgacctat ctgaa            45

<210> SEQ ID NO 143
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ttctgagcca cttggactga gacacaattt agcttatcag tactg            45

<210> SEQ ID NO 144
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tttttttctg agccacttgg actgagaata atgctgaagc aagca            45

<210> SEQ ID NO 145
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
tttttttctg agccacttgg actgagcaat gaaggaaacc cagtt            45

<210> SEQ ID NO 146
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146 tttttctga gccacttgga ctgagaccat gatcaatcac caatc            45

<210> SEQ ID NO 147
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
tttttttctg agccacttgg actgagggca cagtctagaa gaatg            45

<210> SEQ ID NO 148
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tttttctgag ccacttggac tgagcaatga tacagcatca aactg             45

<210> SEQ ID NO 149
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tttttctgag ccacttggac tgagcagtgt tagaacacag ttttg             45

<210> SEQ ID NO 150
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tctgagccac ttggactgag ctgttataca acatggaata gatga             45

<210> SEQ ID NO 151
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151 tttttctga gccacttgga ctgagcattg ctttctcatc aggaa              45

<210> SEQ ID NO 152
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tttttctgag ccacttggac tgagtatgtt agaacacagc tttgc             45

<210> SEQ ID NO 153
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 153
tttttctgag ccacttggac tgagggcaac atttgatatg tcaac              45

<210> SEQ ID NO 154
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
tttttctgag ccacttggac tgagaaacct tagtaagcca tcaag              45

<210> SEQ ID NO 155
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
tttttctgag ccacttggac tgagagttta ccctttcaga gatga              45

<210> SEQ ID NO 156
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
tttttttctg agccacttgg actgagtttt gcagatgccc aattt              45

<210> SEQ ID NO 157
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157 tttttctga gccacttgga ctgagctaag cagacaatag tgagc               45

<210> SEQ ID NO 158
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ttctgagcca cttggactga gttgcagaca accaatttaa attag              45

<210> SEQ ID NO 159
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 159 tttttctga gccacttgga ctgagcgatg attagtcacc atgag            45

<210> SEQ ID NO 160
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
tttctgagcc acttggactg agattcaaca tggtattgac gatag            45

<210> SEQ ID NO 161
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161 tttttttct gagccacttg gactgaggta cttggccacc aaaat             45

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
agagcctcca aaattgcgta                                        20

<210> SEQ ID NO 163
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgcattacta ttagtgtctg ccaat                                  25

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
aaccaccaaa attgcgaagt                                        20

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
```
gctgcattgc tgttgctg                                                        18

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ccatatgtta attgagccac ct                                                   22

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
catctgctat caatgcatac tcg                                                  23

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
attcagccac ccaaattacg                                                      20

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tcactgtcag ctaattgtgc at                                                   22

<210> SEQ ID NO 170
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
aattgaacct cctaaaatac aaagc                                                25

<210> SEQ ID NO 171
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ttggcatcta tatctgcacg tt                                          22

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
aaccaccaaa actacgaagt cc                                          22

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tccacaatcc tttacatatt ttgc                                        24

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gcatttgttg gggtaacca                                              19

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ccaaaattcc agtcctccaa                                             20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tccctctcca agtggctcta                                             20

<210> SEQ ID NO 177
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ggacataaca tctgcagtta aagtaa                                      26

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
taacaacggg cgagaaactc                                              20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
ggaaggtggc aatgtcaatc                                              20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
acgtgctcag ggacacaata                                              20

<210> SEQ ID NO 181
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
actgtgaata tatgtcatta tgtctgc                                      27

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
acgtttccca ggatctggtt                                              20

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ttccactgtt ctaaaatacc agca                                         24

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ccctcctccc agttctgtat                                              20

<210> SEQ ID NO 185
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gcagttaagg ttattttaca aagttga                                      27

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tctgagccac ttggactgag                                              20

<210> SEQ ID NO 187
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
aatgacacaa acaatga                                                 17

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
aaacagtatt acaacat                                                 17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ttactattat acaaaca                                                 17

```
<210> SEQ ID NO 190
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
agcacaacaa acaatat                                                   17

<210> SEQ ID NO 191
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gcacagcaaa ctattct                                                   17

<210> SEQ ID NO 192
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
tgcccagcaa acaattg                                                   17

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tatagacaca gagtatg                                                   17

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
aaacgatggt tggacat                                                   17

<210> SEQ ID NO 195
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
agacaaatgg taggtca                                                   17

<210> SEQ ID NO 196
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
aaacaattgt agaacatt                                                 18

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
aaacagtagt acagcaca                                                 18

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
tgcacaacag actatatt                                                 18

<210> SEQ ID NO 199
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tgacaaatta ttccaaa                                                  17

<210> SEQ ID NO 200
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
agcacacata ctgttat                                                  17

<210> SEQ ID NO 201
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gctggccaga caaactg                                                  17

<210> SEQ ID NO 202
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
agacaacaaa ttgcaaa                                                      17

<210> SEQ ID NO 203
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
taacggtact gcaacat                                                      17

<210> SEQ ID NO 204
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aaacagttgt gggcaca                                                      17

<210> SEQ ID NO 205
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tgttcagcaa acgatgat                                                     18

<210> SEQ ID NO 206
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
acgcagtaca aat                                                          13

<210> SEQ ID NO 207
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tcgcagtacc aattt                                                        15

<210> SEQ ID NO 208
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 208
acgcagtaca aata                                                         14

<210> SEQ ID NO 209
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
acgcagtaca aata                                                         14

<210> SEQ ID NO 210
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tcgcagtacc aattt                                                        15

<210> SEQ ID NO 211
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
acgcagtaca aata                                                         14

<210> SEQ ID NO 212
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tcgcagtacc aattt                                                        15

<210> SEQ ID NO 213
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
acgcagtaca aata                                                         14

<210> SEQ ID NO 214
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 214
acgcagtaca aata                                                              14

<210> SEQ ID NO 215
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
acgcagtaca aata                                                              14

<210> SEQ ID NO 216
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tgttgaagaa ta                                                                12

<210> SEQ ID NO 217
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
acgcagtaca aata                                                              14

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
btcatatgca tattgtacca tagt                                                   24

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
caccagaatg gatagttaga c                                                      21

<210> SEQ ID NO 220
<211> LENGTH: 91
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 220
tctcctatat ctgctgcaga agaaatagaa ctgcaccctc ttgtggctca tgcacaggat    60
agcagtggct tatttgatgt ttatgcagaa c                                   91

<210> SEQ ID NO 221
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tctcctatat ctgctgcaga agaaatagaa ctgcaccctc ttgtggctca tgcacaggat    60
agcagtggct tatttgatgt ttatgcagaa c                                   91

<210> SEQ ID NO 222
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gcaatgtcaa atattagtga ggttgatgga gaaacaccag aatggattca aagacaaaca    60
gtattacagc atagttttaa tgatgcaata tttgacctat ctgaaatggt aca          113

<210> SEQ ID NO 223
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ggaatgtcaa acattagcga tgtatatggt gaaacaccag aatggataga aagacaaaca    60
gtattacagc atagttttaa tgacacaaca tttgatttgt cccaaatggt aca          113

<210> SEQ ID NO 224
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ggtatatcaa atattagtga agtgtatgga gacacgccag aatggataca aagacaaaca    60
gtattacaac atagttttaa tgattgtaca tttgaattat cacagatggt aca          113

<210> SEQ ID NO 225
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gggttgtcca atataagtga gacatatgga gatacaccag aatggatagt acgacaaaca    60
caattagaac atagttttga tgatgctaca tttgatttat caaaaatggt gca          113

<210> SEQ ID NO 226
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ggattatcaa acataagtga aacacatggg gacacaccag aatggatagt aagacaaaca    60
caattagaac atagttttga agatacaata tttgatttat caaaaatggt gca          113

<210> SEQ ID NO 227
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ggcatatcaa acattagcaa tacatatgga gagacacctg aatggattac acgacaaacg    60
caactacaac atagttttga ggatagtacc tttgaattat cacaaatggt gca          113

<210> SEQ ID NO 228
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ggaatatcaa acattagtag cacatatggc gaaacaccag aatggattac aagacaaaca    60
caactacagc acagttttga tgatagcacg tttgaactat cgcaaatggt aca          113

<210> SEQ ID NO 229
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gcaatgtcaa atattagtga tgtgtatgga gacacaccag aatggataca aagacaaaca    60
caattgcaac acagtttaca ggatagtcaa tttgaattat ctaaaatggt gca          113

<210> SEQ ID NO 230
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gcaatgtcaa atattagtga ggtgtatggg gaaacaccag aatggataca aagacagaca    60
caattgcaac acagtttaca agacaatcaa tttgaattgt ctaaaatggt aca          113

<210> SEQ ID NO 231
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gcaatgtcta atattagtga catatatggt gagacaccag aatggataca gcgacaaaca      60
caaatacagc acagttttca ggactgccaa tttgaactgt cgaaaatggt gca           113

<210> SEQ ID NO 232
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tctatatcca acattagtga cgtgtatggg agtacaccag aatggataga aagacaaaca      60
cagttacaac atagctttga ggactgtcaa tttgaactat ctaaaatggt gca           113

<210> SEQ ID NO 233
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
agcctatcaa acattagtga aacggtggga gaagtacccg aatggattaa aagacaaaca      60
gtagtacagc acagcttaga ggactgtcaa tttgacctat ctcaaatggt aca           113

<210> SEQ ID NO 234
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
agtttatcaa atattagtga aatagtagga gacacacctg agtggattaa aagacaaacg      60
ttagtgcagc atagtttaga tgatagtcaa tttgacctat ctcaaatgat aca           113

<210> SEQ ID NO 235
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gcaatgtcaa acattagtga tgtacaaggt acaacacctg aatggataga tagactaact      60
gttttacaac atagctttaa tgataatata tttgatttaa gtgaaatggt aca           113

<210> SEQ ID NO 236
<211> LENGTH: 113

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gcaatgtcaa atataagtga tgtgcaaggg acaacaccag aatggataga tagattaaca    60
gtgttacagc atagctttaa tgatgatata tttgatttaa gtgaaatgat aca           113

<210> SEQ ID NO 237
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ggaatgtcaa atataagtga agtaagtggg caaacaccag aatggataga aagactaacg    60
gtactgcaac atagttttga tgatactata tttgatttag gagaaatggt gca           113

<210> SEQ ID NO 238
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ggtttgtcta atattagtga ggtatatggt accaccccag aatggataga acaacaaaca    60
gtattacagc atagctttga caatagcata ttcgattttg gagaaatggt gca           113

<210> SEQ ID NO 239
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ggaatatcaa atattagtga agtaatggga gacacacctg agtggataca aagacttact    60
attatacaac atggaataga tgatagcaat tttgatttgt cagaaatggt aca           113

<210> SEQ ID NO 240
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ggtatatcca atattagtga agtaagtgga gacacacctg agtggataca aagactgaca    60
attattcaac atggtattga cgatagtaat tttgatttgt cagacatggt gca           113

<210> SEQ ID NO 241
<211> LENGTH: 113
<212> TYPE: DNA
<213> ORGANISM: Artificial Sequence
<220> FEATURE:
<223> OTHER INFORMATION: Description of Artificial Sequence: Synthetic
<210> SEQ ID NO 242
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggaatatcaa atattagtga agtaacagga gacacacctg agtggataca aagacaaact      60
attatacaac atggtataga tgacagtgta tttgacctgt cagaaatgat aca            113

<210> SEQ ID NO 242
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ggaatgtcca atattagtga agttataggg gaaacgcccg aatggataca aagactaaca      60
attatacaac atggagttga tgatagcgtg tttgacctgt cagaaatgat aca            113

<210> SEQ ID NO 243
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gctatgggga atgcctcaga agtacttggg gagaccccag agtggattgt gcgacaaaca      60
gtagtaggac atgcaatggg agaagcccaa tttagtttat caatgcttgt gca            113

<210> SEQ ID NO 244
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggtatatcca atattagtgt ggtaacaggg gatacgccag aatggataca acgattaact      60
gttatacaac atggaataga tgatagtgta tttgacctat cggacatggt aca            113

<210> SEQ ID NO 245
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ggaatgtcta atataagtga agtgtcaggt actacgccag aatggataca gcgattaaca      60
gtaatacagc atggaataga tgacagtgta tttgacctgt ctgatatggt aca            113

<210> SEQ ID NO 246
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246

```
ggtatatcaa atgccagtac agttataggg aagcaccag aatggataac acgccaaact     60
gttattgaac atgggttggc agacagtcag tttaaattaa cagaaatggt gca           113
```

<210> SEQ ID NO 247
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247

```
ggtatatcaa atgccagtac agttataggg aagcaccag aatggataac acgccaaaca     60
gttattgaac acgggttggc agacagtcag tttaaattaa cagaaatggt gca           113
```

<210> SEQ ID NO 248
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248

```
ggcatttcaa atgcaagtac agttataggg gaggcgccgg aatggataac gcgccagacc    60
gttattgaac atagtttggc tgacagtcaa tttaaattaa ctgaaatggt gca            113
```

<210> SEQ ID NO 249
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249

```
ggtatatcca atgccagtat agtaactgga gaaacaccgg aatggataac aaggcaaacc    60
attgtagaac atgggcttgc agacaaccaa tttaaattag cagacatggt tca            113
```

<210> SEQ ID NO 250
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250

```
agtatatcca atgccagtat agttactgga gaaacgcctg aatggataac aaggcaaacc    60
attgtagaac atgggcttgg tgacaaccaa ttcaaattaa cagaaatggt gca            113
```

<210> SEQ ID NO 251
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251

```
ggtatttcta atgctagtat agtaactggt gaaacaccag aatggataaa aaggcaaaca    60
attgtagagc atggacttgc agataatcaa tttaaattaa ctgaaatggt gca            113
```

```
<210> SEQ ID NO 252
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ggaatatcta atgccagtgt agtaaccggg gaaacacccg aatggataca aagacaaaca      60
attgtagaac attgctttgc agatacacag tttaatttaa cagaaatggt gca            113

<210> SEQ ID NO 253
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ggaatatcta atgctagcat tgtaaccgga gacacaccag agtggattca aagacaaaca      60
attttagaac attgttttgc agatgcccaa tttaatttaa cagaaatggt gca            113

<210> SEQ ID NO 254
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggaatgggta atgggagcga ggtgtccggc acaacaccgg aatggatagc taaacaaact      60
atgttagaac acagctttgc tgacacacag tttagcctaa cagacatggt gca            113

<210> SEQ ID NO 255
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ggaatgggta atggaagtga ggtgtctggc acaacaccgg aatggatagc taaacaaaca      60
atgttggaac atagttttgc tgaagcacag tttagtttaa ctcagatggt gca            113

<210> SEQ ID NO 256
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ggtatgggaa atggtagtga agtatcgggc acaacaccgg aatggataag tagacagaca      60
gtgttagaac acagttttgc agacacacag tttagtttaa caaatatggt gca            113

<210> SEQ ID NO 257
<211> LENGTH: 113
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 257
gctatgggta acggaagtga ggtatatggg gaaacaccag aatggattgt aagacagacg    60
ttggtaggac atagtatgga agatgagcag tttagactat ctgtcatggt aca          113

<210> SEQ ID NO 258
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gccatgggca acggaagtga ggtatatggg gaaacaccag aatggattgt tagacagacg    60
ttggtaggac atagcatgga agacgaacag ttcagactgt cagttatggt aca          113

<210> SEQ ID NO 259
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tccatgggta atgggagtga ggtctatgga gagacaccag aatggattgt gagacagaca    60
ctgataggac acagtatgga ggatgagcag ttcaaattat ctgttatggt gca          113

<210> SEQ ID NO 260
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gccatgggaa acgccagcga ggtgtatggc gaaacacctg aatggatagt aagacaaaca    60
gtggtaggac atgcaatgca agaagcacag tttagtttgt ccatgttagt gca          113

<210> SEQ ID NO 261
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gcaatgggaa atggcagcga ggtgtacggg gaaacccccag aatggatagt aagacaaaca   60
gtagtggggc atgcaatgca agagacacag tttagccttt ctaccttagt aca          113

<210> SEQ ID NO 262
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 262
gcaatgggaa atgcaagcga agtctttggg gaaacaccag aatggatagt aaggcagaca      60
gtaatagggg aggcaatgaa ggaaacccag tttagtctat caacattagt aca            113

<210> SEQ ID NO 263
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gcaatgggca atgcatgtga agtgttaggg gaaacaccag actggatagt acgacaaact      60
gtaattgggc atgcaatggg ggaaacgcag tttagtttat caaaactagt gca            113

<210> SEQ ID NO 264
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gctatgggca atgccagtga ggtgtttggg gacacgccgg actggatagt aagacaaaca      60
gttattggac atgcaatggg agaaacacaa tttagcctat ctgtgttagt gca            113

<210> SEQ ID NO 265
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gccatgagca atgcaagtga ggtgtttggg gaaacgccgg actggatagt tagacaaaca      60
gtaataggac atgcaatggg agaaacacaa tttagcttat cagtactggt gca            113

<210> SEQ ID NO 266
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gcaatgggaa atgcaagtga aacagtaggg gaaacaccag aatggatagt aaggcaaaca      60
gttgtgggac atgcaatgca ggaaacacag tttagcctgt ctgtaatggt gca            113

<210> SEQ ID NO 267
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggcatgggca atgctagtga aataattgga gaaacaccag aatggattgt aagacaaaca      60
```

```
gttgtggggc acagtctaga agaatgccag tttcagttat cagtaatggt gca           113
```

<210> SEQ ID NO 268
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268

```
agcatgggaa acgcaagtga catattcggg gaaacgccag aatggatagt tagacaaact    60
gtggtaggac acagcatgga ggaatgccag tttcagttat cagtaatggt gca           113
```

<210> SEQ ID NO 269
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269

```
agtatgtcca gctgtagcga cgtgtatggg gaaacaccag agtggatagt caggcagaca    60
atggtgggac atgcaatgga ggatgcgcag tttagccttt cagagatggt gca           113
```

<210> SEQ ID NO 270
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270

```
agcatgtcca gctgtagtga tgtgtatgga gagacaccag agtggatagt taggcaaaca    60
atggtgggac atgcaatgga ggatgcgcag tttaccctt cagagatgat aca            113
```

<210> SEQ ID NO 271
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271

```
agcctatcaa attgtagcga ggtgtttggg gaaacaccag agtggatagt taggcagaca    60
gtggtgggac atgcattaga ggaagcgcag ttcagtctgt cagaaatggt gca           113
```

<210> SEQ ID NO 272
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272

```
gccatgtcaa actgtagtga tgtgtatggg gaaacaccag agtggatagt gagacaaacg    60
atggttggac atgcactaga ggaagcacag tttagtctgt cggagatggt aca           113
```

```
<210> SEQ ID NO 273
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
agtatgtcca atattagtga tgtgtatggc gagacacctg aatggatagt aagacagaca      60
atggtaggtc acgcattaca agaagtacag ttcagtttat ctgaaatggt aca           113

<210> SEQ ID NO 274
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ggtatgtcta atattagtga agtgtatgga gacactccgg attggatagt aagacaaaca      60
attgtgggac atgctttaga agagacacag tttcggttat cagacatggt aca           113

<210> SEQ ID NO 275
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gggctgtcca atgcaagtga aatatttggt acacccccgg aatggctggc cagacaaact      60
gtaattgaat atagcttagc agacagccag tttgatttat ctaaaatggt aca           113

<210> SEQ ID NO 276
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ggtatggggt caggcgcatt tacccatggc acatatcctg attggattgc acatcaaaca      60
attttgggcc atcaaaatgc tgaagcaagc acatttgatt tttcagccat ggtcca        116

<210> SEQ ID NO 277
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ggtatggggt caggagcatt tacatatggt aaatatcctg attggattgc gcagcaaaca      60
gtacttggcc accaaaatgc ggaggcaagc acatttgatt tttcagtgat ggtaca        116

<210> SEQ ID NO 278
<211> LENGTH: 116
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 278
ggaatgggga caggaacatt cacgtatggt tcataccctg attggattgc acatcaaaca      60
attcttggcc atcaaagtgc tgaagcaagc acctttgatt tttctgtaat ggtaca         116

<210> SEQ ID NO 279
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gcaatggggt ccggagcatt ttctcatggt ccatatccta actggatggc acagcaaact      60
attgttggtc atcagagcac agaagccagt gcttttgact tgtctgaaat gattca         116

<210> SEQ ID NO 280
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
gcgatggggt ctggagcatt tacttatgga ccttatcctg attggattgc ccagcaaaca      60
attgttggtc atcaaagtac agaagccagt gcatttgata tgtctgcaat ggttca         116

<210> SEQ ID NO 281
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
gcaatggggt cagggacatt tacttatggt ccctaccctg attggatggc acatcaaact      60
attgttggcc atcaaagtac agaagcaaat gcatttgata tgtctgttat ggtgca         116

<210> SEQ ID NO 282
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tgtatgggat cggggcgtt tagccatgga ccatatcctg attggattgc ccaacaaact      60
atattaggtc acaaaagtgc tgaggcaagt acttttgatt tttcagcaat ggtcca         116

<210> SEQ ID NO 283
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 283
tgtatgggac ctggagtgtt cacccacggt ccttaccctg aatggattgc acaattaacc       60
attttgggcc ataagagtgc tgaggcaagt gcgtttgatc tgtcagtcat ggttca         116

<210> SEQ ID NO 284
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
tgtatgggat ctggagggtt tacttatggt ccatacccag attggatagc acaacaaaca       60
atattaggtc atcaaaatgc tgaagcaagt agttttgatt tgtctgaaat gattca          116

<210> SEQ ID NO 285
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tcaatgggtt ccggagtatt tacatatggc tcatatccag attggatagc ccaccaaaca       60
atattgggcc atcaaagcgc tgaagctagt acatttgatc tatcggacat ggttca          116

<210> SEQ ID NO 286
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
agctcaaatg ctgctacctt tacacatggg tcttatccta aatggattat agaacaaaca       60
ctgataggac atcaaacagg agaagctgca acgtttgaca tgtccacaat ggtaca          116

<210> SEQ ID NO 287
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
agttccaact cgggaacatt tacccatggt tcatatccta aatggatagt agaacaaaca       60
ttaataggac atcagtctgg agaagcggca acatttgata tgtcaactat ggtaca          116

<210> SEQ ID NO 288
<211> LENGTH: 119
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gctatgttaa cagagagttc tgttttttgga caaacaccgg attggatcgc aaaacaaact      60
ctcgtaagtc atcaagcagc aactactgca gagactttg agttatctag aatggttca    119

<210> SEQ ID NO 289
<211> LENGTH: 119
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gccatgttaa cagagagctt tgttttcgga cagacaccag attggattgc aaagcaaacc    60
ttagtaagcc atcaagcagc aactactgca gaaacattcg aattatcaaa aatggttca    119

<210> SEQ ID NO 290
<211> LENGTH: 119
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gctttgttaa ctgaatgctt tgtatatgga caaacaccgg attggatcgc taagcagaca    60
atagtgagcc atcagtctgc tacaactgca gaaacatttg agttgtcaag aatggttca    119

<210> SEQ ID NO 291
<211> LENGTH: 119
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
tcatttggaa atgcatcgtt tatttatgga ccgtttccag attggttagc aaaattaact    60
atgttagacc atgaatccgc cgcgagctca gaacagtttg aacttgctca aatgattca    119

<210> SEQ ID NO 292
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
attataactg atacatgttt taaatatggc actttgcctt cctgggttag tagattaact    60
atagtagaac atcagttagc ttcagcagac acattttcat tatctgaaat ggtaca    116

<210> SEQ ID NO 293
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gtaatagcag atacctgtta taaatatgga gacttcctg actggatagc cacacatact    60
gttataaatc atcagctagc aactgcagac agctttaaat ttagtgatat ggtaca    116

<210> SEQ ID NO 294

<211> LENGTH: 116
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 294
agtatgaatc caaatgtgta tgcccacggt gaatatcctg agtggatttt aacacaaact    60
atgattaatc atcaaacagc acaggcaaca caattcgatc tatctaccat gataca       116

<210> SEQ ID NO 295
<211> LENGTH: 116
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 295
agcatgaatc caaatgtcta tgcacatggt gaatatcctg agtggattat gacacaaacc    60
atgatcaatc accaatcagc agaagctaca caatttgatt tatccactat gataca       116

<210> SEQ ID NO 296
<211> LENGTH: 116
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 296
agtatgaatc caaatgttta tgctcatgga gaatatcctg agtggataat gacacaaaca    60
atgataaatc accaaacagc agaagctaca cagtttgatt tatctactat ggtaca       116

<210> SEQ ID NO 297
<211> LENGTH: 116
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 297
agtatgaatc ctaatgttta tgctcatgga gagtatcctg aatggataat gacgcagaca    60
atgataagcc atcatacagc agaagctaca cagtttgatt tatctactat ggtaca       116

<210> SEQ ID NO 298
<211> LENGTH: 116
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 298
agtatgaacc ctaatgtata cgcacatggt gcgtatcctg aatggatact tacacaaaca    60
ctaattaatc accaatctgc aaatgctaca caatttgact tatcgacaat gataca       116

<210> SEQ ID NO 299
<211> LENGTH: 119
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 299
agtatggact catctgtgta tgctcacgga acgtatcctg attggattgt gaatcagacc      60
atgttaacac atcaggctgc agcagaagct gtgcaatttg atttgtctca aatgataca     119

<210> SEQ ID NO 300
<211> LENGTH: 119
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 300
agtatggact catctgtgta tgctcacgga acctatcctg attggatagt aaatcagacc      60
atgttaacac atcaggctgc agcagaagct gtgcaatttg acttatctga aatgataca     119

<210> SEQ ID NO 301
<211> LENGTH: 119
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 301
agtatggact catctgtgta tgctcatgga gcctatcctg attggattgt aaatcagacc      60
atgataagtc atcaggcagc agcagatgct atgcaatttg acctttctga aatgataca     119

<210> SEQ ID NO 302
<211> LENGTH: 116
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 302
agtatgaatc caaatgtcta tgcatttgga gagtatcctg agtggattat gacacagact      60
atgatacatc accaaactgc tgacagtgta caatttgacc tgtctgaaat gataca        116

<210> SEQ ID NO 303
<211> LENGTH: 116
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 303
agtatgaacc taatgtata tgcatttggt gagtatcctg agtggattgt gacacaaacc       60
atgatacaac atcaaactgc tgacagtata caatttgatt tgtctcgtat gattca        116

<210> SEQ ID NO 304
<211> LENGTH: 116
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 304

```
agtatgaatc caaatatcta tgcatttggg gagtatccag actggattgt tcagcaaacg    60
atgattagtc accatgaggg cgataatttg caatttgaat tgtctcctat ggtaca       116

<210> SEQ ID NO 305
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
agtttgaata gtaatgtgtt ttgttttggt gaagctcctg attggattct atcacaaaca    60
atgatacagc atcaaactgc tgacactttg cagtttgact tgtctcgaat gattca       116

<210> SEQ ID NO 306
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
tctatgaata aaaatgtata tacccatgga gaatacccag agtggatagc aaatcaaaca    60
ttgctttctc atcaggaata tgaaacacag caatttgatt taagtagaat gattca       116

<210> SEQ ID NO 307
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
tctatgtctt caactgtttt tacatggggt acaactttgg agtggattgc acagcaaacc    60
cttattaatc atcagttaga ttccgaaagt ccctttgagc tttgtaaaat ggttca       116

<210> SEQ ID NO 308
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tctatgtctc cagctgtata tacctgggga gaaatgccag attggatggc gcagcagaca    60
ttgttgaatc atcaattagc atcagaaaag catttgaat tgtcacaaat ggtaca        116

<210> SEQ ID NO 309
<211> LENGTH: 110
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tttatgggta caggggtat aaaacatggc gcaatgccag aaataattgt aaaccagtgc     60
gtggtgtcta atcagcagac agacacccttt gaattatcac gtatggtaca             110
```

```
<210> SEQ ID NO 310
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tgtatgggat cggggtgtt cagttatggg ccatatcctg attggattgc acaacagact    60
atattaggtc acaataatgc tgaagcaagc acctttgatt tttcacagat ggtaca       116
```

MULTIPLEXED ASSAY AND PROBES FOR IDENTIFICATION OF HPV TYPES

CROSS-REFERENCE TO RELATED APPLICATIONS

This application claims priority from U.S. Provisional Patent Application No. 60/773,601 filed on Feb. 14, 2006, which is hereby incorporated by reference in its entirety.

STATEMENT OF GOVERNMENTAL SUPPORT

This invention was made with U.S. Government support under National Institutes of Health Grant 00025. The Government has certain rights in this invention.

REFERENCE TO SEQUENCE LISTING

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of detection of human papilloma virus (HPV), identifying specific types of HPV, and further to the fields of nucleic acid diagnostics, nucleic acid amplification, and microarrays.

2. Related Art

HPV Types and Classification

To date, over 100 HPV types that infect either cutaneous or squamous epithelia have been identified, and most of these HPV types have been associated with the development of benign or malignant lesions. Through the years different HPV types have been classified according to several criteria such as cutaneous or mucosal types; skin or genital types. However, some discrepancies were seen, as HPV infections identified in some patients did not fit into these specific criteria. Modern classification of HPV is based on the sequence differences that can be identified in the transformation genes E6 and E7 as well as the capsid gene L1 of the virus. A new type of HPV is classified if it shares less than 90% homology for these regions with an already described HPV type. Furthermore, subtypes of HPV consist of types that have 90-98% homology within a genotype, while those with greater than 98% homology within a subtype are described as variants. At present, various types of HPV are categorized according to their association with certain clinical disorders (Table 1). Therefore, HPV types such as HPV-1 and 2 are associated with the development of skin warts, while other types such as HPV-13 and 32 are associated with disorders of the upper respiratory tract.

TABLE 1

Classification of HPV according to clinical association

| Disorder | HPV Type |
| --- | --- |
| Warts of the skin | 1, 2, 3, 4, 7, 10, 26, 27, 28, 29, 41, 48, 49, 57, 60, 63, 65 |
| Upper respiratory tract | 2, 6, 11, 13, 16, 32 |
| Epidermodysplasia verruciformis | 5, 8, 9, 12, 14, 15, 17, 19, 20, 21, 22, 23, 24, 25, 36, 38, 47, 50 |
| Anogenital warts | 2, 6, 11, 16, 18, 30, 40, 41, 42, 44, 45, 54, 55, 61 |
| Angiogenital carcinomas | 16, 18, 26, 31, 33, 35, 39, 45, 51, 53, 56, 58, 59, 66, 68, 73, 82 |

Squamous HPV types have been grouped as high-risk or low-risk depending on their transformation capabilities (Table 2) (van den Brule A. et al., 1992), with the high-risk HPV types showing a relative risk (RR) close to 100 for their association with cervical cancer (Duarte-Franco E. & Franco E., 2004). HPV types considered to be high-risk are: HPV-16, -18, -31, -33, -35, -39, -45, -51, -52, -56, -58, -66 and 69; while HPV-6, -11, -34, -40, -42, -43, and 44 are considered to be low-risk (Kleter, B et al., 1999; Jacobs M V. et al 1995).

TABLE 2

Overview of the high-risk and low-risk HPV types
HPV types

| High-risk | HPV-16, -18, -31, -33, -35, -39, -45, -51, -52, -56, -58, -66, -69 |
| --- | --- |
| Low-Risk | HPV-6, -11, -34, -40, -42, -43, -44 |

Malignant Transformation by HPV

The two early genes E7 and E6 of high-risk HPV types have been associated with the transformation capabilities of the HPV virus, whereas no such function has been seen for the low-risk HPV types. It has been shown that both genes of high-risk HPV types integrate into the host genome, while those of the low-risk do not (Longworth M and Laimins L., 2004). The integration of the genes results in the disruption of the repressor activity exerted by E2 on the oncoproteins E6 and E7. The mechanisms that are used by these two genes to cause cell transformation have been well investigated and these studies have shown that the early gene E6 inhibits the functions of p53, while E7 interferes with the function of retinoblastoma (Rb) gene.

E6 is thought to degrade p53 at a higher rate than normal through an ubiquitin pathway. E6 recruits a cellular ubiquitin ligase called E6-associated protein (E6AP) with which it forms a complex and replaces the p53 degradation function that is usually carried out by the mdm-2 protein (Longworth M and Laimins L., 2004; zur Hausen H, 2000; Scheffner et al., 1993; Werness et al., 1990). This action is thought to be one of the causes of cancer development as it abolishes the normal function of p53, which is to regulate the expression of proteins that are involved in cell cycle control. The regulation of proteins such as p21, a kinase inhibitor, by p53 results in cell cycle arrest or apoptosis and abolishing these actions can result in carcinogenesis.

Cancer and HPV

The involvement of HPV in the development of cancer mainly cervical cancer has been well documented. This notion was first postulated by Harold zur Hausen and further established with the isolation of HPV 16 from cervical cancer in 1983 (zur Hausen H, 1983). Moreover, HPV is detected in over 90% of cervical cancer. Cervical cancer is one of the most common malignant diseases among women, with more than 500,000 women worldwide being diagnosed with the disease annually (Duarte-Franco E. & Franco E., 2004). Two forms of cervical cancer have been identified, primarily squamous cell carcinoma (SCC) and the rarer cervical adenocarcinoma (AC) (Wang S et. al, 2004). HPV-16 has been predominantly identified in the development of SCC; while HPV-18 has been associated with AC. Precursor lesions, known as cervical intraepithelial neoplasia (CIN) usually precede the development of cervical cancer. These lesions have been classified according to the irregularity in the cells (CIN I), mild to moderate abnormality of the cervix surface lining (CIN II) or full abnormality of the cervix surface lining (CIN III). As with other types of cancer, cervical cancer develops as a result of accumulation of multiple genetic alterations associated to several risk factors. Although risk factors such as smoking, parity, sexual behavior, and the Human Immunodeficiency Virus (HIV) infection have been associated with the development of cervical cancer, the main risk factors are the high-risk HPV (Duarte-Franco E. & Franco E., 2004).

In addition to the involvement of HPV in the development of cervical cancer, it has also been associated with some forms of head and neck squamous cell carcinomas (HNSCC). Over 400,000 cases of HNSCCs are diagnosed annually and studies have shown that in addition to the common risk factors such as smoking and or alcohol consumption, HPV infection might also play a role in this disease. Several studies have been conducted investigating the association of HPV with HNSCCs. One such study performed by Klussmann and colleagues (Klussmann J. et al., 2001) presented evidence of a 26% occurrence of HPV infection in 98 tested HNSCC patients. Furthermore, this study showed that the location of the tumor might also be a factor in the association of HPV infection and cancer development. The frequency of HPV positive cells differs according to the localization of the tumor, with the highest frequency seen in oropharyngeal cancers (45%), and particularly cancer of the tonsil (58%). The HPV type that was frequently detected in these types of cancers was HPV-16; it was detected in 21 of 25 HPV positive tumors. Other HPV types that have been detected are HPV-19 and HPV-33 (Klussmann J. et al., 2001). Other studies performed by McKaig (McKaig et al., 1998) provided evidence of the presence of HPV DNA in 35% of head and neck cancers. These findings were confirmed by Gillison and colleagues (Gillison et al., 2000) with a study performed with 253 tumor samples.

The involvement of HPV in skin cancer was first described in patients with Epidermodysplasia Verruciformis (EV) (Pfister H. 2003; Berkhout R. et al., 2000; Orth G. et al., 1979), who are more susceptible to HPV infection because of a genetic disorder of their immunological system (Weissenborn S. et al., 1999; Berkhout R. et al., 1995). Although several HPV types have been detected in EV patients, HPV types such as 14, 17, 20, 47, 5, and 8 are regarded as high-risk types (Pfister H. 2003; Farve M. et al., 1998; Berkhout R. et al., 1995). Studies have shown that these HPVs are present in high copy numbers and suggest that the infection might be present throughout the development and metastasis of the tumor (Pfister H. 2003).

Current HPV Detection and Typing Techniques

The development of a technique that is capable of detecting and typing HPV efficiently is seen as a possible tool to aid in clinical prognosis and therapy. Most of the current techniques are polymerase chain reactions (PCR) based methods that use consensus primers such as MY09-MY11, PGMY09-PGMY11, and GP5$^{+-}$-GP6$^+$ to detect HPV, which can be subsequently used in combination with other techniques such as cycle sequencing and dot blots to type or subtype different HPVs (Klaassen C et al., 2004). Although most of these methods have great advantages for being especially sensitive there are also some disadvantages to these methods. The following section will discuss methods that are currently being studied for their use in the detection and typing of HPV.

PCR Based Methods

MY09 and MY11 are degenerate consensus primers that are located in the L1 region of the HPV genome. They consist of 24 pairs of primers that are able to detect more than 30 genital HPV types (Husnjak K et al., 2000; Gravitt P. et al., 2000). This method has been a gold standard in studies to investigate the association between HPV and cervical cancer. However, the results obtained with regard to the sensitivity varied for the different HPV types and the efficiency of the amplification were compromised by the formation of secondary structures (Husnjak K et al., 2000). Moreover, some studies have suggested that the results were frequently irreproducible. As a result of these disadvantages that have been observed an improved set of primers has been generated, PGMY09 and PGMY11, which are a pool of 5 upstream and 13 downstream primers respectively. The primers were designed to bind to HPV types that contain sequence homology in each of the two primer binding regions (Gravitt P. et al., 2000). Studies have shown that the new set of primers improved the sensitivity, specificity, and reproducibility. A similar set of primers to MY09-MY11 was designed by Novelli G. and colleagues (Novelli G. et al., 1992) with the exception of an inosine inclusion at the degenerated positions. They presented the pI-1 and pI-2 primers, which proved in their study to be efficient in the amplification of the L1 region of the cervical cell line CaSki. A study performed by Husnjak K. and colleagues (Husnjak K et al., 2000) showed that the pI-1/2 primers were less sensitive than the MY09-MY11 primers but presented evidence for their possible use in the screening of unknown HPV types. The general primers GP5$^+$ and GP6$^+$ are also designed for the L1 region of the genome and are located within the MY09-MY11 primers (Husnjak K et al., 2000; de Roda Husman A et al., 1995 Snijders P et al., 1990). The primer pair can be used as a two-stepped nested PCR or a one step PCR. In the case of the nested PCR GP5 and GP6 are used in combination with the consensus primer pair MY09/MY11 or PGMY09/PGMY11. A study performed by Evander and colleagues (Evander M et al., 1992) compared both methods and stated that the nested PCR increases the sensitivity of the results. However, the possibility for contamination also increases. These sets of primers are considered more effective than the MY or PGMY primers because the PCR-product generated is of a smaller size, which allows for fewer errors. Another set of primers complementary to the L1 region was designed by Yoshikawa H. and colleagues (Yoshikawa H, et al., 1990). The L1C1, L1C2-1 primers were designed to amplify nine HPV types (HPV-6, -11, -16, -18, -31, -33, -42, -52 and 58) and an additional primer; L1C2-2 amplifying one particular HPV type (HPV-58) was also designed. The different methods that have been mentioned are applied the most, but there are several others such as short PCR fragment (Kleter B. et al., 1998) that are currently used for the detection of HPV. Since the homology between the different HPV types is similar other techniques are combined with these PCR methods to type HPV, including cycle sequencing, line blotting and pyrosequencing (Klaassen C et al., 2004). Table 3 gives an overview of the different primers mentioned.

TABLE 3

Overview of different general primers designed to the L1 region

| Primer Set | Sequence | Reference |
|---|---|---|
| MY09 | CGTCCMARRGGAWACTGATC (SEQ ID NO: 1) | Manos et al., 1989 |
| MY11 | GCMCAGGGWCATAAYAATGG (SEQ ID NO: 2) | |
| pI-1 | GCICAGGGICATAAIAATGG | Novelli et al., 1992 |
| pI-2 | CGTCCIAIIGGAIACTGATC (SEQ ID NO: 3) | |
| L1C1 | CGTAAACGTTTTCCCTATTTTT (SEQ ID NO: 4) | Yoshikawa et al., 1990 |
| L1C2-1 | TACCCTAAATACTCTGTATTG (SEQ ID NO: 5) | |
| L1C2-2 | TACCCTAAATACCCTATATTG (SEQ ID NO: 6) | |
| GP5 | TTTGTTACTGTGGTAGATAC (SEQ ID NO: 7) | Snijders et al., 1990 |
| GP6 | GAAAAATAAACTGTAAATCA (SEQ ID NO: 8) | |

In addition to the techniques mentioned above, there are several other techniques that are being investigated for their usage in HPV detection. One such technique is the Roche AMPLICOR HPV test (Roche Molecular Systems). The test is capable of detecting 13 of the high-risk HPV types and as a positive control the presence of human β-globin is also assessed. The target DNA is amplified and subsequently hybridized for the detection process. A study performed by Monsonego and colleagues (Monsonego J. et al., 2005) concluded that like the HC-II test, the AMPLICOR HPV test, is sensitive enough to detect HPV infection in high-grade lesion. However, they also concluded that the specificity of the test is not as high as the current cytology methods. The AMPLICOR HPV Test amplifies a sequence of nucleotides within the polymorphic L1 region of the HPV genome that is approximately 165 bp in length.

In addition to the AMPLICOR HPV test, a detection/genotyping technique, INNO-LiPa assay was also developed. The INNO-LiPa test (Labo Biomedical Products by, Rijswijk, The Netherlands) is able to detect 25 different HPV types simultaneously and was shown to be sensitive and specific by studies performed by Kleter et al. (1999) and Melchers et al. (1999). This is a short PCR fragment assay (INNO-LiPA HPV detection/genotyping assay, $SPF_{10}$ system version 1), which amplifies a 65-bp fragment of the L1 open reading frame and allows detection of at least 43 different HPV types.

Hybrid Capture Assay

In addition to the PCR based methods, there are other techniques such as Hybrid Capture (HC) (Digene Corporation, Silver Spring, Md.), which is a hybridization assay that uses RNA probes to type both high-risk and low-risk HPV types.

The Hybrid Capture I (HC-I) was introduced commercially as a non-radioactive assay capable of detecting 14 HPV types (HPV-16, -18, -31, -33, -35, -45, -51, -52, -56, -6, -11, -42, -43 and 44) (Clavel C. et al., 1999; Farthing A. et al., 1995; Schiffman M et al., 1995; Sun X et al., 1995). The technique targets HPV DNA, which are subsequently hybridized with HPV-type specific RNA's. Followed by capture of the DNA/RNA hybrids and signal amplification by binding of the hybrids to multiple conjugated antibodies that specifically recognize DNA/RNA hybrids. The samples are considered positive for high-risk HPV if their assay's chemiluminescence is at least that of the average of three positive assay controls (Snijders et al., 2003, Zielinski G. et al., 2003). A study carried out by Sun XW and colleagues (Sun X et al., 1995) suggested that the test was a sensitive and accurate method to identify high-risk HPV types. However, another study by Clavel C and colleagues (Clavel C. et al., 1999) suggested that the test might not be as sensitive as the current cytology screening technology when it comes to the high-grade lesions. An improved version of HC have been introduced, the HC-II, which is able to detect an additional four HPV types (HPV-39, -58, -59 and 68). Clavel C and colleagues (Clavel C. et al., 1999) performed a study with the HC-II and concluded that the sensitivity of the test was similar to that of PCR using consensus primers and greater compared to cytology screening of high-grade lesions. Although HC shows promising results with an increase in the sensitivity compared to other techniques it also has the disadvantage of providing more false positive results. However, some studies have suggested that because HC is an liquid hybridization test it requires a higher viral load for the detection of HPV DNA (van Ham M. et al., 2005).

DNA Microarray Chips

HPV DNA microarrays have been developed with the notion of being capable of detecting multiple HPV types in a single sample and through one hybridization step. There is currently one commercially available DNA microarray chip, which was introduced by Biomedlab Company, Seoul, Korea. The chip, HPVDNAChip™, contains 22 HPV type specific probes of which 15 are high-risk HPVs (HPV-16, -18, -31, -33, -35, -39, -45, -51, -52, -56, -58, -59, -66, -68, and 69) and 7 are low-risk HPVs (HPV-6, -11, -34, -40, -42, -43, and 44). For the application of the test, DNA is collected, isolated, subsequently amplified with the general primers GP5 and GP6, and then hybridized to the chip. Studies utilizing the HPVDNAChip performed by groups such as Lee S. et al. (2003) and Jung An H. et al. (2003) gave promising results with high sensitivity detection rate.

Klaassen C and colleagues (Klaassen C et al., 2004) disclose another microarray technique in which they used digoxigenin-labeled HPV-derived PCR amplicons that were hybridized onto biotinylated HPV probes. The hybridized amplicons are then visualized by a staining procedure with a substrate for alkaline phosphatase that has both colomeric and fluorescent properties. Test uses the C terminus of the HPV E1 gene and type-specific probes as well as primers for 53 HPV types. A total of 45 HPV types were identified by a single type-specific probe. It has been proposed that this assay would be more inexpensive than other techniques that are now available. Furthermore, the quantity of HPV types that could be detected with this assay is greater than others and it is also able to detect HPV types that are not yet classified (Klaassen C et al., 2004).

Thus, there are various HPV testing methods available that are being investigated or used to aid in the prognosis and therapy of cervical cancer. These techniques have many advantages but there are also disadvantages. Such is the case for general and consensus primers; the sensitivity percentage is high on one hand but the reproducibility and the ability to detect multiple HPV infection are not optimal (Oh T. et al., 2004). The development of the HPVDNAChip and other DNA microarray has also provided promising results, but the number of types that can be detected are limited such is the case with the HC technique.

BRIEF SUMMARY OF THE INVENTION

The following brief summary is not intended to include all features and aspects of the present invention, nor does it imply that the invention must include all features and aspects discussed in this summary.

In one aspect, the present invention provides an array comprising a plurality of distinct locations, each location having a probe comprising a nucleic acid sequence complementary to specific genotype of HPV E1 sequence. The array preferably is prepared by spotting DNA oligonucleotides onto predetermined positions on a flat substrate made of glass or similar material (e.g. quartz, silicon, etc.). It may be implemented by other means, such as beads, wells, or microfluidics. The array contains a number of probes, including positive and negative controls and sufficient probes to identify at least the significant genotypes of HPV (as referenced in Table—1 and 2, for example). Accordingly, the array may comprise individual probes for HPV genotypes 16, 18, 29, 31, 44, and 66; or individual probes for HPV genotypes 16, 18, 31, 33, 35, 39, 45, 51, 52, 56, 58, 66, 69, 6, 11, 34, 40, 42, 43, and 44.

The probes are preferably between 30 and 60 nucleotides, but may be as small as 20 nucleotides and up to several hundred nucleotides in length. Preferably, each probe comprises a sequence at least 90% identical to a sequence listed in Table 5 and is approximately (within 10 percent) the same length. In order to design a variant sequence, one may refer to known genotype sequences of the HPV genotype in question, as well as alternative designs for different DNA amplification methods, different control sequences, different tether sequences, and different probe lengths.

Preferably, each probe contains binding regions for two target sequences, one sequence being a positive control sequence which is essentially identical for each probe, the second sequence being unique for an HPV genotype. The control sequence allows normalization of signals between array spots in which variations in spot size and quality are present as a result of the inkjet or dip pen spotting. The control sequence will have a different label than the target sequence. The target sequence is preferably labeled through the use of labeled PCR primers.

Thus there is provided, in one aspect, a method for detecting and typing HPV in a sample, comprising the step of contacting the sample with a plurality of polynucleic acids, each polynucleic acid being complementary to a different type of HPV E1 gene. To increase sensitivity, the method preferably comprises the step of amplifying HPV DNA from an HPV E1 gene, such as by PCR, rolling circle amplification, ligase chain reaction (LCR) (LCx; Abbott Laboratories), or a strand displacement amplification assay (BDProbeTec amplified DNA assay; Becton Dickinson and Co.).

In one method, based on PCR, one may carry out the steps of: contacting the sample with a mixture of amplification primers, each hybridizing to one or more E1 regions, said mixture comprising pairs of primers directed to at least 20 (preferably at least 89) genotypes of HPV; amplifying any HPV DNA in the sample using the primers to produce amplicons; and contacting the amplicons with probes unique for each genotype to be detected. The amplicons may be specific to 1-6 types of HPV. A large mixture of primers may be used simultaneously because the primers are designed to be similar in sequence so as to prevent dimerization and amplification artifacts. As described above, the method may comprise the step of contacting the probes with a positive control hybridizing to each probe. The method can simultaneously detect all known HPV genotypes, i.e. genotypes 1 through 89, by binding unique probes under stringent conditions to E1 gene target sequences. Additional genotypes may be added to the assay as their E1 sequences become known, following the directions below.

In another aspect, the present invention comprises a method for detecting a specific HPV type by contacting a sample with a collection of polynucleotides, which can act as PCR primers, and which are specific for between one and about 4-7 different HPV types. In the preferred embodiment a collection of sixty-six PCR primers (including forward and reverse) covers about 88 different HPV types. These primers are used together, in a multiplexed assay, and thus will amplify any HPV present in the sample. The HPV type is then further identified in a second, probe, stage, where the amplified DNA is hybridized to a specific sequence that is unique for each HPV type.

Thus the invention may be implemented in kit form, providing a pre-formed array, primer collection and/or other reagents. The kit may comprise a set of labeled primers for amplifying specifically HPV E1 gene sequences; and a set of probes for binding uniquely to an individual HPV E1 gene sequence amplified by the primers. The kit may comprise a set of primers as set forth in Table 4, wherein each primer is at least about 90%-99% identical to the other primers listed in Table 4, at least one primer in each set including a label which is biotin or a fluorescent label. Also, the kit may comprise an array wherein the probes are immobilized as a spot on a solid substrate. A probe may be provided for each known HPV genotype.

BRIEF DESCRIPTION OF THE DRAWINGS

FIG. 2 is a drawing representing a view of microarray results from different cell lines, wherein an empty circle represents a green spot, a solid circle represents a red spot, and a triangle represents a yellow spot; FIG. 2 (A) illustrates a chip microarray of C33A: no positive signal; FIG. 2B illustrates a microarray chip of SW765: HPV-18 and HPV-39 were detected; and FIG. 2 C is microarray chip of ME-180: HPV-16 was detected (The whole microarray is not depicted in the figure); and FIG. 3 is a drawing representing view of microarray results from genomic samples, wherein an empty circle represents a green spot, a solid circle represents a red spot, and a triangle represents a yellow spot; Hybridization assay of genomic samples. FIG. 3A illustrates an example where Sample 4, HPV-16 was detected. FIG. 3B illustrates and example of Sample 11, HPV-18 (low signal), -19, -20 and 45 (low signal). (The whole microarray is not depicted in the figure.)

DETAILED DESCRIPTION OF THE PREFERRED EMBODIMENT

Overview

Figure 1:
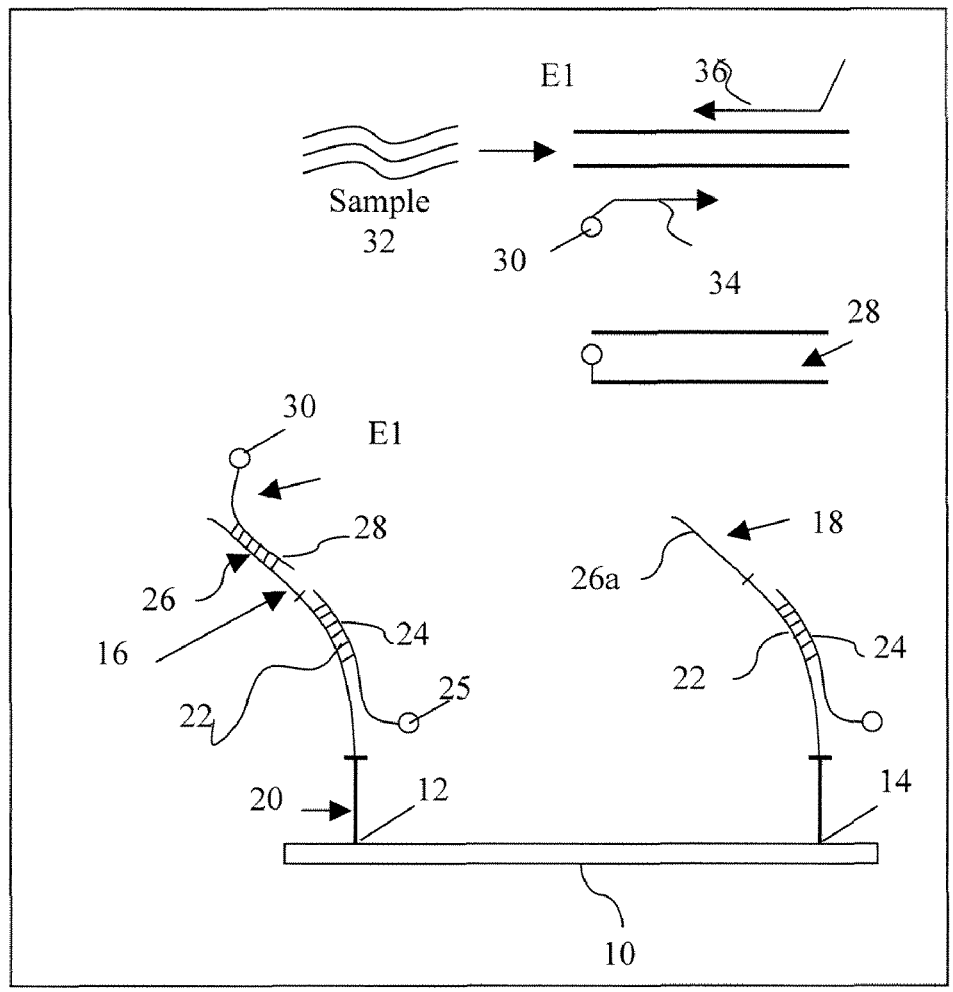
FIG. 1 is a schematic diagram depicting the present probes and array.

A DNA microarray in the form of a chip was developed. Degenerate primers capable of amplifying approximately 90 HPV types were designed to target the E1 region of the gene. The design of the array allows for the identification of more HPV types than prior art methods (Klaassen C et al., 2004; Snijders P. et al., 1990; Gravitt P. et al., 2000). Most techniques that are currently used focus on detecting and typing HPV types that are known to be involved in the development of malignancies. Therefore, these techniques may perhaps contain the most known high-risk HPV types and some low-risk types but exclude the HPV types that have not yet been classified and associated with and clinical disorders. With the wide-range of HPV types that can be identified with this technique, other HPV types can also be investigated on their association with the development of other type of cancer.

Given that the chip uses the E1 region of the HPV gene as a target, the disadvantage that may exists because of possible deletion in the L1 region can be circumvented. Past studies have suggested that in some cases an L1 deletion may occur as the virus genome integrates in the host's genome (Oliviera L. et al., 2002). Since most current methods use the L1 region as the target region for their testing, this may lead to false negative results. With the development of this assay a possible HPV testing technique is introduced that can aid not only in the prognosis and therapy of cervical cancer but also in that of the other malignancies in which HPV have been shown to play a role.

The criteria for selecting the E1 region for the design of the microarray chip probes and primers came from the observation that current techniques, which utilize the L1 region for the detection of HPV, have the disadvantage that detection of rarer forms of HPV types, especially if they are present as multiple infections, is not efficient enough. Moreover, this region was selected because it appears to be highly variable and less vulnerable to mutation variation, making it the ideal region for the design of probes and primers.

In addition to the HPV type specific region, the probes were designed to have a linker region (termed "Linker A") as an internal control to see the quality of the probe printed on the chip in addition to a poly T region (from 1 to about 6 thymine residues) to construct a collection of probes in which each probe is about the same length. These two additional regions make hybridization of the target DNA to the HPV type specific region of the probe more accessible as the HPV region sits higher rather than directly on the slide. By using the amplification primers as a pool, any additional HPV present in the sample can be amplified. With over 60 primers in a PCR reaction, there is a generation of primer dimers in the pool but because the primer sequences are not complementary to the probes on the chip the fear of cross-hybridization is minimized. The approach to investigate the possibility of cross-hybridization (hybridization with non-corresponding probes) is through the cloning of the amplicons and subsequent sequencing of the product. This was done in part with the E1 and L1 primers that were developed showing the product identified was indeed of that specific HPV type.

Detection of HPV types in the present microarray system can occur even when there are deletions in the L1 region (Oliviera L. et al., 2002). Deletions in the L1 region will result in false negative results by techniques that use the L1 region for their detection purposes. As mentioned previously, E1 and L1 amplification primers were designed to confirm if the additional HPV types that were detected were in fact present. The results were promising as the regions that were observed on gel were indeed present when Sanger sequencing was performed. It was also shown that deletion can also exist in the E1 region of the HPV genome. The primers that were designed for this section of the study targeted at most only 300 bp of the respective region, therefore amplification primers targeting the whole E1 and L1 regions were also developed to further present more definite results.

It can also be concluded that the microarray chip might be more sensitive for detection of HPV types that may not be dominantly present during a multiple HPV infection. For example, HPV 16 is a very dominant HPV type and its presence may interfere with the detection of other types that might not be as dominant. This notion was illustrated with the results that were obtained with pyrosequencing of the genomic DNA and their subsequent use in the hybridization assay and amplification by E1 and L1 primers. HPV-16 was predominantly detected with pyrosequencing using GP5+ as sequencing primer, while the present microarray chip detected another high-risk type, HPV-66, which is also amplifiable with GP5+; further testing with the E1/L1 primers and Sanger sequencing did confirm the presence of this HPV type in the genomic DNA samples.

FIG. 1: Diagrammatic Overview

FIG. 1 represents an array designed according to the methods and materials described here. A microarray substrate 10 has different regions or spots 12, 14 to which are attached probes 16, 18. Most probes comprise a short sequence portion 20 (e.g., polyT), adjacent the control "linker A" portion, for attachment to the substrate. The number of T residues (at the 5' end of the probe) is selected on the basis of the desired length of the probe. The 5' end is modified with an amino terminus for bonding to the substrate. All probes are of the same approximate length. Next, a control region 22 ("Linker A") is present on each probe. It is the same sequence on each probe. The control sequence hybridizes to a control target 24 labeled, as shown at 25, e.g. with Cy3. Since the control region 22 is present on all probes, it acts as a control to normalize signals between different locations that may have different numbers of probes due to variations in drop size in spotting DNA onto the array, and the like. The label is chosen to not interfere with the label on the amplicons. Each probe 16, 18 also contains, adjacent to the control region 22, an HPV unique sequence region 26, 26a, that will differ from probe to probe, as described below, so as to distinguish different genotypes of HPV. This unique sequence 26, 26a is intended to specifically hybridize with DNA from an E1 gene region amplicon 28 containing a separate label 30, preferably biotin, which is subsequently used to bind streptavidin-allophycocyanin. As shown below (see Table 5), the E1 probe sequences 26, 26a are similar when aligned in a multiple sequence alignment of HPV E1 genes. However, they are sufficiently different to hybridize under stringent conditions only with their cognate amplicon when a specific. HPV genotype is present in a sample, in which case it is recognized by primers described below to form the amplicon 28.

In use, a clinical sample suspected of containing HPV is processed for possible HPV DNA. The HPV DNA is hybridized/annealed to forward and reverse primers 34, 36, one of which contains the biotin label 30. A collection of different primers, sufficient to amplify all HPV types of interest (up to all known types, approximately 100 types), is added in this step. A large number of primers may be used without the usual problems of cross hybridization because the primers are all very similar in sequence and therefore are not likely to hybridize to each other. Furthermore, the primers may be simultaneously thermocycled, because they are designed to have similar melting and annealing temperatures. It is not necessary that the primers be unique to a single genotype, because the amplicon will be tested with a unique probe in the microarray. Thus, in the presence of HPV, the primers will result in an amplicons bearing the biotin label, which are then contacted with probes, 16, 18, etc. as described above.

Definitions and Abbreviations bp: base pair
DNA: Deoxyribonucleic acid
dNTP: Deoxynucleotide triphosphate EDTA: Ethylenediamine tetra acetic acid
HC: Hybrid Capture
HNSCC: Head and Neck squamous cell carcinomas
HPV: Human Papillomavirus
$MgCl_2$: Magnesium Chloride
NaCl: Sodium Chloride
PCR: Polymerase Chain Reaction
RNA: Ribonucleic acid
SDS: Sodium Dodecyl Sulfate
SSB: Single-stranded DNA binding protein
SSC: Saline-Sodium Citrate
SCC: Squamous Cell Carcinoma
SSPE: Saline-Sodium Phosphate EDTA buffer The term "percent identity" (% I) means the percentage of amino acids or nucleotides that occupy the same relative position when two amino acid sequences, or two nucleic acid sequences, are aligned.

The term "oligonucleotide" refers to short length single or double stranded sequences of deoxyribonucleotides linked via phosphodiester bonds. The oligonucleotides are chemically synthesized by known methods and purified, for example, on polyacrylamide gels.

The phrase "stringent conditions" refers to hybridization or wash conditions under which a nucleic acid, e.g., a sample nucleic acid or a probe will primarily hybridize to its target subsequence, typically in a complex mixture of nucleic acid, but to no other sequences in significant amounts. A positive signal (e.g., identification of a nucleic acid of the invention) is about 10 times background hybridization. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium).

Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

"E1" means the HPV E1 gene, generally located at about HPV nucleotides 4700-6000, but, more specifically, it is a gene encoding a protein, which, in its unmutated form, has two domains. The first domain binds to the origin and the other domain acts as a helicase. E1's DNA binding domain (E1 DBD) binds adjacent to E2 while it binds to its DBD. E1 DNA sequences are given at GenBank Accession numbers NC 001694, NC 001693, NC 001691, and elsewhere. Thus, a genotype of an HPV E1 sequence means an E1 sequence from a scientifically recognized genotype of HPV, such as defined for example in Vernon et al., "Comparison of Human Papillomavirus Detection and Typing by Cycle Sequencing, Line Blotting, and Hybrid Capture," *Journal of Clinical Microbiology*, February 2000, p. 651-655, Vol. 38, No. 2. AS is demonstrated below, the E1 sequence will have detectible sequence differences among the different genotypes.

The term "multiplexed" means that the present assays may be carried out with different reagents for different HPV genotypes simultaneously. That is, the primers are designed to be highly similar, so that they will have very little if any dimerization. In order to prevent self-hybridization, yet permit amplification of multiple, different HPV genotypes, the primers will preferably be 90% identical, or even 95% identical. They will be less than 100% identical, preferably 99-95% identical. The present multiplexing further includes the use of the present probes in simultaneous exposure to the amplified sample and any HPV in it, including multiple HPV genotypes. As an example, a Clustal W alignment (http://www.ebi.ac.uk/cgi-bin/clustalw) of the first 22 primer sequences shown in Table 4 results in al alignment of the sequences (which are 18-23 bases long) showing in general 2-3 positions of difference between the sequences and 9 positions of identity among all 10, yielding scores in the pairwise alignment consensus scores of all 22 sequences of 100 (for 7:8) to 70.

2. MATERIALS AND METHODS

Cell Lines and Clinical Samples

The DNA used in this study was isolated from eight cervical cell lines and 30 vulvar carcinoma biopsies. DNA extracts from cervical cell lines HeLa, SiHa, CaSki, C41, MS751, ME-180, SW756 and C33A were provided by Dr. Weng-Onn Lui (Stanford University School of Medicine, Calif.).

HPV Plasmids

HPV genomic DNA cloned in plasmids representing over 80 HPV types were kindly provided by Digene Corporate Research (Gaithersburg, Md.), Dr. de Villiers (German Cancer Research Center, Heidelberg, Germany), Dr. Favre (U. P. Génétique, Papillomavirus et Cancer Humain Institute Pasteur, France), Dr. Bruk (Albert Einstein College of Medicine of Yeshiva University, Bronx, N.Y.), Dr. Lancaster (School of Medicine, Wayne State University, Detroit, Mich.), Dr. Chao (National Cheng Kung University, Taiwan), Dr. Lindfors (Department of Medical Microbiology, University Hospital, Malmö, Sweden).

HPV Primers and Probes

A highly diverse region in the HPV genome was selected for the development of the HPV primers and probes used here. (Table 4 and 5) All HPV types that have been identified were aligned using the multi sequence alignment program ClustalW (www.ebi.ac.uk/clustalW). The selected region was within two consensus region of which the first was identified approximately 1200 bp of the commencement of the E1 region, and the second was 100 bp from the first consensus region. The reverse primers were biotinylated, allowing amplicons detection with streptavidin. Primers to the E1 and L1 region of the HPV genome were also designed (Table 4). For purposes of illustration, the "Linker A" region is bolded in the first sequence of Table 5. All sequences are given 5' to 3'.

TABLE 4

Sequence of HPV amplification primers

| HPV types | SEQ ID NO (F, R) | Sequence (Forward) | HPV types (Reverse) | Sequence |
|---|---|---|---|---|
| HPV-15, 37; 8080 | 218, 219 | BTCA TAT GCA TAT TGT ACC ATA GT | XX | CACCAGAATGGATAGT TAGAC |
| HPV-51, 82 | 9, 10 | BTCA AAT GCC CAT TGC ACC AT | HPV-3, 94 | CACGAGAGTGGATAGT TAGGC |
| HPV-51, 82 | 11, 12 | BTCA AAT GCC CAC TGA ATC AT | HPV-10 | CACCAGAGTGGATAGT CAGG |
| HPVa-81, 10 | 13, 14 | BTCA TAT GCC CAC TGC ACC A | HPV-28 | CACCAGAGTGGATAGT GAGAC |
| HPVb-81, 10 | 15, 16 | BTCG TAT GCC CAC TGC ACC | HPV-29, 72, 91 | CACCTGAATGGATAGT AAGAC |
| HPVa-28, 2A, 27 | 17, 18 | BGGT CAT ATG CAT ACT GTA CCA T | HPV-77, 61 | CTCCGGATTGGATAGTA AGAC |
| HPVb-28, 2A, 27 | 19, 20 | BTCG TAT GCA TAC TGT ACC AT | HPV-27, 90 | CACCAGAATGGATTGT AAGAC |
| HPV-3, 57 | 21, 22 | BTCA TAT GCG TAC TGC ACC AT | HPV-71, 2A, 87, 33, 58 | CACCAGAATGGATTGTT AGAC |
| HPV-90, 71, 54 | 23, 24 | BTCA TAT GCC CAT TGC ACC AT | HPV-57 | CACCAGAATGGATTGT GAGAC |
| HPVa-53, 41 | 25, 26 | BTCC AAT GCC CAC TGC AC | HPV-81, 89 | CACCAGAATGGATAGT AAGGC |
| HPVb-53, 41 | 27, 28 | BTCA AAT GCC CAC TGC AC | HPV-84, 86 | CACCAGACTGGATAGT ACGAC |
| HPVa-39, 35, 31, 96, 48, 67 | 29, 30 | BTCA AAT GCC CAT TGT ACC AT | HPV-6A, 6B, 11 | CACCAGAATGGATAAC ACGCC |
| HPVb-39, 35, 31, 96, 48, 67 | 31, 32 | BTCA TAT GCC CAT TGT ACC AT | HPV-44, 55 | CACCAGAATGGATAAC AAGGC |
| HPV-12 | 33, 34 | BTCG AAG GCC CAT TGG ACC | HPV-13 | CACCAGAATGGATAAA AAGGC |
| HPV-16 | 35, 36 | BTCG TAG GCC CAT TGT ACC AT | HPV-32, 59, 34, 73 | CACCCGAATGGATACA AAGAC |
| HPV-36 | 37, 38 | BTCA AAG GCC CAT TGT ACC AT | HPV-42, 18, 45, CAND85 | CACCTGAGTGGATACA AAGAC |
| HPV-21, 93 | 39, 40 | BTCA AAC GCC CAT TGA ACC AT | HPV-40, 7 | CACCGGAATGGATAGC TAAAC |
| HPV-24, 63, RTRX7, 8, 18, 70 | 41, 42 | BTCA AAT GCC CAT TGT ACC AT | HPV-39, 70 | CGCCAGAATGGATACA ACGAT |
| HPV-47, 25, 19, 45, 30 | 43, 44 | BTCA AAT GCC CAT TGA ACC AT | HPV-26, 69 | CACCAGAATGGATAGT ACGAC |
| HPV-5 | 45, 46 | BTGA AAT GCC CAT TGG ACC AT | HPV-51, 30 | CACCAGAATGGATTAC ACGAC |
| HPV-26 | 47, 48 | BTCG AAC GCC CAT TGC AC | HPV-82 | CACCAGAATGGATTAC AAGAC |
| HPV-29, 52, 69, 44, 55, 32, 42, 91 | 49, 50 | BTCA TAT GCC CAT TGC ACC AT | HPV-53, 56, 66 | CACCAGAATGGATACA AAGAC |
| HPV-40, 7, 13, 11, 6A, 6B | 51, 52 | BTCA TAT GCC CAC TGC ACC | HPV-67, 31 | CACCAGAATGGATAGA AAGAC |

TABLE 4-continued

Sequence of HPV amplification primers

| HPV types | SEQ ID NO (F, R) | Sequence (Forward) | HPV types (Reverse) | Sequence |
|---|---|---|---|---|
| HPV-14D, 56 | 53, 54 | BTCA AAT GCC CAC TGC ACC | HPV-16, 35 | CGCCAGAATGGATACAAAGAC |
| HPV-77, 50, 4 | 55, 56 | BTCG TAT GCC CAC TGT ACC | HPV-52 | GGTACAACCCCAGAATGGAT |
| HPV-65, 1A, 95 | 57, 58 | BTCA TAA GCC CAC TGA ACC AT | HPV-54 | GGTACAACCCCAGGATGG |
| HPV-CAN85, 59, 73 | 59, 60 | BTCA AAC GCC CAT TGT ATC AT | HPV-1A | GGTACAACTTTGGAGTGGAT |
| HPV-92, 94 | 61, 62 | BTCA TAT GCC CAC TGT ATC AT | HPV-4, 65, 95, 63, 38 | GGACAAACACCTGATTGGAT |
| HPV-17, 60, 9 | 63, 64 | BTCA TAA GCA AAT TGT ATC AT | HPV-14D, 20, 21, 36, 5, 47, 12, RTRX7, 8 | GGTCCATATCCTGATTGGAT |
| HPV-22, 75, 76, 49, 38, 58 | 65, 66 | BTCA TAA GCC CAT TGT ATC AT | HPV-60 | GGACCGTTTCCAGATTGGTT |
| HPV-23 | 67, 68 | BATC ATA AGC CCA TTG TAT CAT T | HPV-80, 15, 9, 22, 23, 96, 93 24, 17, 37, 48, 50 | GGAGAGTATCCTGAGTGGAT |
| HPV-34, 66 | 69, 70 | BTCA AAT GCC CAC TGT ACC AT | HPV-25, 19, 92 | GGCTCATATCCAGATTGGAT |
| HPV-33, 86, 84, 72, 61, 89 | 71, 72 | BTCA TAT GCC CAC TGT ACC AT | HPV-75, 76, 49 | GGAACCTATCCTGATTGGAT |
| HPV-83, 87 | 73 | BTCA TAC GCC CAC TGC ACA | | |

Note:
B is biotin

TABLE 5

45 bp sequence (complete sequence) of HPV probes

| HPV types | Sequence | HPV types | Sequence |
|---|---|---|---|
| HPV-1A | TCTGAGCCACTTGGACTGAGAACCCTTATTAATCATCAGTTAGAT (SEQ ID NO: 74) | HPV-47 | TTTTTTTCTGAGCCACTTGGACTGAGATTTTGGGCCATAAGAGTG (SEQ ID NO: 75) |
| HPV-2A | TTTTTTTCTGAGCCACTTGGACTGAGGAACAGTTCAGACTGTCAG (SEQ ID NO: 76) | HPV-48 | TTTTCTGAGCCACTTGGACTGAGGTAGAACATCAGTTAGCTTCAG (SEQ ID NO: 77) |
| HPV-3 | TTTTTTCTGAGCCACTTGGACTGAGCAGTTCAGTCTGTCAGAATG (SEQ ID NO: 78) | HPV-49 | TTTTCTGAGCCACTTGGACTGAGCAATTTGACCTTTCTGAAATGA (SEQ ID NO: 79) |
| HPV-4 | TTTTTTTCTGAGCCACTTGGACTGAGCTGCAGAGACTTTTGAGTT (SEQ ID NO: 80) | HPV-50 | TTTTCTGAGCCACTTGGACTGAGTAAATCATCAGCTAGCAACTG (SEQ ID NO: 81) |
| HPV-5 | TTTTCTGAGCCACTTGGACTGAGTTGCCCAACAAACTATATTAGG (SEQ ID NO: 82) | HPV-51 | TTTTCTGAGCCACTTGGACTGAGAAACGCAACTACAACATAGTTT (SEQ ID NO: 83) |

TABLE 5-continued

45 bp sequence (complete sequence) of HPV probes

| HPV types | Sequence | HPV types | Sequence |
|---|---|---|---|
| HPV-6A | TTTTTCTGAGCCACTTGGACTGA GACTGTTATTGAACATGGGTTG (SEQ ID NO: 84) | HPV-52 | TTTCTGAGCCACTTGGACTGAGACAATAGCATATTCGATTTTGGA (SEQ ID NO: 85) |
| HPV-6B | TTTTTTTCTGAGCCACTTGGACT GAGCAGTTATTGAACACGGGTT (SEQ ID NO: 86) | HPV-53 | TTTTCTGAGCCACTTGGACTGAGACAGTTACAACATAGCTTTGAG (SEQ ID NO: 87) |
| HPV-8 | TTTTCTGAGCCACTTGGACTGAG AGCACCTTTGATTTTTCTGTAA (SEQ ID NO: 88) | HPV-54 | TCTGAGCCACTTGGACTGAGTGTAATTGAATATAGCTTAGCAGAC (SEQ ID NO: 89) |
| HPV-9 | TTTTCTGAGCCACTTGGACTGAG CACTAATTAATCACCAATCTGC (SEQ ID NO: 90) | HPV-55 | TTTTTTTCTGAGCCACTTGGACTGAGCTTGGTGACAACCAATTCA (SEQ ID NO: 91) |
| HPV-10 | TTTTTTCTGAGCCACTTGGACTG AGGTTTAGCCTTTCAGAGATGG (SEQ ID NO: 92) | HPV-56 | TTCTGAGCCACTTGGACTGAGCAGTTTACAGGATAGTCAATTTGA (SEQ ID NO: 93) |
| HPV-11 | TTTTCTGAGCCACTTGGACTGAG CAGACCGTTATTGAACATAGTT (SEQ ID NO: 94) | HPV-57 | TTTCTGAGCCACTTGGACTGAGAGATGAGCAGTTCAAATTATCTG (SEQ ID NO: 95) |
| HPV-12 | TTTTTTCTGAGCCACTTGGACTG AGAATTTTGGGCCATCAAAATG (SEQ ID NO: 96) | HPV-58 | TTTTTCTGAGCCACTTGGACTGAGCAGTGTTACAGCATAGCTTTA (SEQ ID NO: 97) |
| HPV-13 | TTTTCTGAGCCACTTGGACTGAG TGGACTTGCAGATAATCAATTT (SEQ ID NO: 98) | HPV-59 | TTTTTTCTGAGCCACTTGGACTGAGGAGTTGATGATAGCGTGTTT (SEQ ID NO: 99) |
| HPV-14D | TTTTTTCTGAGCCACTTGGACTG AGCAGAAGCAAATGCATTTGAT (SEQ ID NO: 100) | HPV-60 | TTTTTCTGAGCCACTTGGACTGAGCTATGTTAGACCATGAATCCG (SEQ ID NO: 101) |
| HPV-15 | TTTTCTGAGCCACTTGGACTGAG CAATGATAAATCACCAAACAGC (SEQ ID NO: 102) | HPV-61 | TTTTTTTCTGAGCCACTTGGACTGAGAATGCAAGAAGCACAGTTT (SEQ ID NO: 103) |
| HPV-16 | TCTGAGCCACTTGGACTGAGGAT TGTACATTTGAATTATCACAGA (SEQ ID NO: 104) | HPV-63 | TTTCTGAGCCACTTGGACTGAGCATTGTTGAATCATCAATTAGCA (SEQ ID NO: 105) |
| HPV-17 | TTCTGAGCCACTTGGACTGAGCT ATGATTAATCATCAAACAGCAC (SEQ ID NO: 106) | HPV-65 | TTTTTCTGAGCCACTTGGACTGAGAAACCTTAGTAAGCCATCAAG (SEQ ID NO: 107) |
| HPV-18 | TCTGAGCCACTTGGACTGAGGGA ATAGATGATAGCAATTTTGATT (SEQ ID NO: 108) | HPV-66 | TTCTGAGCCACTTGGACTGAGCAGTTTACAAGACAATCAATTTGA (SEQ ID NO: 109) |
| HPV-19 | TTTTCTGAGCCACTTGGACTGAG AAGCAAGTAGTTTTGATTTGTC (SEQ ID NO: 110) | HPV-67 | TTTTTCTGAGCCACTTGGACTGAGGGTACTGCAACATAGTTTTGA (SEQ ID NO: 111) |
| HPV-20 | TTTTTTCTGAGCCACTTGGACTG AGCTATTGTTGGTCATCAGAGC (SEQ ID NO: 112) | HPV-69 | TCTGAGCCACTTGGACTGAGCACAATTAGAACATAGTTTTGAAGA (SEQ ID NO: 113) |
| HPV-21 | TTTTTTTCTGAGCCACTTGGACT GAGGAAGCCAGTGCATTTGATA (SEQ ID NO: 114) | HPV-70 | TTTCTGAGCCACTTGGACTGAGAACAGTAATACAGCATGGAATAG (SEQ ID NO: 115) |
| HPV-22 | TTTTTTCTGAGCCACTTGGACTG AGTGTACAATTTGACCTGTCTG (SEQ ID NO: 116) | HPV-71 | TTTTTTTTCTGAGCCACTTGGACTGAGAAACTGTGGTAGGACACA (SEQ ID NO: 117) |
| HPV-23 | TTCTGAGCCACTTGGACTGAGAT ACAATTTGATTTGTCTCGTATG (SEQ ID NO: 118) | HPV-72 | TTTTTCTGAGCCACTTGGACTGAGGACACAGTTTAGCCTTTCTAC (SEQ ID NO: 119) |

TABLE 5-continued

45 bp sequence (complete sequence) of HPV probes

| HPV types | Sequence | HPV types | Sequence |
|---|---|---|---|
| HPV-24 | TCTGAGCCACTTGGACTGAGTGG ATTATAGAACAAACACTGATAG (SEQ ID NO: 120) | HPV-73 | TTTTTCTGAGCCACTTGGACTGAGGTTAGTGCAGCATAGTTTAGA (SEQ ID NO: 121) |
| HPV-25 | TTTTCTGAGCCACTTGGACTGAG GCTAGTACATTTGATCTATCGG (SEQ ID NO: 122) | HPV-75 | TTTTCTGAGCCACTTGGACTGAGGCAATTTGATTTGTCTCAAATG (SEQ ID NO: 123) |
| HPV-26 | TCTGAGCCACTTGGACTGAGTTG ATGATGCTACATTTGATTTATC (SEQ ID NO: 124) | HPV-76 | TTTCTGAGCCACTTGGACTGAGTGCAATTTGACTTATCTGAAATG (SEQ ID NO: 125) |
| HPV-27 | TTTTTCTGAGCCACTTGGACTGA GTAGTATGGAAGATGAGCAGTT (SEQ ID NO: 126) | HPV-77 | TTTTTTTCTGAGCCACTTGGACTGAGATTGTGGGACATGCTTTAG (SEQ ID NO: 127) |
| HPV-28 | TTTTTTTCTGAGCCACTTGGACT GAGGCACAGTTTAGTCTGTCG (SEQ ID NO: 128) | HPV-80 | TTTTTCTGAGCCACTTGGACTGAGACAATGATAAGCCATCATACAG (SEQ ID NO: 129) |
| HPV-29 | TTTTTTTCTGAGCCACTTGGACT GAGGTAGGTCACGCATTACAAG (SEQ ID NO: 130) | HPV-81 | TTTTTTTCTGAGCCACTTGGACTGAGTGCAGGAAACACAGTTTAG (SEQ ID NO: 131) |
| HPV-30 | TTTTTTTCTGAGCCACTTGGACT GAGGTTTTCAGGACTGCCAATT (SEQ ID NO: 132) | HPV-82 | TTTTTCTGAGCCACTTGGACTGAGTTTTGATGATAGCACGTTTGAA (SEQ ID NO: 133) |
| HPV-31 | TTTTTTCTGAGCCACTTGGACTG AGCACAACATTTGATTTGTCCC (SEQ ID NO: 134) | HPV-83 | TTTCTGAGCCACTTGGACTGAGAGAAGCCCAATTTAGTTTATCAA (SEQ ID NO: 135) |
| HPV-32 | TTTTTTTCTGAGCCACTTGGACT GAGTTGCTTTGCAGATACACAG (SEQ ID NO: 136) | HPV-84 | TTTTTTTCTGAGCCACTTGGACTGAGGACAAACTGTAATTGGGCA (SEQ ID NO: 137) |
| HPV-33 | TCTGAGCCACTTGGACTGAGACT GTTTTACAACATAGCTTTAATG (SEQ ID NO: 138) | HPV-CAND85 | TTCTGAGCCACTTGGACTGAGCATGGTATAGATGACAGTGTATTT (SEQ ID NO: 139) |
| HPV-34 | TTTTTTTCTGAGCCACTTGGACT GAGGTAGTACAGCACAGCTTAG (SEQ ID NO: 140) | HPV-86 | TTTTTTCTGAGCCACTTGGACTGAGCACAATTTAGCCTATCTGTGT (SEQ ID NO: 141) |
| HPV-35 | TTTCTGAGCCACTTGGACTGAGA TGCAATATTTGACCTATCTGAA (SEQ ID NO: 142) | HPV-87 | TTCTGAGCCACTTGGACTGAGACACAATTTAGCTTATCAGTACTG (SEQ ID NO: 143) |
| HPV-36 | TTTTTTTCTGAGCCACTTGGACT GAGAATAATGCTGAAGCAAGCA (SEQ ID NO: 144) | HPV-89 | TTTTTTTCTGAGCCACTTGGACTGAGCAATGAAGGAAACCCAGTT (SEQ ID NO: 145) |
| HPV-37 | TTTTTTCTGAGCCACTTGGACTG AGACCATGATCAATCACCAATC (SEQ ID NO: 146) | HPV-90 | TTTTTTTCTGAGCCACTTGGACTGAGGGCACAGTCTAGAAGAATG (SEQ ID NO: 147) |
| HPV-38 | TTTTTCTGAGCCACTTGGACTGA GCAATGATACAGCATCAAACTG (SEQ ID NO: 148) | HPV-91 | TTTTTCTGAGCCACTTGGACTGAGCAGTGTTAGAACACAGTTTTG (SEQ ID NO: 149) |
| HPV-39 | TCTGAGCCACTTGGACTGAGCTG TTATACAACATGGAATAGATGA (SEQ ID NO: 150) | HPV-92 | TTTTTTCTGAGCCACTTGGACTGAGCATTGCTTTCTCATCAGGAA (SEQ ID NO: 151) |
| HPV-40 | TTTTTCTGAGCCACTTGGACTGA GTATGTTAGAACACAGCTTTGC (SEQ ID NO: 152) | HPV-93 | TTTTTCTGAGCCACTTGGACTGAGGGCAACATTTGATATGTCAAC (SEQ ID NO: 153) |
| HPV-41 | TTTTTCTGAGCCACTTGGACTGA GAAACCTTAGTAAGCCATCMG (SEQ ID NO: 154) | HPV-94 | TTTTTCTGAGCCACTTGGACTGAGAGTTTACCCTTTCAGAGATGA (SEQ ID NO: 155) |

TABLE 5-continued 45 bp sequence (complete sequence) of HPV probes

| HPV types | Sequence | HPV types | Sequence |
|---|---|---|---|
| HPV-42 | TTTTTTTCTGAGCCACTTGGACTGAGTTTTGCAGATGCCCAATTT (SEQ ID NO: 156) | HPV-95 | TTTTTTCTGAGCCACTTGGACTGAGCTAAGCAGACAATAGTGAGC (SEQ ID NO: 157) |
| HPV-44 | TTCTGAGCCACTTGGACTGAGTTGCAGACAACCAATTTAAATTAG (SEQ ID NO: 158) | HPV-96 | TTTTTTCTGAGCCACTTGGACTGAGCGATGATTAGTCACCATGAG (SEQ ID NO: 159) |
| HPV-45 | TTTCTGAGCCACTTGGACTGAGATTCAACATGGTATTGACGATAG (SEQ ID NO: 160) | RTRX7 | TTTTTTTTCTGAGCCACTTGGACTGAGGTACTTGGCCACCAAAAT (SEQ ID NO: 161) |

TABLE 6

OVERVIEW OF E1 AND L1 HPV PRIMERS USED IN VALIDATION TESTS

| HPV Type | Sequence (Forward) | Sequence (Reverse) |
|---|---|---|
| HPV-16 | AGAGCCTCCAAAATTGCGTA SEQ ID NO: 162 | TGCATTACTATTAGTGTCTGCCAAT SEQ ID NO: 163 |
| HPV-18 | AACCACCAAAATTGCGAAGT SEQ ID NO: 164 | GCTGCATTGCTGTTGCTG SEQ ID NO: 165 |
| HPV-29 | CCATATGTTAATTGAGCCACCT SEQ ID NO: 166 | CATCTGCTATCAATGCATACTCG SEQ ID NO: 167 |
| HPV-31 | ATTCAGCCACCCAAATTACG SEQ ID NO: 168 | TCACTGTCAGCTAATTGTGCAT SEQ ID NO: 169 |
| HPV-44 | AATTGAACCTCCTAAAATACAAAGC SEQ ID NO: 170 | TTGGCATCTATATCTGCACGTT SEQ ID NO: 171 |
| HPV-66 | AAGCACCAAAACTACGAAGTCC SEQ ID NO: 172 | TCCACAATCCTTTACATATTTTGC SEQ ID NO: 173 |
| HPV-16 | GCATTTGTTGGGGTAACCA SEQ ID NO: 174 | CCAAAATTCCAGTCCTCCAA SEQ ID NO: 175 |
| HPV-18 | TCCCTCTCCAAGTGGCTCTA SEQ ID NO: 176 | GGACATAACATCTGCAGTTAAAGTAA SEQ ID NO: 177 |
| HPV-29 | TAACAACGGGCGAGAAACTC SEQ ID NO: 178 | GGAAGGTGGCAATGTCAATC SEQ ID NO: 179 |
| HPV-31 | ACGTGCTCAGGGACACAATA SEQ ID NO: 180 | ACTGTGAATATATGTCATTATGTCTGC SEQ ID NO: 181 |
| HPV-44 | ACGTTTCCCAGGATCTGGTT SEQ ID NO: 182 | TTCCACTGTTCTAAAATACCAGCA SEQ ID NO: 183 |
| HPV-66 | CCCTCCTCCCAGTTCTGTAT SEQ ID NO: 184 | GCAGTTAAGGTTATTTTACAAAGTTGA SEQ ID NO: 185 |

Verification of HPV Primers

The present HPV primers were tested with polymerase chain reaction (PCR) on HPV plasmids (HPV-15, -16, -18, -19, -20, -21, -22, -28, -29, -32, -34, -35, -45, -50, -54, -56, -66, -67, -90, and 96). The 50 µl reaction mixes contained 1 µl of HPV plasmids, 10×PCR buffer, Ampli Taq Gold™ DNA polymerase [5 U/µl], 2.5 mM MgCl$_2$ (Applied Biosystems, Foster City, Calif.), 0.2 mM dNTPs (Sigma-Aldrich, St. Louis, Mo.), pool of biotin reverse HPV primers (5 pmol) and pool of non-biotin forward HPV primers (5 pmol). The PCR cycles contained an initial step of denaturing at 94° C. for 45 seconds, followed by annealing at 50° C. for 45 seconds and elongation for 45 seconds at 72° C. 30 cycles of amplification were performed. The PCR-products were subsequently loaded on a 2.5% agarose (Sigma-Aldrich, St. Louis, Mo.) gel, which was run for approximately 45 minutes at 100V and visualized with ethidium bromide.

Designed E1 and L1 amplification primers for HPV types 16, 18, 29, 31, 44, and 66 were validated through PCR using HPV plasmids for these specific HPV types. The 50 µl reaction mixes contained 0.5 µl of HPV plasmids, 10×PCR buffer, AmpliTaq Gold™ DNA polymerase [5 U/µl], 2.5 mM MgCl$_2$ (Applied Biosystems, Foster City, Calif.), 0.2 mM dNTPs (Sigma-Aldrich, St. Louis, Mo.), and 5 pmol primer (Integrated DNA technologies (IDT), Coralville, Iowa). The PCR cycles contained an initial step of denaturing at 94° C. for one minute, followed by annealing at 54° C. for 45 seconds and elongation for 45 seconds at 72° C. 35 cycles of amplification were performed. The PCR-products were subsequently loaded on a 2.5% agarose (Sigma-Aldrich, St. Louis, Mo.) gel, which was run for approximately 45 minutes at 100V and visualized with ethidium bromide.

Pyrosequencing

To further verify the HPV primers, the amplicons were sequenced using pyrosequencing. Pyrosequencing is a known method, further described in U.S. Pat. Nos. 6,210,891 and 6,258,568, hereby incorporated by reference as giving such descriptions. Pyrosequencing is a DNA sequencing technique that uses bioluminometric pyrophosphate (PPi) monitoring to establish DNA sequence. The principal of this method is sequencing by synthesis, referring to the synthesis of a complementary DNA strand from an immobilized single stranded DNA template. A cascade of four enzymatic reactions is applied in this technique, starting with the production of PPi as a result of nucleotide incorporation by DNA polymerase (Ronaghi M, 1998; Fakhrai-Rad H., 2002. In each reaction cycle one of the four nucleotides dNTP (dATP, dCTP, dGTP, dTTP) is dispensed into the reaction mixture. If complementary to the DNA template the nucleotide is incorporated by DNA polymerase resulting in the production of PPi. The PPi produced, is converted to ATP by ATP-sulfurylase, which is subsequently used as an energy source by luciferase to catalyze the oxidation reaction of luciferin generating light (Gharizadeh B., 2001; Ronaghi M., 1998). Light sensitive instruments such as a CCD camera monitor the light that is generated. The amount of light that is generated and detected is proportional to the amount of ATP that is generated, which is also proportional to the amount of nucleotide that is incorporated which lead to PPi release. Nucleotides that are not incorporated and excessive ATP present in the reaction are degraded by apyrase (Pourmand N., 2002; Ronaghi M., 1998).

The reaction mixes containing 7 µl amplicons, binding/washing buffer [10 mM Tris-HCl (pH 7.6), 2M NaCl, 1 mM EDTA, 0.1% Tween 20], streptavidin sepharose™ beads in 20% ethanol (Amersham Biosciences) and water were shaken for at least 5 minutes at 1400 rpm. Using the Vacuum Prep Work table (Biotage, Uppsala, Sweden), amplicons bound to beads were subsequently attached through suction to the filtered tip of the vacuum prep tool 2 (in house). Followed by rinsing in 70% ethanol for 5 seconds, denaturing of double-strand DNA bond by placing and suction of 0.2 M NaOH for 5 seconds and finally washing unattached single-stranded DNA with 0.1M Tris-acetate buffer (pH 7.6). The DNA strands attached to the vacuum prep tool 2 were placed in PSQ HS plate (Biotage, Uppsala, Sweden) containing 10 pmol of the non-biotinylated HPV primer and annealing buffer [20 mM Tris-acetate (pH 7.6), 5 mM MgCl$_2$]. Enzyme, substrate, and single-stranded DNA binding protein pyrosequencing™ Grade (SSB) (all from Biotage, Uppsala Sweden) were added to the reaction mix and a sequencing run of 10 ACGT-cycles using the PSQ HS 96 system (Biotage, Uppsala, Sweden) was performed. The obtained sequences were analyzed with the Basic Local Alignment Search Tool (BLAST) database search.

HPV DNA Microarray

The microarrays were spotted with an OmniGrid™ (GeneMachines™, San Carlos, Calif.) instrument in conjunction with the Gridder 2.0.5 software. The probes were spotted onto Amine-Binding Codelink™ Activated slides (Amersham Biosciences, Piscataway, N.J.) in a mixture containing 20 µm HPV probe, 80 µm Poly T amino acid and 1× printing buffer [300 mM Sodium phosphate (pH 8.5), 0.001% Sodium Dodecyl Sulfate (SDS)]. The probe mixtures were dried and resuspended in 12 µl water. Each probe was printed four times on the slides with a spots spacing of 300 microns. Additional positive controls were also spotted. The printed slides were stored in a NaCl chamber overnight at room temperature and subsequently blocked with pre-warmed (50° C.) blocking buffer [0.1 M Tris, 50 mM Ethanolamine (pH 9.0)] for 30 minutes. The slides were then rinsed twice with distilled water, incubated for an initial 5 minutes in pre-warmed at 50° C. 4× Saline-Sodium Citrate (SSC), 0.1% SDS, followed by an additional 25 minutes in pre-warmed at 50° C. 4×SSC, 0.1% SDS. The slides were then rinsed in distilled water, centrifuged for 3 minutes at 800 rpm and stored.

DNA Microarray Hybridization Assays

The microarray probes were tested by hybridization with the amplicons obtained through the testing of the HPV primers. Following instructions by manufacturer the PCR-products were purified with the Qiaquick PCR purification kit (Qiagen Sciences, Maryland). Four pools of HPV plasmids amplicons of equal volume were made. (Pool one: HPV-15, -16, -18, -19, and -20; pool two: HPV-15, -16, -18, -19, -20, -21, -22, -28, -29, and 32; pool three: HPV-15, -16, -18, -19, -20, -21, -22, -28, -29, -32, -34, -35, -45, -50, and 54; and pool four: HPV-15, -16, -18, -19, -20, -21, -22, -28, -29, -32, -34, -35, -45, -50 -54, -56, -66, -67, -90, and 96). The pools of HPV plasmids were mixed with hybridization buffer [100 mM MES, 1M (Na$^+$), 20 mM EDTA, 0.01% Tween 20] and heated for 5 minutes at 95° C. The samples were placed directly on ice, 3 µl 50× Denhardt's (Sigma-Aldrich, St. Louis, Mo.), and 2.5 pmol Linker A binding sequence (TCTGAGC CACTTG-GACTGAG SEQ ID NO: 186) was added to the samples.

The chips were hybridized overnight in 50° C. water bath, followed by two washing steps with 6× Saline-Sodium Phosphate EDTA buffer (SSPE) (Invitrogen, Carlsbad, Calif.), 0.1% Tween 20 for 3 minutes at 50° C. and one washing step with 6×SSPE, 0.1% Tween 20 for 3 minutes at room temperature. The chips were centrifuged for 3 minutes at 1000 rpm and labeled with 6×SSPE, 0.01% Tween 20, 1× Denhardt's, 0.0017 µg/µl streptavidin, R-phycoerythrin conjugate (SAPE) (Molecular Probes, Inc, Eugene, Oreg.) for 10 minutes in 50° C. water bath. After labeling, the chips were washed according to the mentioned method above and scanned with Genepix™ 4000A (Axon Instruments, Union City, Calif.). The data was analyzed with GenePix® Pro 6.0 (Axon Instruments, Union City, Calif.).

The chip microarray was further tested with DNA extracted from cervical cell lines and clinical samples. DNA extracted from the cell lines were amplified using GP5$^+$ and GP6$^+$ primers under the following PCR conditions. An initial step of denaturation at 95° C. for 1 minute, followed by annealing at 48° C. for 45 seconds. The PCR cycle was repeated 35 times. Pyrosequencing was then performed as described. In a 50 µl PCR reaction containing 1 µl DNA, 10×PCR buffer, Ampli Taq Gold™ DNA polymerase [5 U/µl], 2.5 mM MgCl$_2$ (Applied Biosystems, Foster City, Calif.), 0.2 mM dNTPs (Sigma-Aldrich, St. Louis, Mo.), 5 pmol biotin reverse HPV primer (pool) and 5 pmol non-biotin forward HPV primer (pool). The 35 amplification cycles were performed under the following conditions: denaturation for 45 seconds at 94° C., followed by annealing for 45 seconds at 50° C. The PCR-product was purified with the Qiaquick PCR purification kit (Qiagen Sciences, Maryland) and hybridized to the microarray chip.

Amplification of the clinical samples was carried out in two steps. The initial touchdown PCR mix contained 1 μl DNA, 10×PCR buffer, Ampli Taq Gold™ DNA polymerase [5 U/μl], 2.5 mM MgCl$_2$ (Applied Biosystems, Foster City, Calif.), 0.2 mM dNTPs (Sigma-Aldrich, St. Louis, Mo.) and 5 pmol PGMY09/11 primers. The PCR conditions were as follows: an initial 14 cycles of denaturation for 1 minute at 95° C., followed by annealing for 1 minute starting at 58° C. and decreasing 0.5° C. each cycle to 51° C. and subsequently elongation for 1 minute at 72° C. An additional 23 cycles were carried out for 1 minute at 95° C., 1 minute at 50° C. and finally 1 minute at 72° C. In the second step, 5 μl PCR product of the touchdown PCR was amplified with 10 pmol GP5$^+$ and GP6$^+$ for 35 cycles at 95° C. for 1 minute and 45 seconds at 48° C. The positive samples were then sequenced by pyrosequencing using the GP5$^+$ primer as the sequencing primer in addition to three pools of multi-sequencing primers (Gharizadeh B. et al., 2003) (pool 1: HPV-16, -31, -59 and 39, pool 2: HPV-18, -33, -52 and 56 and pool 3: HPV-45, -35, -58 and 51). All 30 samples were subsequently amplified with the pool of HPV primers using the following PCR conditions: denaturation for 45 seconds at 94° C., followed by annealing for 45 seconds at 50° C. for 35 amplification cycles. The sequenced samples were hybridized individually to the chip as well as in a pool of all 30 samples.

2.8 Amplification Treatment of Clinical Samples

The designed E1 and L1 amplification primers were used to amplify the 30 clinical samples. The same PCR condition described in the verification section was used. The PCR products were run on gel for approximately 45 minutes at 100V and visualized with ethidium bromide. To verify the result, 5 samples positive for E1 region and 3 samples positive for the L1 region were selected and cloned with the TOPO TA Cloninge® Kit for Sequencing (Invitrogen, Carlsbad, Calif.). Using the manufacturer's instruction the PCR products were inserted into pCR® 4-TOPO® vector which were subsequently transformed into TOP10 *E. coli* cells and grown overnight at 37° C. Five colonies were picked from each plate and a PCR using M13 primer provided by the kit amplified the target DNA under the following PCR conditions: denaturation at 94° C. for 45 seconds, followed by annealing at 53° C. for 45 seconds and elongation for 45 seconds at 72° C. The amplification cycles were repeated 35 times. The amplicons were then used to perform Sanger sequencing and analyzed with Sequencher™ 4.1.2 software.

3. EXAMPLES 3.1. Validation HPV Primers

To validate the HPV primers, a PCR reaction was carried out in conjunction with HPV plasmids. Each HPV type-specific primer was selected to amplify its plasmid counterpart. An electrophoresis was performed and the results obtained showed positive bands at approximately 100 bp for HPV plasmids: HPV-15, -16, -18, -19, -20, -21, -22, -28, -29, -32, -34, -35, -45, -50, -54, -66, -67, -90 and 96 with the exception of HPV-54 (data not shown).

To further test the primers, pyrosequencing was performed with the amplicons obtained through the PCR reaction. The non-biotinylated primers were used to carry out the sequencing reaction and the data was analyzed with BLAST. The attained sequences matched the HPV plasmid types that were selected (Table 7). Correct sequences for HPV-15, -16, -18, -19, -20, -21, -22, -28, -29, -32, -34, -35, -45, -50, -54, -56, -66, -67, -90 and 96 were obtained (pyrograms are not shown).

TABLE 7

Results pyrosequencing of HPV plasmids with HPV primers

| Primers | HPV-plasmid | Sequence (position) | HPV type |
|---|---|---|---|
| HPV-15, 37, 80 HPV-80, 15, 9, 22, 23, 96, 93, 24, 17, 37, 48, 50 | HPV-15 | AATGACACAAACAATGA (1771-1790) SEQ ID NO: 187 | HPV-15 |
| HPV-16 HPV-16, 35 | HPV-16 | AAACAGTATTACAACAT (1892-1908) SEQ ID NO: 188 | HPV-16 |
| HPV-24, 63, RTRX7, 8, 18, 70 HPV-42, 18, 45, CAND85 | HPV-18 | TTACTATTATACAAACA (1962-1986) SEQ ID NO: 189 | HPV-18 |
| HPV-47, 25, 19, 45, 30 HPV-25, 19, 92 | HPV-19 | AGCACAACAAACAATAT (1866-1882) SEQ ID NO: 190 | HPV-19 |
| HPV-20 HPV-14D, 20, 21, 36, 5, 47, 12, RTRX7, 8 | HPV-20 | GCACAGCAAACTATTCT (1877-1896) SEQ ID NO: 191 | HPV-20 |
| HPV-21, 93 HPV-14D, 20, 21, 36, 5, 47, 12, RTRX7, 8 | HPV-21 | TGCCCAGCAAACAATTG (1876-1892) SEQ ID NO: 192 | HPV-21 |
| HPV-22, 75, 76, 49, 38, 58 HPV-80, 15, 9, 22, 23, 96, 93, 24, 17, 37, 48, 50 | HPV-22 | TATAGACACAGAGTATG SEQ ID NO: 193 | HPV-22 |
| HPVa-28, 2A, 27 HPV-28 | HPV-28 | AAACGATGGTTGGACAT (1854-1870) SEQ ID NO: 194 | HPV-28 |
| HPV-29, 52, 69, 44, 55, 32, 42, 91 HPV-29, 72, 91 | HPV-29 | AGACAAATGGTAGGTCA (1867-1888) SEQ ID NO: 195 | HPV-29 |
| HPV-29, 52, 69, 44, 55, 32, 42, 91 HPV-32, 59, 34, 73 | HPV-32 | AAACAATTGTAGAACATT (1856-1877) SEQ ID NO: 196 | HPV-32 |
| HPV-34, 66 HPV-32, 59, 34, 73 | HPV-34 | AAACAGTAGTACAGCACA (1872-1896) SEQ ID NO: 197 | HPV-34 |
| HPVa-39, 35, 31, 96, 48, 67 HPV-16, 35 | HPV-35 | TGCACAACAGACTATATT (1839-1860) SEQ ID NO: 198 | HPV-35 |
| HPV-47, 25, 19, 45, 30 HPV-42, 18, 45, CAND85 | HPV-45 | TGACAAATTATTCCAAA SEQ ID NO: 199 | HPV-45 |
| HPV-77, 50, 4 HPV-80, 15, 9, | HPV-50 | AGCACACATACTGTTAT (1654-1674) | HPV-50 |

TABLE 7-continued

Results pyrosequencing of HPV plasmids with HPV primers

| Primers | HPV-plasmid | Sequence (position) | HPV type |
|---|---|---|---|
| 22, 23, 96, 93, 24, 27, 37, 48, 50 | | | SEQ ID NO: 200 |
| HPV-90, 71, 54 HPV-54 | HPV-54 | GCTGGCCAGACAAACTG (1793-1809) SEQ ID NO: 201 | HPV-54 |
| HPV-34, 66 HPV-53, 56, 66 | HPV-66 | AGACAACAAATTGCAAA (SEQ ID NO: 202) | HPV-66 |
| HPVa-39, 35, 31, 96, 48, 67 HPV-67, 31 | HPV-67 | TAACGGTACTGCAACAT (1857-1873) SEQ ID NO: 203 | HPV-67 |
| HPV-90, 71, 54 HPV-27, 90 | HPV-90 | AAACAGTTGTGGGCACA (1743-1771) SEQ ID NO: 204 | HPV-90 |
| HPVa-39, 35, 31, 96, 48, 67 HPV-80, 15, 9, 22, 23, 96, 93, 24, 17, 37, 48, 50 | HPV-96 | TGTTCAGCAAACGATGAT (1945-1962) SEQ ID NO: 205 | HPV-96 |

3.2. Control Experiments for Microarray

To test the HPV chip microarray, pools of HPV plasmids were made and hybridized to the chip and a positive signal could be seen for the respective HPV type. However, additional HPV types could also be detected and a number of HPV-types could not be detected (Table 8). For microarray chips hybridized a positive signal was detected for most of the HPV types hybridized to the chip with the exception of HPV-20, -45, -54 that were also in the pools. Additional HPV types were also detected on all of the chips.

TABLE 8

Results of Hybridization assay with pool HPV Plasmids

| | Positive signal | Additional positive signal | Negative signal |
|---|---|---|---|
| Pool one: | HPV-15, -16, -18 and 19 | HPV-33 and 67 | HPV-20 |
| Pool two: | HPV-15, -16, -18, -19, -21, -22, -28, -29 and 32 | HPV-31, -39, -67, -81 and 90 | HPV-20 |
| Pool three | HPV-15, -16, -18, -19, -21, -22, -28, -29, -32, -34, -35, -50 and 56 | HPV-31, -39, -49, -58, -67, -76, -81 and 90 | HPV-20, -45, -54 |
| Pool four: | HPV-15, -16, -18, -19, -21, -22, -28, -29, -32, -34, -35, -50, -56, -66, -67, -90, -96 | HPV-31, -39, -49, -81 | HPV-20, -45, -54 |

3.3. HPV Detection and Typing for Cervical Cancer Cell Lines

The application of the HPV chip microarray was further tested with cervical cell lines. DNA extracted from the cell lines was first amplified by the general primers GP5+ and GP6+ and subsequently sequenced with pyrosequencing. The DNA was then amplified with the pool of HPV primers and hybridized to the chip. The results were compared and additional HPV types could be detected with the chip in comparison with pyrosequencing. With pyrosequencing a sequence signal for HPV-16 (-ACGCAGTACAAAT-) SEQ ID NO: 206 could be detected for the cell lines CaSki SiHa, and ME-180 (data not shown), whereas a sequence signal for HPV-18 (-TCGCAGTACCAATTT-) SEQ ID NO: 207 was detected in cell lines C41 and SW765 (data not shown). A clear HPV sequence signal for the HeLa and MS751 cell lines could not be detected. An overview of pyrosequencing results is given in Table 9. As for the chip, a positive signal for HPV-16 was detected for SiHa, ME-180, and CaSki cell lines. In addition to HPV-16, HPV-31 was also detected for SiHa. Positive signal for HPV-18 was detected for C41, while HPV-18 and HPV-39 were positively detected for SW756. No signal was detected for C33A, which is HPV negative and the cell lines HeLa and MS751.

Representative results are illustrated in FIG. 2. In FIG. 2, each sample is present in 4 replicate spots. A row of red spots (●) represents a control for staining, with no probe hybridization. The red signal is provided by phycoerythrin. The green spots (○) represent genotypes where only Linker—A targeted sequences bound. The green color is from Cy3 dye. The yellow spots (Δ) show binding of both red and green, indicating that target sequences from the genotype in question are present and hybridized to the corresponding probe. Representative arrays from cell lines C33A, SW765 and ME-180 are shown. An overview of the chip hybridization results is given in Table 10.

TABLE 9

Results of pyrosequencing of cell lines GP5+

| Cell Line | Sequence | HPV type |
|---|---|---|
| SiHa | ACGCAGTACAAATA SEQ ID NO: 208 | HPV-16 |
| CaSki | ACGCAGTACAAATA SEQ ID NO: 209 | HPV-16 |
| C4I | TCGCAGTACCAATTT SEQ ID NO: 210 | HPV-18 |

TABLE 9-continued

Results of pyrosequencing of cell lines GP5+

| Cell Line | Sequence | HPV type |
|---|---|---|
| ME-180 | ACGCAGTACAAATA SEQ ID NO: 211 | HPV-16 |
| SW765 | TCGCAGTACCAATTT SEQ ID NO: 212 | HPV-18 |

TABLE 9-continued

Results of pyrosequencing of cell lines GP5+

| Cell Line | Sequence | HPV type |
|---|---|---|
| MS751 | – | – |
| HeLa | – | – |
| C33 | – | – |

TABLE 10

Results Cell lines hybridization with assay

| Cell line | HPV types |
|---|---|
| SiHa | HPV-16 and HPV-31 |
| CaSki | HPV-16 |
| C4I | HPV-18 |
| ME-180 | HPV-16 |
| SW765 | HPV-18 and HPV-39 |
| MS751 | Negative |
| HeLa | Negative |
| C33 | Negative |

3.4. HPV Detection and Typing for Vulvar Carcinomas

Following the amplification of the genomic DNA with the consensus primers PGMY09/11 and GP5+ and GP6+ (Table 11), an electrophoretic gel was run of samples 1, 20, 21, 22, 23, 24, 25, 26, 27, 28, 29 and 30 (data not shown). Samples 4, 11, 13, 19 and 21 were positive, as shown by bands at about 150 bp, and were selected for pyrosequencing. HPV-16 sequence signal was observed in samples 4, 11, 13 (Sequence not shown), and 21. A clear sequence signal could not be detected with sample 19 therefore pools of multi-sequencing primers were used because double HPV infection was suspected. With pool 2, a sequence signal for HPV-33 was observed for sample 19 (Sequence not shown). Amplification of the samples with the pool of HPV primers provided bands in additional samples; therefore all of the samples were pooled and hybridized to the chip in addition to the individual hybridization of the 5 samples that were sequenced. The hybridization results for samples 4 and 11 are given in FIG. 3. An overview of the hybridization results is given in Table 12.

TABLE 11

Pyrosequencing genomic samples with GP5+

| Sample | Sequence | HPV type |
|---|---|---|
| Sample 4 | ACGCAGTACAAATA<br>SEQ ID NO: 213 | HPV-16 |
| Sample 11 | ACGCAGTACAAATA<br>SEQ ID NO: 214 | HPV-16 |
| Sample 13 | ACGCAGTACAAATA<br>SEQ ID NO: 215 | HPV-16 |
| Sample 19 | TGTTGAAGAATA*<br>SEQ ID NO: 216 | HPV-33 |
| Sample 21 | ACGCAGTACAAATA<br>SEQ ID NO: 217 | HPV-16 |

*The sequence signal was detected with pool 2 of multi sequencing primers

TABLE 12

Hybridization assay with genomic DNA

| Sample number | HPV type |
|---|---|
| 4 | HPV-16 |
| 11 | HPV-16, -18, -19, -20, -45 |
| 13 | HPV-16, -67 |
| 19 | HPV-16, -18, -20, -45 |
| 21 | HPV-16 |

Samples 4 and 11 gave results as illustrated in FIG. 3. The symbols representing red, green and yellow, as well as the orientation of the spots are as described in connection with FIG. 2. Sample 4 (FIG. 3A) shows a positive result for HPV 16. FIG. 3B shows results from Sample 4, with positive signals for HPV-16, -18, -19, -20, and -45. Weak signals were observed from HPV-45 and HPV-18. The weak signals could be increased by eliminating green dye staining.

3.5. Validation E1 and L1 HPV Primers

Because additional HPV types were detected on the chip and it is known that in some cases the L1 region, used for most HPV detection methods, can contain deletions, primers were designed to amplify the E1 and L1 region of six HPV types that were detected on the chip hybridized with the pool of samples. The primers were validated through amplification of type specific HPV plasmids. Bands could be detected for all of the HPV plasmids (data not shown). That is, in an electrophoretic gel of HPV plasmids amplified with E1 and L1 HPV primers, bands could be seen at about 250 bp for both E1 and L1 genes in HPV types 16, 18, 31, 44 and 66. For the amplification of HPV-16, a positive band could be detected for E1 primers at approximately 250 bp, which is slightly higher than it should be. The correct size of the product is 184 bp. A band could also be detected at approximately 250 bp for the L1 primer, which is the correct product size. Amplification of the HPV-18 plasmid gave bands at the approximately 250 bp and 300 bp for the E1 and L1 primers respectively. Correct product sizes were also obtained for the amplification of HPV-29, -31, -44, and 66.

3.6. E1 and L1 Amplification of Vulvar Carcinomas

The E1 and L1 primers were also used for the amplification of the 30 clinical samples. All 30 samples were amplified with the individual primers and run on gel. Of the 30 samples amplified, 5 (Samples: 5, 11, 13, 21, and 30) were positive for the same HPV type in both regions, whereas most of the samples were positive for different HPV types for each region. There were 12 samples that were negative for both region and 10 samples were positive for only one region. Of those 10 samples, 4 were positive for the E1 region and negative for the L1 region (Samples: 3, 7, 15, and 18); the opposite was seen for the other 6 samples (Samples: 2, 9, 12, 14, 19, and 29). The results are presented in Table 13. The samples that were selected for performing cloning and sequencing confirm the presence of the different HPV region that was detected.

TABLE 13

Results amplification of genomic samples with E1 and L1 region

| Sample number | HPV types E1 region | L1 region |
|---|---|---|
| Sample 1 | HPV-66 | HPV-16 and HPV-18 |
| Sample 2 | Negative | HPV-31 |
| Sample 3 | HPV-66 | Negative |
| Sample 4 | HPV-16 | HPV-31 |
| Sample 5 | HPV-16 | HPV-16 |
| Sample 6 | Negative | Negative |
| Sample 7 | HPV-16 | Negative |
| Sample 8 | Negative | Negative |
| Sample 9 | Negative | HPV-16 and HPV-29 |
| Sample 10 | HPV-16 | HPV-29 |
| Sample 11 | HPV-16 | HPV-16 |
| Sample 12 | Negative | HPV-16 |
| Sample 13 | HPV-16 and HPV-66 | HPV-16 and HPV-66 |
| Sample 14 | Negative | HPV-66 |
| Sample 15 | HPV-18, HPV-31 and HPV-66 | Negative |
| Sample 16 | Negative | Negative |
| Sample 17 | Negative | Negative |
| Sample 18 | HPV-18 and HPV-66 | Negative |
| Sample 19 | Negative | HPV-16 |
| Sample 20 | Negative | Negative |
| Sample 21 | HPV-16 and HPV-66 | HPV-16 |
| Sample 22 | Negative | Negative |
| Sample 23 | Negative | Negative |
| Sample 24 | Negative | Negative |
| Sample 25 | Negative | Negative |
| Sample 26 | Negative | Negative |
| Sample 27 | Negative | Negative |
| Sample 28 | Negative | Negative |
| Sample 29 | Negative | HPV-31 |
| Sample 30 | HPV-16 | HPV-16 |

Although the above was carried out with clinical samples for vulvular carcinomas, other samples and types of samples may be tested. These may include paraffin-fixed samples, cervical swabs or scrapes, saline cervicovaginal lavages, frozen biopsies, etc.

These may be obtained from mucosal linings of the head and neck, anal lesions, cervical specimens, plantar warts, intraepithelial lesions, skin cancer biopsies, warts of genital mucosa, oral cavity, respiratory, and conjunctival mucosae, breast tumors, small cell lung cancer samples, etc.

3.7 Alternative Embodiments: Primers, Probe Sequences, Arrays and Amplification Primer and Probe Sequences Since the entire genomic sequences of the 90 types of HPV detected by the probes and primers described above are known, alternative sequences may be employed using the principles taught here. For example, the particular "universal" primers in Table 4, which lists specifically the forward and reverse amplification primers by HPV type may be modified to cover different types. The primers are termed "universal" in that they are specific to HPV, but not necessarily to any genotype. Also, a relatively small number of primers (about 68) of primers can be used to cover over 90 different HPV types. Given a sequence description, a newly determined type of HPV could be added to the collection of types detected by the present assay, by aligning the type with the present primers, which are generally in the region of nt 1800 to nt 1950 of the HPV genome, and have a high degree of homology. Similarly, the probe sequences given in Table 5 may also be varied by alignment with a new type, addition of a poly T linker and addition of a molecular tag. The poly T linker is designed to provide a uniform size among the probes. The molecular tag will be the same for all probes, and is designed to be distinct from the unique probes, and to have the same melting temperature Tm, GC content, no secondary structure and unique sequence that not present in any known genome.

Other variations to the sequences given in Tables 4 and 5 are possible. For example, the primers may be longer or shorter by about 10 bases. They may be moved 3' or 5' along the known HPV genome by about 30 bases. Similarly the probes may be lengthened up to 40 bases or shortened to about 10 bases. They may also be shifted along the known HPV target sequences by about 100 nt 5' or about 100 bases 3'. That is, a sequence in Table 4 or 5 may be extended by reference to the corresponding known HPV genome for the necessary sequence information. Other considerations of specificity, dimerization, secondary structure, etc. will also apply, as is known in the art, and taught here.

The variations in length and or starting or ending points may be checked against the GenBank nucleotide sequence database for human and viral sequences. They should also be checked against the Los Alamos HPV sequence database to rule out undesired cross reactivity.

Primer sequences may be checked by programs such as PrimerQuest from Integrated DNA Technologies, PrimaClade from the Kellogg Laboratory at the University of Missouri at Saint Louis (designed for multiple alignments), Primer select from DNAStar, and ROSO (Recherche et Optimisation de Sondes Oligonucléotidiques) software to design optimized oligonucleotide probes (size over 25 nucleotides) for microarrays, as well as numerous other software tools.

For example, a primer used for amplification of HPV (taken from Table 4) is as follows:

| HPV types | Sequence (Forward) | HPV types (Reverse) | Sequence |
|---|---|---|---|
| HPV-15, 37, 80 | BTCA TAT GCA TAT TGT ACC ATA GT SEQ ID NO: 218 | XX | CACCAGAATGGATAGT TAGAC SEQ ID NO: 219 |

Where B = biotin.

A BLAST search with the forward primer sequence reveals the following results:

TABLE 14

| Accession | Description | Max. Score | Total Score | Query Coverage | Max. Ident |
|---|---|---|---|---|---|
| X74468.1 | Human papillomavirus type 15 genomic DNA | 46.1 | 46.1 | 100% | 100% |
| Y15176.1 | Human papillomavirus type 80 E6, E7, E1, E2, E4, L2, and L1 genes | 38.2 | 38.2 | 100% | 95% |
| U31786.1 | Human papillomavirus type 37, complete genome | 38.2 | 38.2 | 100% | 95% |
| X55964.1 | Human papilloma virus type 2a complete DNA | 34.2 | 34.2 | 91% | 95% |

TABLE 14-continued

| Accession | Description | Max. Score | Total Score | Query Coverage | Max. Ident |
|---|---|---|---|---|---|
| EF154777.1 | HIV-1 isolate U-349c2 from USA envelope glycoprotein (env) gene, partial cds | 32.2 | 32.2 | 69% | 100% |
| AY253958.1 | HIV-1 isolate Pt16 from Japan envelope glycoprotein (env) gene, partial cds | 32.2 | 32.2 | 69% | 100% |

Thus, the present sequence is a 100% match for the HPV strains to which it is directed, and it will not detect strains, such as type 2a, which have 91% identity to the primer.

Thus, it is contemplated that primer and probe sequences with at least about 90% identity, preferably at least about 95% identity, to the specific sequences be included within the materials and methods set forth here. As stated previously, a primer may amplify more than one sample E1 sequence; the amplicon is hybridized to a specific probe.

Also, the present assay may be adapted to bovine papilloma virus, since this virus also contains an E1 gene.

Primer and Probe Compositions

Also, various synthetic or alternative nucleotides may be employed. Various families of artificial nucleic acids are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops (1997) Nucleic Acids Res. 25:4866-4871. Nonpolar molecules can also be used to mimic the shape of natural DNA bases. A non-hydrogen-bonding shape mimic for adenine can replicate efficiently and selectively against a nonpolar shape mimic for thymine (see, e.g., Morales (1998) Nat. Struct. Biol. 5:950-954). Inosine ("I") is a synthetic base that can be used to substitute for any of the four, naturally-occurring bases (A, C, G or T), Pyrrolo-dC, a fluorescent DNA base that can substitute for cytosine.

Any type of label can be used in the present primers, probes, and test target sequences. Suitable labels include radioactive labels (MP Biomedicals and PerkinElmer Life and Analytical Science), metal nanoparticles, ("Metal nanoparticles as labels for heterogeneous, chip-based DNA detection," Fritzsche et al 2003 Nanotechnology 14 R63-R73), fluorescent labels such as cyanine (Cy) dyes, BODIPY, fluorescein, etc. A number of suitable dyes are available from Synthegen, LLC, Houston, Tex. Other suitable fluorescent labels include FAM, ROX, Cy5.0, D4 (Beckman) and IRD800 (LICOR).

The exemplified primers are labeled with biotin and detected with a SAPE stain, which consists of fluorescent phycoerythrin conjugated to a streptavidin. Alternatively, the biotin label, presented at a site where the PCR-product is hybridized to the probe, may be subsequently detected by incubation with its streptavidin ligand conjugated to an enzymatic label, such as HRP and incubation blot with the peroxidase substrate.

In order to provide further guidance in the design of alternate primers and probes, Table 15 below sets forth the sequence in between the: universal primer: (See Table 4) for the HPV microarray, by genotype.

TABLE 15

| HPV type | Sequences showing universal primers (bold) for the HPV DNA chip and micro array probes underlined |
|---|---|
| HPV68ME180 | TCTCCTATATCTGCTGCAGAAGAAATAGAACTGCACCCT CTTGTGGCTCATGCACAGGATAGCAGTGGCTTATTTGAT GTTTATGCAGAAC SEQ ID NO: 220 |
| HPU40822 | TCTCCTATATCTGCTGCAGAAGAAATAGAACTGCACCCT CTTGTGGCTCATGCACAGGATAGCAGTGGCTTATTTGAT GTTTATGCAGAAC SEQ ID NO: 221 |
| HPV35 | GCAATGTCAAATATTAGTGAGGTTGATGGAGAAA CACCAGAATGGA TTCAAAGACAAACAGTATTACAGCATAGTTTT AATGA<u>TGCAATATTTGACCTATCTGAA</u>ATGGTACA- SEQ ID NO: 222 |
| HPV31 | GGAATGTCAAACATTAGCGATGTATATGGTGAAA CACCAGAATGGAT AGAAAGACAAACAGTATTACAGCATAGTTTTAA TGA<u>CACAACATTTGATTTGTCCCAA</u>ATGGTACA- SEQ ID NO: 223 |
| HPV16 | GGTATATCAAATATTAGTGAAGTGTATGGAGACACGCCA GAATGGATACAAAGACAAACAGTATTACAACATAGTTTT AATGA<u>TTGTACATTTGAATTATCACAGA</u>TGGTACA- SEQ ID NO: 224 |
| HPV26 | GGGTTGTCCAATATAAGTGAGACATATGGAGATACACCA GAATGGATAGTACGACAAACACAATTAGAACATAGT<u>TTT</u> |

TABLE 15-continued

| HPV type | Sequences showing universal primers (bold) for the HPV DNA chip and micro array probes underlined |
|---|---|
| | GATGATGCTACATTTGATTTATCAAAAATGGTGCA-SEQ ID NO: 225 |
| NC_002171 | GGATTATCAAACATAAGTGAAACACATGGGGACACACCAGAATGGATAGTAAGACAAACACAATTAGAACATAGTTTTGAAGATACAATATTTGATTTATCAAAAATGGTGCA-SEQ ID NO: 226 |
| HPV51 | GGCATATCAAACATTAGCAATACATATGGAGAGACACCTGAATGGATTACACGACAAACGCAACTACAACATAGTTTTGAGGATAGTACCTTTGAATTATCACAAATGGTGCA-SEQ ID NO: 227 |
| NC_002172 | GGAATATCAAACATTAGTAGCACATATGGCGAAACACCAGAATGGATTACAAGACAAACACAACTACAGCACAGTTTTGATGATAGCACGTTTGAACTATCGCAAATGGTACA-SEQ ID NO: 228 |
| HPV56 | GCAATGTCAAATATTAGTGATGTGTATGGAGACACACCAGAATGGATACAAAGACAAACACAATTGCAACACAGTTTACAGGATAGTCAATTTGAATTATCTAAAATGGTGCA-SEQ ID NO: 229 |
| HPV66 | GCAATGTCAAATATTAGTGAGGTGTATGGGGAAACACCAGAATGGATACAAAGACAGACACAATTGCAACACAGTTTACAAGACAATCAATTTGAATTGTCTAAAATGGTACA-SEQ ID NO: 230 |
| HPV30 | GCAATGTCTAATATTAGTGACATATATGGTGAGACACCAGAATGGATACAGCGACAAACACAAATACAGCACAGTTTTCAGGACTGCCAATTTGAACTGTCGAAAATGGTGCA-SEQ ID NO: 231 |
| HPV53 | TCTATATCCAACATTAGTGACGTGTATGGGAGTACACCAGAATGGATAGAAAGACAAACACAGTTACAACATAGCTTTGAGGACTGTCAATTTGAACTATCTAAAATGGTGCA-SEQ ID NO: 232 |
| HPV34 | AGCCTATCAAACATTAGTGAAACGGTGGGAGAAGTACCCGAATGGATTAAAAGACAAACAGTAGTACAGCACAGCTTAGAGGACTGTCAATTTGACCTATCTCAAATGGTACA-SEQ ID NO: 233 |
| HPV73 | AGTTTATCAAATATTAGTGAAATAGTAGGAGACACACCTGAGTGGATTAAAAGACAAACGTTAGTGCAGCATAGTTTAGATGATAGTCAATTTGACCTATCTCAAATGATACA-SEQ ID NO: 234 |
| HPV33 | GCAATGTCAAACATTAGTGATGTACAAGGTACAACACCTGAATGGATAGATAGACTAACTGTTTTACAACATAGCTTTAATGATAATATATTTGATTTAAGTGAAATGGTACA-SEQ ID NO: 235 |
| HPV58 | GCAATGTCAAATATAAGTGATGTGCAAGGGACAACACCAGAATGGATAGATAGATTAACAGTGTTACAGCATAGCTTTAATGATATATTTGATTTAAGTGAAATGATACA-SEQ ID NO: 236 |
| NC_004710 | GGAATGTCAAATATAAGTGAAGTAAGTGGGCAAACACCAGAATGGATAGAAAGACTAACGGTACTGCAACATAGTTTTGATGATACTATATTTGATTTAGGAGAAATGGTGCA-SEQ ID NO: 237 |
| HPV52 | GGTTTGTCTAATATTAGTGAGGTATATGGTACCACCCCAGAATGGATAGAACAACAAACAGTATTACAGCATAGCTTTGACAATAGCATATTCGATTTTGGAGAAATGGTGCA-SEQ ID NO: 238 |
| HPV18 | GGAATATCAAATATTAGTGAAGTAATGGGAGACACACCTGAGTGGATACAAAGACTTACTATTATACAACATGGAATAGATAGCAATTTTGATTTGTCAGAAATGGTACA-SEQ ID NO: 239 |
| HPV45 | GGTATATCCAATATTAGTGAAGTAAGTGGAGACACACCTGAGTGGATACAAAGACTGACAATTATTCAACATGGTATT |

TABLE 15-continued

| HPV type | Sequences showing universal primers (bold) for the HPV DNA chip and micro array probes underlined |
|---|---|
| | GACGATAGTAATTTTGATTTGTCAGACATGGTGCA-SEQ ID NO: 240 |
| NC_004762 | GGAATATCAAATATTAGTGAAGTAACAGGAGACACACCTGAGTGGATACAAAGACAAACTATTATACAACA<u>TGGTATAGATGACAGTGTATTT</u>GACCTGTCAGAAATGATACA-SEQ ID NO: 241 |
| HPV59 | GGAATGTCCAATATTAGTGAAGTTATAGGGGAAACGCCCGAATGGATACAAAGACTAACAATTATACAACA<u>TGGAGTTGATGATAGCGTGT</u>TTGACCTGTCAGAAATGATACA-SEQ ID NO: 242 |
| HPV39 | GGTATATCCAATATTAGTGTGGTAACAGGGGATACGCCAGAATGGATACAACGATTAA<u>CTGTTATACAACATGGAATAGA</u>TGATAGTGTATTTGACCTATCGGACATGGTACA-SEQ ID NO: 244 |
| HPV70 | GGAATGTCTAATATAAGTGAAGTGTCAGGTACTACGCCAGAATGGATACAGCGATTAA<u>CAGTAATACAGCATGGAATAG</u>ATGACAGTGTATTTGACCTGTCTGATATGGTACA-SEQ ID NO: 245 |
| NC_001668 | GGTATATCAAATGCCAGTACAGTTATAGGGGAAGCACCAGAATGGATAACACGCCAA<u>ACTGTTATTGAACATGGGTTG</u>GCAGACAGTCAGTTTAAATTAACAGAAATGGTGCA-SEQ ID NO: 246 |
| HPV6b | GGTATATCAAATGCCAGTACAGTTATAGGGGAAGCACCAGAATGGATAACACGCCAAA<u>CAGTTATTGAACACGGGTTG</u>GCAGACAGTCAGTTTAAATTAACAGAAATGGTGCA-SEQ ID NO: 247 |
| HPV11 | GGCATTTCAAATGCAAGTACAGTTATAGGGGAGGCGCCGGAATGGATAACGCGC<u>CAGACCGTTATTGAACATAGT</u>TTGGCTGACAGTCAATTTAAATTAACTGAAATGGTGCA-SEQ ID NO: 248 |
| HPV44 | GGTATATCCAATGCCAGTATAGTAACTGGAGAAACACCGGAATGGATAACAAGGCAAACCATTGTAGAACATGG<u>GCTTGCAGACAACCAATTTAA</u>ATTAGCAGACATGGTTCA-SEQ ID NO: 249 |
| HPV55 | AGTATATCCAATGCCAGTATAGTTACTGGAGAAACGCCTGAATGGATAACAAGGCAAACCATTGTAGAACATGG<u>GCTTGGTGACAACCAATTCA</u>AAATTAACAGAAATGGTGCA-SEQ ID NO: 250 |
| HPV13 | GGTATTTCTAATGCTAGTATAGTAACTGGTGAAACACCAGAATGGATAAAAAGGCAAACAATTGTAGAGCA<u>TGGACTTGCAGATAATCAATTT</u>AAATTAACTGAAATGGTGCA-SEQ ID NO: 251 |
| HPV32 | GGAATATCTAATGCCAGTGTAGTAACCGGGGAAACACCCGAATGGATACAAAGACAAACAATTGTAGAACA<u>TTGCTTTGCAGATACACAGTT</u>TAATTTAACAGAAATGGTGCA-SEQ ID NO: 252 |
| HPV42 | GGAATATCTAATGCTAGCATTGTAACCGGAGACACACCAGAGTGGATTCAAAGACAAACAATTTTAGAACA<u>TTGTTTTGCAGATGCCCAATT</u>TAATTTAACAGAAATGGTGCA-SEQ ID NO: 253 |
| HPV40 | GGAATGGGTAATGGGAGCGAGGTGTCCGGCACAACACCGGAATGGATAGCTAAACAAA<u>CTATGTTAGAACACAGCTTTG</u>CTGACACAGTTTAGCCTAACAGACATGGTGCA-SEQ ID NO: 254 |
| HPV7 | GGAATGGGTAATGGAAGTGAGGTGTCTGGCACAACACCGGAATGGATAGCTAA<u>ACAAACAATGTTGGAACATAGTTTTG</u>CTGAAGCAGTTTAGTTTAACTCAGATGGTGCA-SEQ ID NO: 255 |
| NC_004085 | GGTATGGGAAATGGTAGTGAAGTATCGGGCACAACACCGGAATGGATAAGTAGACAGA<u>CAGTGTTAGAACACAGTTTTG</u> |

TABLE 15-continued

| HPV type | Sequences showing universal primers (bold) for the HPV DNA chip and micro array probes underlined |
|---|---|
| | GCAGACACACAGTTTAGTTTAACAAATATGGTGCA-SEQ ID NO: 256 |
| HPV27 | GCTATGGGTAACGGAAGTGAGGTATATGGGGAAACACCAGAATGGATTGTAAGACAGACGTTGGTAGGACATAGTATGGAAGATGAGCAGTTTAGACTATCTGTCATGGTACA-SEQ ID NO: 257 |
| HPV2a | GCCATGGGCAACGGAAGTGAGGTATATGGGGAAACACCAGAATGGATTGTTAGACGACGTTGGTAGGACATAGCATGGAAGACGAACAGTTCAGACTGTCAGTTATGGTACA-SEQ ID NO: 258 |
| HPV57 | TCCATGGGTAATGGGAGTGAGGTCTATGGAGAGACACCAGAATGGATTGTGAGACAGACACTGATAGGACACAGTATGGAGGATGAGCAGTTCAAATTATCTGTTATGGTGCA-SEQ ID NO: 259 |
| HPV61 | GCCATGGGAAACGCCAGCGAGGTGTATGGCGAAACACCTGAATGGATAGTAAGACAAACAGTGGTAGGACATGCAATGCAAGAAGCACAGTTTAGTTTGTCCATGTTAGTGCA-SEQ ID NO: 260 |
| HPV72 | GCAATGGGAAATGGCAGCGAGGTGTACGGGGAAACCCCAGAATGGATAGTAAGACAAACAGTAGTGGGGCATGCAATGCAAGAGACACAGTTTAGCCTTTCTACCTTAGTACA-SEQ ID NO: 261 |
| NC_004103 | GCAATGGGAAATGCAAGCGAAGTCTTTGGGGAAACACCAGAATGGATAGTAAGGCAGACAGTAATAGGGAGGCAATGAAGGAAACCCAGTTAGTCTATCAACATTAGTACA-SEQ ID NO: 262 |
| NC_002676 | GCAATGGGCAATGCATGTGAAGTGTTAGGGGAAACACCAGACTGGATAGTACGACAAACTGTAATTGGGCATGCAATGGGGGAAACGCAGTTTAGTTTATCAAAACTAGTGCA-SEQ ID NO: 263 |
| NC_000856 | GCTATGGGGAATGCCTCAGAAGTACTTGGGGAGACCCCAGAGTGGATTGTGCGACAAACAGTAGTAGGACATGCAATGGGAGAAGCCCAATTTAGTTTATCAATGCTTGTGCA-SEQ ID NO: 243 |
| NC_003115 | GCTATGGGCAATGCCAGTGAGGTGTTTGGGGACACGCCGGACTGGATAGTAAGACAAACAGTTATTGGACATGCAATGGGAGAAACACAATTTAGCCTATCTGTGTTAGTGCA-SEQ ID NO: 264 |
| NC_002627 | GCCATGAGCAATGCAAGTGAGGTGTTTGGGGAAACGCCGGACTGGATAGTTAGACAAACAGTAATAGGACATGCAATGGGAGAAACACAATTTAGCTTATCAGTACTGGTGCA-SEQ ID NO: 265 |
| NC_005351 | GCAATGGGAAATGCAAGTGAAACAGTAGGGGAAACACCAGAATGGATAGTAAGGCAAACAGTTGTGGGACATGCAATGCAGGAAACACAGTTTAGCCTGTCTGTAATGGTGCA-SEQ ID NO: 266 |
| NC_004104 | GGCATGGGCAATGCTAGTGAAATAATTGGAGAAACACCAGAATGGATTGTAAGACAAACAGTTGTGGGCACAGTCTAGAAGAATGCCAGTTTCAGTTATCAGTAATGGTGCA-SEQ ID NO: 267 |
| NC_002644 | AGCATGGGAAACGCAAGTGACATATTCGGGGAAACGCCAGAATGGATAGTTAGACAAACTGTGGTAGGACACAGCATGGAGGAATGCCAGTTTCAGTTATCAGTAATGGTGCA-SEQ ID NO: 268 |
| HPV10 | AGTATGTCCAGCTGTAGCGACGTGTATGGGGAAACACCAGAGTGGATAGTCAGGCAGACAATGGTGGGACATGCAATGGAGGATGCGCAGTTTAGCCTTTCAGAGATGGTGCA-SEQ ID NO: 269 |
| NC_005352 | AGCATGTCCAGCTGTAGTGATGTGTATGGAGAGACACCAGAGTGGATAGTTAGGCAAACAATGGTGGGACATGCAATG |

TABLE 15-continued

| HPV type | Sequences showing universal primers (bold) for the HPV DNA chip and micro array probes underlined |
|---|---|
| | GAGGATGCGCAGTTTACCCTTTCAGAGATGATACA-SEQ ID NO: 270 |
| HPV3 | AGCCTATCAAATTGTAGCGAGGTGTTTGGGGAAACACCAGAGTGGATAGTTAGGCAGACAGTGGTGGGACATGCATTAGAGGAAGCGCAGTTCAGTCTGTCAGAAATGGTGCA-SEQ ID NO: 271 |
| HPV28 | GCCATGTCAAACTGTAGTGATGTGTATGGGGAAACACCAGAGTGGATAGTGAGACAAACGATGGTTGGACATGCACTAGAGGAAGCACAGTTTAGTCTGTCGGAGATGGTACA-SEQ ID NO: 272 |
| HPU31784 | AGTATGTCCAATATTAGTGATGTGTATGGCGAGACACCTGAATGGATAGTAAGACAGACAATGGTAGGTCACGCATTACAAGAAGTACAGTTCAGTTTATCTGAAATGGTACA-SEQ ID NO: 273 |
| HPVY15175 | GGTATGTCTAATATTAGTGAAGTGTATGGAGACACTCCGGATTGGATAGTAAGACAAACAATTGTGGGACATGCTTTAGAAGAGACACAGTTTCGGTTATCAGACATGGTACA-SEQ ID NO: 274 |
| HPV54 | GGGCTGTCCAATGCAAGTGAAATATTTGGTACACCCCCGGAATGGCTGGCCAGACAAACTGTAATTGAATATAGCTTAGCAGACAGCCAGTTTGATTTATCTAAAATGGTACA-SEQ ID NO: 275 |
| HPV12 | GGTATGGGGTCAGGCGCATTTACCCATGGCACATATCCTGATTGGATTGCACATCAAACAATTTTGGGCCATCAAAATGCTGAAGCAAGCACATTTGATTTTTCAGCCATGGTCCA-SEQ ID NO: 276 |
| NC_004761 | GGTATGGGGTCAGGAGCATTTACATATGGTAAATATCCTGATTGGATTGCGCAGCAAACAGTACTTGGCCACCAAAATGCGGAGGCAAGCACATTTGATTTTTCAGTGATGGTACA-SEQ ID NO: 277 |
| HPV8 | GGAATGGGGACAGGAACATTCACGTATGGTTCATACCCTGATTGGATTGCACATCAAACAATTCTTGGCCATCAAAGTGCTGAAGCAAGCACCTTTGATTTTTCTGTAATGGTACA-SEQ ID NO: 278 |
| HPV20 | GCAATGGGGTCCGGAGCATTTTCTCATGGTCCATATCCTAACTGGATGGCACAGCAAACACTATTGTTGGTCATCAGAGCACAGAAGCCAGTGCTTTTGACTTGTCTGAAATGATTCA-SEQ ID NO: 279 |
| HPV21 | GCGATGGGGTCTGGAGCATTTACTTATGGACCTTATCCTGATTGGATTGCCCAGCAAACAATTGTTGGTCATCAAAGTACAGAAGCCAGTGCATTTGATATGTCTGCAATGGTTCA-SEQ ID NO: 280 |
| HPV14d | GCAATGGGGTCAGGGACATTTACTTATGGTCCCTACCCTGATTGGATGGCACATCAAACATATTGTTGGCCATCAAAGTACAGAAGCAAATGCATTTGATATGTCTGTTATGGTGCA-SEQ ID NO: 281 |
| HPV5 | TGTATGGGATCGGGGCGTTTAGCCATGGACCATATCCTGATTGGATTGCCCAACAAACTATATTAGGTCACAAAAGTGCTGAGGCAAGTACTTTTGATTTTTCAGCAATGGTCCA-SEQ ID NO: 282 |
| HPV36 | TGTATGGGATCGGGGGTGTTCAGTTATGGGCCATATCCTGATTGGATTGCACAACAGACTATATTAGGTCACAATAATGCTGAAGCAAGCACCTTTGATTTTTCACAGATGGTACA-SEQ ID NO: 310 |
| HPV47 | TGTATGGGACCTGGAGTGTTCACCCACGGTCCTTACCCTGAATGGATTGCACAATTAACCATTTTGGGCCATAAGAGTGCTGAGGCAAGTGCGTTTGATCTGTCAGTCATGGTTCA-SEQ ID NO: 283 |
| HPV19 | TGTATGGGATCTGGAGGGTTTACTTATGGTCCATACCCAGATTGGATAGCACAACAAACAATATTAGGTCATCAAAAT |

TABLE 15-continued

| HPV type | Sequences showing universal primers (bold) for the HPV DNA chip and micro array probes underlined |
|---|---|
| | GCTGAAGCAAGTAGTTTTGATTTGTCTGAAATGATTCA-SEQ ID NO: 284 |
| HPV25 | TCAATGGGTTCCGGAGTATTTACATATGGCTCATATCCAGATTGGATAGCCCACCAAACAATATTGGGCCATCAAAGCGCTGAAGCTAGTACATTTGATCTATCGGACATGGTTCA SEQ ID NO: 285 |
| HPV24 | AGCTCAAATGCTGCTACCTTTACACATGGGTCTTATCCTAAATGGATTATAGAACAAACACTGATAGGACATCAAACAGGAGAAGCTGCAACGTTTGACATGTCCACAATGGTACA-SEQ ID NO: 286 |
| NC_005133 | AGTTCCAACTCGGGAACATTTACCCATGGTTCATATCCTAAATGGATAGTAGAACAAACATTAATAGGACATCAGTCTGGAGAAGCGGCAACATTTGATATGTCAACTATGGTACA-SEQ ID NO: 287 |
| HPV4 | GCTATGTTAACAGAGAGTTCTGTTTTTGGACAAACACCGGATTGGATCGCAAAACAAACTCTCGTAAGTCATCAAGCAGCAACTACTGCAGAGACTTTTGAGTTATCTAGAATGGTTCA-SEQ ID NO: 288 |
| HPV65 | GCCATGTTAACAGAGAGCTTTGTTTTCGGACAGACACCAGATTGGATTGCAAAGCAAACCTTAGTAAGCCATCAAGCAGCAACTACTGCAGAAACATTCGAATTATCAAAAATGGTTCA-SEQ ID NO: 289 |
| AJ620210 | GCTTTGTTAACTGAATGCTTTGTATATGGACAAACACCGGATTGGATCGCTAAGCAGACAATAGTGAGCATCAGTCTGCTACAACTGCAGAAACATTTGAGTTGTCAAGAATGGTTCA-SEQ ID NO: 290 |
| HPV60 | TCATTTGGAAATGCATCGTTTATTTATGGACCGTTTCCAGATTGGTTAGCAAAATTAACTATGTTAGACCATGAATCCGCCGCGAGCTCAGAACAGTTTGAACTTGCTCAAATGATTCA-SEQ ID NO: 291 |
| HPV48 | ATTATAACTGATACATGTTTTAAATATGGCACTTTGCCTTCCTGGGTTAGTAGATTAACTATAGTAGAACATCAGTTAGCTTCAGCAGACACATTTTCATTATCTGAAATGGTACA-SEQ ID NO: 292 |
| HPV50 | GTAATAGCAGATACCTGTTATAAATATGGAGACTTTCCTGACTGGATAGCCACACATACTGTTATAAATCATCAGCTAGCAACTGCAGACAGCTTTAAATTTAGTGATATGGTACA-SEQ ID NO: 293 |
| HPV17 | AGTATGAATCCAAATGTGTATGCCCACGGTGAATATCCTGAGTGGATTTTAACACAAACTATGATTAATCATCAAACAGCACAGGCAACACAATTCGATCTATCTACCATGATACA-SEQ ID NO: 294 |
| HPV37 | AGCATGAATCCAAATGTCTATGCACATGGTGAATATCCTGAGTGGATTATGACACAAACCATGATCAATCACCAATCAGCAGAAGCTACACAATTTGATTTATCCACTATGATACA-SEQ ID NO: 295 |
| HPV15 | AGTATGAATCCAAATGTTTATGCTCATGGAGAATATCCTGAGTGGATAATGCACACAAACAATGATAAATCACCAAACAGCAGAAGCTACACAGTTTGATTTATCTACTATGGTACA-SEQ ID NO: 296 |
| HPVY15176 | AGTATGAATCCTAATGTTTATGCTCATGGAGAGTATCCTGAATGGATAATGACGCAGACAATGATAAGCCATCATACAGCAGAAGCTACACAGTTTGATTTATCTACTATGGTACA-SEQ ID NO: 297 |

TABLE 15-continued

| HPV type | Sequences showing universal primers (bold) for the HPV DNA chip and micro array probes underlined |
|---|---|
| HPV9 | AGTATGAACCCTAATGTATACGCACATGGTGCGTATCCT<br>GAATGGATACTTACACAAACACTAATTAATCACCAATCT<br>GCAAATGCTACACAATTTGACTTATCGACAATGATACA-<br>SEQ ID NO: 298 |
| HPVY15173 | AGTATGGACTCATCTGTGTATGCTCACGGAACGTATCCT<br>GATTGGATTGTGAATCAGACCATGTTAACACATCAGGCT<br>GCAGCAGAAGCTGTGCAATTTGATTTGTCTCAAATGATA<br>CA<br>SEQ ID NO: 299 |
| HPVY15174 | AGTATGGACTCATCTGTGTATGCTCACGGAACCTATCCT<br>GATTGGATAGTAAATCAGACCATGTTAACACATCAGGCT<br>GCAGCAGAAGCTGTGCAATTTGACTTATCTGAAATGATA<br>CA<br>SEQ ID NO: 300 |
| HPV49 | AGTATGGACTCATCTGTGTATGCTCATGGAGCCTATCCT<br>GATTGGATTGTAAATCAGACCATGATAAGTCATCAGGCA<br>GCAGCAGATGCTATGCAATTTGACCTTTCTGAAATGATA<br>CA<br>SEQ ID NO: 301 |
| HPV22 | AGTATGAATCCAAATGTCTATGCATTTGGAGAGTATCCT<br>GAGTGGATTATGACACAGACTATGATACATCACCAAACT<br>GCTGACAGTGTACAATTTGACCTGTCTGAAATGATACA-<br>SEQ ID NO: 302 |
| HPV23 | AGTATGAACCCTAATGTATATGCATTTGGTGAGTATCCT<br>GAGTGGATTGTGACACAAACCATGATACAACATCAAACT<br>GCTGACAGTATACAATTTGATTTGTCTCGTATGATTCA-<br>SEQ ID NO: 303 |
| NC_005134 | AGTATGAATCCAAATATCTATGCATTTGGGGAGTATCCA<br>GACTGGATTGTTCAGCAAACGATGATTAGTCACCATGAG<br>GGCGATAATTTGCAATTTGAATTGTCTCCTATGGTACA-<br>SEQ ID NO: 304 |
| HPV38 | AGTTTGAATAGTAATGTGTTTTGTTTTGGTGAAGCTCCT<br>GATTGGATTCTATCACAAACAATGATACAGCATCAAACT<br>GCTGACACTTTGCAGTTTGACTTGTCTCGAATGATTCA-<br>SEQ ID NO: 305 |
| NC_004500 | TCTATGAATAAAAATGTATATACCCATGGAGAATACCCA<br>GAGTGGATAGCAAATCAAACATTGCTTTCTCATCAGGAA<br>TATGAAACACAGCAATTTGATTTAAGTAGAATGATTCA-<br>SEQ ID NO: 306 |
| HPV1a | TCTATGTCTTCAACTGTTTTTACATGGGGTACAACTTTG<br>GAGTGGATTGCACAGCAAACCCTTATTAATCATCAGTTA<br>GATTCCGAAAGTCCCTTTGAGCTTTGTAAAATGGTTCA-<br>SEQ ID NO: 307 |
| HPV63 | TCTATGTCTCCAGCTGTATATACCTGGGGAGAAATGCCA<br>GATTGGATGGCGCAGCAGACATTGTTGAATCATCAATTA<br>GCATCAGAAAAGCATTTTGAATTGTCACAAATGGTACA-<br>SEQ ID NO: 308 |
| PAP41CG | TTTATGGGTACAGGGGGTATAAAACATGGCGCAATGCCA<br>GAAATAATTGTAAACCAGTGCGTGGTGTCTAATCAGCAG<br>ACAGACACCTTTGAATTATCACGTATGGTACA-<br>SEQ ID NO: 309 |

Array Formats

The term "array" as used here includes a variety of probe formats, including probes which may be attached to beads, fiber-optic DNA microarrays using etched optical fiber bundles filled with oligonucleotide-functionalized microspheres, gel and membrane based arrays and arrays in which the probes are mixed and later individually read.

Typically the array will be in one of two formats: In one format, a probe (500~5,000 bases long) is immobilized to a solid surface such as glass using robot spotting and exposed to a set of targets either separately or in a mixture. This method, "traditionally" called DNA microarray, is widely considered as developed at Stanford University. A recent article by R. Ekins and F. W. Chu (Microarrays: their origins and applications. Trends in Biotechnology, 1999, 17, 217-218) further describes this format. In a second format, an array of oligonucleotide (20~80-mer oligos) or peptide nucleic acid (PNA) probes is synthesized either in situ (on-chip) or by conventional synthesis followed by on-chip immobilization. The array is exposed to labeled sample DNA, hybridized, and the identity/abundance of complementary sequences are determined. Microarray of this format may be obtained from Affymetrix, Inc. Many companies are manufacturing oligonucleotide-based chips using alternative in-situ synthesis or depositioning technology.

The present arrays, if in a liquid or homogeneous format, may be modified to include "molecular tags" such that a given probe may be individually identified. The present molecular tags may be chosen from almost any unique sequence and incorporated into a probe. Alternatively, the amplified sequences may be identified with molecular tags. Further guidance is given in Nucleic Acids Research, Vol. 32 No. 17, "Molecular barcodes detect redundancy and contamination in hairpin-bisulfite PCR," by Brooks E. Miner et al. Also, description is found in Akeson, et al. U.S. Pat. No. 6,465,193 issued Oct. 15, 2002, entitled "Targeted molecular bar codes and methods for using the same," hereby incorporated by reference in its entirety. In this embodiment, the sample DNA is cleaved with a restriction endonuclease and a hairpin linker is ligated to a sticky end of the digested DNA.

Amplification

Due to the low copy number of HPV genomes in a typical clinical sample, the sample is specifically enriched for the E1 sequences of interest. This is preferably done by PCR, but, in addition to the above variations, there are other amplification and pre-amplification methods, which can be employed besides PCR. For example, Wang et al. "DNA amplification method tolerant to sample degradation," Genome Research 14:2357-2366, 2004, describes RCA-RCA (Restriction and Circularization-Aided Rolling Circle Amplification), an amplification methodology that overcomes problems associated with nucleic acid degradation.

Lovmar et al., "Quantitative evaluation by minisequencing and microarrays reveals accurate multiplexed SNP genotyping of whole genome amplified DNA," Nucleic Acids Research, 2003, Vol. 31, No. 21, describes a method of primer extension preamplification (PEP) or multiple displacement amplification (MDA) used for genotyping single nucleotide polymorphisms (SNPs) using multiplex, four-color fluorescent minisequencing in a microarray format. For example, the pyrosequencing method described here may be applied to detect hybridization of a very low number of HPV targets to probes by the incorporation of nucleotides into the duplex.

One may also adapt the present probes to an array for use with rolling circle amplification, as described in Nallur, et al. "Signal amplification by rolling circle amplification on DNA microarrays," Nucleic Acids Research, 2001, Vol. 29, No. 23 e118.

These variations are based on the similarities in the E1 region that allow simultaneous amplification and the differences that allow genotype identification.

CONCLUSION

The present examples, methods, procedures, specific compounds and molecules are meant to exemplify and illustrate the invention and should in no way be seen as limiting the scope of the invention, which is defined by the literal and equivalent scope of the appended claims. Any patents or publications mentioned in this specification and in the references are indicative of levels of those skilled in the art to which the patent pertains and are intended to convey details of the invention which may not be explicitly set out in the specification but would be understood by workers in the field when implementing various embodiments of the invention. Such patents or publications are hereby incorporated by reference to the same extent as if each was specifically and individually incorporated by reference and for the purpose of describing and enabling the method or material referred to.

REFERENCES

1. Alberths, Johnson, Lewis, Raff, Roberts, Walter, "Molecular Biology of The Cell," Fourth Edition, Garland Science, Taylor & Francis Group.
2. Ah Lee S., Kang D., Soo Seo S., Kim Jeong J., Young Yoo K., Tark Jeon Y., Weon Kim J., Hyun Park., N., Beom Kang S., Pyo Lee H., Sang Song Y., "Multiple HPV infection in cervical cancer screened by HPVDNAChip™," *Cancer Letters* (2003), 187-192.
3. Arroyo M., Bagchi S., Raychaudhuri P., "Association of human papillomavirus type 16 E7 protein with the S-phase-specific E2F-cyclin A complex," *Molecular and Cellular Biology* (1993), 13: 6537-6546.
4. Barnard P. and McMillan N., "The human papillomavirus E7 oncoprotein abrogates signaling mediated by interferon-alpha," *Virology* (1999), 259: 305-313.
5. Berezutskaya E., Yu A., Morozov A., Raychaudhuri P., Bagchi S., "Differential regulation of the pocket domains of the retinoblastoma family proteins by the HPV16 E7 oncoprotein," *Cell Growth and Differentiation* (1997), 8: 1277-1286.
6. Berkhout R., Bouwens Bavinck J., ter Schegget J., "Persistence of Human Papillomavirus DNA in Benign and (Pre) malignant Skin Lesions from Renal Transplant Recipients," *Journal of Clinical Microbiology* (2000), 38: 2087-2096.
7. Berkhout R., Tieben L., Smits H., Bouvers Bavinck J., Vermeer B., ter Schegget J., "Nested PCR approach for detection and typing of epidermodysplasia verruciformis associated human papillomavirus types in cutaneous cancers from renal transplant recipients," *Journal of Clinical Microbiology* (1995), 33: 690-695.
8. Brehm A., Nielsen S., Miska E., McCance D., Reid J., Bannister A., Kouzarides T., "The E7 oncoprotein associates with Mi2 and histone deacytelase activity to promote cell growth," *EMBO Journal* (1999), 18: 2449-2458.
9. van den Brule A., Snijders P., Raaphorst P., Schijnemakers H., Deluis H., Gissmann L., Meijer C., Walboomers J., "General Primer Polymerase Chain Reaction in Combination with Sequence Analysis for Identification of Potentially Novel Human Papillomavirus Genotypes in Cervical Lesions," *Journal of Clinical Microbiology* (1992), 30: 1716-1721.
10. Chen J., Reid C., Band V., Androphy E., "Interaction of papillomavirus E6 oncoproteins with a putative calcium-binding protein," *Science* (1995), 269: 529-531.
11. Classon M. and Dyson N., "p107 and p130: versatile proteins with interesting pockets," *Experimental Cell Research* (2001), 264: 135-147.
12. Clavel C., Masure M., Bory J-P., Putaud I., Mangeonjean C., Lorenzato M., Gabriel R., Quereux C., Birembaut P., "Hybrid Capture II-based human papillomavirus detection, a sensitive test to detect in routine high-grade cervical lesions: a preliminary study on 1518 women," *British Journal of Cancer* (1999), 80:1306-1311.

13. Desaintes C. and Demeret C., "Control of papillomavirus DNA replication and transcription," *Cancer Biology* (1996), 7: 339-347.
14. Duarte-Franco E. and Franco E., "Cancer of the Uterine Cervix," *BMC Women's Health* (2004), 4: S13.
15. Dyson N., Howley P., Munger K., Harlow E., "The human papillomavirus-16 E7 oncoprotein is able to bind to the retinoblastoma gene product," *Science* (1989), 243: 934-937.
16. Dyson N., Guida P., Munger K., Harlow E., "Homologous sequences in adenovirus E1A and human papillomavirus E7 proteins mediate interaction with the same set of cellular proteins," *Journal of Virology* (1992), 66: 6893-6902.
17. Evander M., Edlund K., Boden E., Gustafsson A. Jonsson M., Karlsson R., Rylander E., Wadell G., "Comparison of a One-Step and a Two-Step Polymerase Chain Reaction with Degenerate Primers in a Population-Based Study of Human Papillomavirus Infection in Young Swedish Women," *Journal of Clinical Microbiology* (1992), 30: 987-992.
18. Evander M., Frazer I., Payne E., Qi Y., Hengst K., McMillan N., "Identification of the alpha6 integrin as a candidate receptor for papillomviruses," *Journal of Virology* (1997), 71: 2449-2456.
19. Fakhrai-Rad H., Pourmand N., Ronaghi M., "Pyrosequencing™: An Accurate Detection Platform for Single Nucleotide Polymorphisms," *Human Mutation* (2002), 19: 479-485.
20. Farthing A., Masterson P., Mason P., Vousden K., "Human Papillomavirus detection by hybrid capture and its possible clinical use," *Journal of Clinical Pathology* (1995), 47: 167-171.
21. Farve M., Orth G., Majewski S., Baloul S. Pura A., Jablonska S., "Psoriasis: A possible Reservoir for Human Papillomavirus Type 5, the Virus Associated with Skin Carcinomas of the Epidermodysplasia Verruciformis," *The Journal of Investigative Dermatology* (1998), 110: 311-317.
22. Fehrmann F. and Laimins L., "Human papillomavirus: targeting differentiating epithelial cells for malignant transformation," *Oncogene* (2003), 22: 5201-5207.
23. Gao Q., Srinivasan S., Boyer S., Wazer D., Band V., "The E6 oncoproteins of high-risk papillomaviruses bind to a novel putative GAP protein, E6TP1, and it for degradation," *Molecular Cellular Biology* (1999), 19: 733-744.
24. Gharizadeh B., Ghaderi M., Donnelly D., Amini B., Wallin K-L., Nyren P., "Multiple-primer DNA sequencing method," *Electrophoresis* (2003), 24: 1145-1151.
25. Gharizadeh B., Kalantari M., Garcia C., Johansson B., Nyren P., "Typing of human papillomavirus by pyrosequencing," *Laboratory Investigation* (2001), 81: 673-679.
26. Gravitt P., Peyton C., Alessi T., Wheeler C., Coutlee F., Hildesheim A., Schiffman M., Scott D., Apple R., "Improved amplification of genital human papillomaviruses," *Journal of Clinical Microbiology* (2000), 38: 357-361.
27. Gillison M L, Koch W M, Capone R B, Spafford M, Westra W H, Wu L, Zahurak M L, Daniel R W, Viglione M, Symer D E, Shah K V, Sidransky D., "Evidence for a causal association between human papillomavirus and a subset of head and neck cancers," *Journal of National Cancer Institute* (2000), 9: 709-720.
28. Giovannelli L., Lama A., Capra G., Giordano V., Arico P., Ammatuna P., "Detection of Human Papillomavirus DNA in Cervical Samples: Analysis of the New PGMY-PCR Compared To the Hybrid Capture II and MY-PCR Assays and a Two-Step Nested PCR Assay," *Journal of Clinical Microbiology* (2004), 42: 3861-3864.
29. Giroglou T., Florin L., Schafer F., Streeck R E., Sapp M., "Human papillomavirus infection requires cell surface heparan sulfate," *Journal of Virology* (2001), 75: 1565-1570.
30. van Ham M., Bakkers J., Harbers G., Quint W., Massuger L., Melchers W., "Comparison of Two Commercial Assays for Detection of Human Papillomavirus (HPV) in Cervical Scrape Specimens: Validation of the Roche AMPLICOR HPV Test as a Means To Screen for HPV Genotypes Associated with a Higher Risk of Cervical Disorders," *Journal of Clinical Microbiology* (2005), 43: 2662-2667.
31. zur Hausen H., "Papillomaviruses Causing Cancer: Evasion From Host-Cell Control in Early in Carcinogenesis," *Journal of the Cancer Institute* (2000), 92: 690-698.
32. Hawley-Nelson P., Vousden K., Hubbert N., Lowy D., Schiller J., "HPV16 E6 and E7 proteins cooperate to immortalize human foreskin keratinocytes," *EMBO Journal* (1989), 8: 3905-3910.
33. Husnjak K., Grce M., Magdic L., Pavelic K., "Comparison of five different polymerase chain reaction methods for detection of human papillomavirus in cervical cell specimens," *Journal of Virological Methods* (2000), 88: 125-134.
34. Jacobs M., de Roda Husman A., van den Brule A., Snijders P., Meijer C., Walboomers A., "Group-specific differentiation between high- and low-risk human papillomavirus genotypes by general primer-mediated PCR and two cocktails of oligonucleotide probes," *Journal of Clinical Microbiology* (1995), 35: 901-905.
35. Joyce J G., Tung J S., Przysiecki C T., Cook J C., Lehman E D., Sands J A., Jansen K U., Keller P M, "The L1 major capsid protein of human papillomavirus type 11 recombinant virus-like particles interacts with heparin and cell-surface glycosaminoglycans on human keratinocytes," *Journal of Biological Chemistry* (1999), 274: 5810-5822.
36. Jung An H., Hoon Cho N., Young Lee S., Jo Kim S., Sook Mun M., Hyun Kim S., Kim Jeong J., "Correlation of Cervical Carcinoma and Precancerous Lesions with Human Papillomavirus (HPV) Genotypes Detected with the HPV DNA Microarray Method," *Cancer* (2003), 97: 1672-1680.
37. Kiyono T., Hiraiwa A., Fujita M., Hayashi Y., Akiyama T., Ishibashi M., "Binding of high-risk papillomavirus E6 oncoproteins to the human homologue of the *Drosophila* discs large tumor suppressor protein," *Proceedings of the National Academy of Science* (1997), 94: 11612-11616.
38. Klaassen C., Prinsen C., de Valk H., Horrevorts A., Jeunink M., Thunnissen F., "DNA Microarray Format for Detection and Subtyping of Human Palillomavirus," *Journal of Clinical Microbiology* (2004), 42: 2152-2160.
39. Kleter B., van Doom L-L., Schrauwen L., Molijn A., Sastrowijoto S., ter Schegget J., Lindeman J., Harmsel B., Burger M., Quint W., "Development and Clinical Evaluation of a Highly sensitive PCR-Reverse Hybridization Line Probe Assay for Detection and Identification of Anogenital Human Papillomavirus," *Journal of Clinical Microbiology* (1999), 37: 2508-2517.
40. Kleter B., van Doom L-L., ter Schegget J., Schrauwen L., van Krimpen K., Burger M., ter Harmsel B., Quint W., "Novel short-fragment PCR assay for highly sensitive broad-spectrum detection of anogenital human papillomaviruses," *American Journal of Pathology* (1998), 153: 1731-1739.

41. Klingelhutz A., Foster S., McDougall J., "Telomerase activation by the E6 gene product of human papillomavirus type 16," *Nature* (1996), 380: 79-82.
42. Klussmann J., Weissenborn S., Wieland U., Dries V., Kolligs J., Jungehuelsing M., Eckel H., Dienes H., Pfister H., Fuchs P., "Prevalence, Distribution, and Viral load of Human Papillomavirus 16 DNA in Tonsillar Carcinomas," *Cancer* (2001), 92: 2875-2884.
43. Lin H-P., Huang Y-Y., Wu H-Y., Kao J-T., "Method for testing for Human papillomavirus Infection in Patients with Cervical Intraepithelial Disease," *Journal of Clinical Microbiology* (2004), 42: 366-368.
44. Liu J., "Studies of the molecular mechanisms in the regulation of telomerase activity," *FASEB Journal* (1999), 13: 2091-2104.
45. Lodish H., Berk a., Zipursky s., Matsudaira P., Baltimore D., Darnell J., *Molecular Cell Biology*, Fourth Edition, W. H. Freeman and Company.
46. Longworth M. and Laimins L., "Pathogenesis of Human Papillomavirus in Differentiating Epithelia," *Microbiology and Molecular Biology Reviews* (2004), 362-372.
47. Manos M., Ting T., Wright D., Lewis A., Broker R., Wolinsky S., "Use of polymerase chain reaction amplification for the detection of genital human papillomaviruses," *Cancer cells* (1989), 7: 209-214.
48. McIntyre M., Ruesch M., Laimins L., "Human papillomavirus E7 oncoproteins bind a single form of cyclin E in a complex with cdk2 and p107," *Virology* (1996), 215: 73-82.
49. McKaig R., Baric R., Olshan A., "Human papillomavirus and head and neck cancer: epidemiology and molecular biology," *Head Neck* (1998), 20: 250-265.
50. Melchers W., Bakkers J., Wang J., de Wilde P., Boonstra H., Quint W., Hanselaar A., "Short fragment polymerase chain reaction reverse hybridization line probe assay to detect and genotype a broad spectrum of human papillomavirus types," *American Journal of Pathology* (1999), 155: 1473-1478.
51. Meyerson M., Counter C., Eaton E., Ellisen L., Steiner P., Caddle S., Ziaugra L., Beijersbergen R., Davidoff M., Liu Q., Bachetti S., Haber A., Weinberg R., "hEST2, the putative human telomerase catalytic subunit gene, is up-regulated in tumor cells and during immortalization," *Cell* (1997), 90: 785-795.
52. Monsonego J., Bohbot J., Pollini G., Krawec C., Vincent C., Merignargues I., Haroun F., Sednaoui P., Monfort L., Dachez R., Syrjänen K., "Performance of the Roche AMPLICOR® Human papillomavirus (HPV) test in prediction of cervical intraepithelial neoplasia (CIN) in women with abnormal PAP smear," *Gynecological Oncology* (2005), 99: 160-168.
53. Münger k., Baldwin A., Edwards K., Hayakawa H., Nguyen C., Owens M., Grace M., Huh K., "Mechanisms of Human Papillomavirus-Induced Oncogenesis," *Journal of Virology* (2004), 78: 11451-11460.
54. Munger K. and Howley P., "Human papillomavirus immortalization and transformation functions," *Virus Research* (2002), 89: 213-228.
55. Nakamura T., Morin G., Chapman K., Weinrich S., Andrews W., Linger J., Harley C., Cech T., "Telomerase catalytic subunit homologs from fission yeast and human," *Science* (1997), 277: 955-959.
56. Novelli G., Gennarelli M., De Santis L., Angeloni P., Dallapiccola B., "Inosine-containing primers in human papillomavirus detection by polymerase chain reaction," *Biomedicine Pharmacotherapy* (1992), 46: 167-169.
57. Oh T., Kim C., Woo S., Kim T., Jeong D., Kim M., Lee S., Cho H., An S., "Development and Clinical Evaluation of a Highly Sensitive DNA Microarray for Detection and Genotyping of Human Papillomavirus," *Journal of Clinical Microbiology* (2004), 42: 3272-3280.
58. Oliveira L., de Paula Fernandez A., Xavier B., Rodrigues E., Cavalcanti S., "Analysis of the p53 gene and papillomavirus detection in smears from cervical lesions," *San Paulo Medical Journal* (2002), 120: 20-22.
59. Pfister H., Chapter 8: Human Papillomavirus and Skin Cancer, *Journal of the National Cancer Institute Monographs* (2003), 52-56.
60. Pourmand N., Elahi E., Davis R., Ronaghi M., "Multiplex Pyrosequencing," *Nucleic Acids Research* (2002), 30.
61. de Roda Husman A., Walboomers A., van den Brule A., Meijer C., Snijders P., "The use of general primers GP5 and GP6 elongated at their 3' ends with adjacent highly conserved sequences improves human papillomavirus detection by PCR," *Journal General Virology* (1995), 76: 1057-1062.
62. Ronaghi M., "Pyrosequencing: A tool for sequence-based analysis," 1998.
63. Ronco L., Karpova A., Vidal M., Howley P., "Human papillomavirus 16 E6 oncoprotein binds to interferon regulatory factor-3 and inhibits its transcriptional activity," *Genes & Development* (1998), 12: 2061-2072.
64. Scheffner M., Huibregtse J., Vierstra R., Howley P., "The HPV-16 E6 and E6-AP complex functions as a ubiquitin-protein ligase in the ubiquitination of p53," *Cell* (1993), 75: 495-505.
65. Scheffner M., Werness B., Huibregtse J., Levine A., Howley P., "The E6 oncoprotein encoded by human papillomavirus types 16 and 18 promotes the degradation of p53."
66. Schiffman M., Kiviat N., Burk R., Shah K., Daniel R., Lewis R., Kuypers J., Manos M., Scott D., Sherman M., Kurman R., Stoler M., Glass A., Rush B., Mielzinska I., Lorincz A., "Accuracy and interlaboratory reliability of human papillomavirus DNA testing by Hybrid Capture," *Journal of Clinical Microbiology* (1995), 33: 545-550.
67. Sedman S., Barbosa M., Vass W., Hubbert N., Haas J., Lowy D., Schiller J., "The full-length E6 protein of human papillomavirus type 16 has transforming and trans-activating activities and cooperates with e7 to immortalize keratinocytes in culture," *Journal of Virology* (1991), 66: 2125-2134.
68. Shafti-Keramat S., Handisurya A., Kriehuber E., Meneguzzi g., Slupetzky K., Kirnbauer R., "Different heparan sulfate proteoglycans serve as cellular receptors for human papillomaviruses," *Journal of Virology* (2003), 77: 13125-13135.
69. Snijders P., van den Brule A., Meijer C., "The clinical relevance of human papillomavirus testing: relationship between analytical and clinical sensitivity," *Journal of Pathology* (2003), 201: 1-6.
70. Snijders P., van den Brule A, Schrijnemakers H., Snow G., Meijer C, Walboomers J., "The use of general primers in the polymerase chain reaction permits the detection of a broad spectrum of human papillomavirus genotypes," *Journal of General Virology* (1990), 71: 173-181.
71. Stubenrauch F. and Laimins L., "Human papillomavirus life cycle: active and latent phases," *Cancer Biology* (1999), 9: 379-386.
72. Stubenrauch F., Zobel T., Iftner T., "The E8 Domain Confers a Novel Long-Distance Transcriptional Repression Activity on the E8^E2C Protein of High-Risk Human Papillomavirus Type 31," *Journal of Virology* (2001), 75: 4139-4149.

73. Sun X., Ferenczy A., Johnson D., Koulos J., Lungu O., Richart R., Wright T., "Evaluation of the Hybrid Capture human papillomavirus deoxyribonucleic acid detection test," *American Journal of Obstetrics Gynecology* (1995), 173:1432-1437.
74. Szentirmay Z., Polus K., Tamas L., Szentkuti G., Kurcsics J., Csernak E., Toth E., Kasler M., "Human papillomavirus in head and neck cancer: Molecular biology and clinicopathological correlations," *Cancer and Metastasis Reviews* (2005), 24: 19-34.
75. Terry G., Ho L., Londesborough P., Cuzick J., Mielzynska-Lohnas I., Lorincz A., "Detection of high-risk HPV types by the Hybrid Capture 2 test," (2001) 65: 155-162.
76. Thomas M. and Banks L., "Human papillomavirus (HPV) E6 interactions with Bak are conserved amongst E6 proteins from high and low risk HPV types," *Journal General Virology* (1999), 80: 1513-1517.
77. Thomas M. and Banks L., "Inhibition of Bak-induced apoptosis by HPV-18 E6," *Oncogene* (1998), 10: 2943-2954.
78. Tong X. and Howley P., "The Bovine papillomavirus E6 oncoprotein interacts with paxillin and disrupts the actin cytoskeleton," *Proceedings of the National Academy of Science* (1997), 94: 4412-4417.
79. Vande Pol S., Brown M., Turner C., "Association of bovine papillomavirus type 1 E6 oncoprotein interaction motif," *Oncogene* (1998), 16: 43-52.
80. Vernon S., Unger E., Williams D., "Comparison of human papillomavirus detection and typing by cycle sequencing, line blotting, and hybrid capture," *Journal of Clinical Microbiology* (2000), 38: 651-655.
81. Wang S., Sherman M., Hildesheim A., Lacey J., Devesa S., "Cervical Adenocarcinoma and Squamous Cell Carcinoma Incidence Trends among White Women and Black Women in the United States for 1976-2000," *Cancer* (2004), 100: 1035-1044.
82. Weissenborn S., Hopfl R., Weber F., Smola H., Pfister H., Fuchs P., "High Prevalence of a Variety of Epidermodysplasia Verruciformis-Associated Human Papillomaviruses in Psoriatic Skin of Patients Treated or not Treated with PUVA," *The Society for Investigative Dermatology* (1999), 133: 122-126.
83. Werness B., Levine A., Howley P., "Association of human papillomavirus types 16 and 18 E6 proteins with p53," *Science* (1990), 248: 76-79.
84. Ylitalo N., Bergstrom T., Gyllensten U., "Detection of genital human papillomavirus by single-tube nested PCR and type-specific oligonucleotide hybridization," *Journal of Clinical Microbiology* (1995), 33: 1822-1828.
85. Yoshikawa H., Kawana T., Kitagawa K., Mizuno M., Yoshikura H., Iwamoto A., "Amplification and typing of multiple cervical cancer-associated human papillomavirus DNAs using a single pair of primers," *International Journal of Cancer* (1990), 45: 990-992.
86. Zerfass K., Schulze A., Spitkovsky D., Friedman V., Henglein B., Jansen-Durr P., "Sequential activation of cyclin E and cyclin A gene expression by human papillomavirus type 16 E7 through sequences necessary for transformation," *Journal of Virology* (1995), 69: 6389-6399.
87. Zielinski G., Rozendaal L., Voorhorst F., Berkhof J., Snijders P., Risse E., Runsink A., de Schipper F., Meijer C, "HPV testing can reduce the number of follow-up visits in women treated for cervical intraepithelial neoplasia grade 3," *Gynecological Oncology* (2003), 91: 67-73.

What is claimed is:

1. An array comprising a plurality of distinct locations, each location having probe molecules comprising a nucleic acid sequence complementary to a single genotype of HPV E1 sequence said locations comprising locations of probe molecules having sequences complementary to HPV genotypes 16, 18, 29, 31, 44, and 66, said probe molecules comprising sequences
   (a) at least 90% identical to SEQ ID NO:104, and specifically binding to HPV-16,
   (b) at least 90% identical to SEQ ID NO:108, and specifically binding to HPV 18,
   (c) at least 90% identical to SEQ ID NO:130, and specifically binding to HPV 29,
   (d) at least 90% identical to SEQ ID NO:134, and specifically binding to HPV 31,
   (e) at least 90% identical to SEQ ID NO:158, and specifically binding to HPV 44, and
   (f) at least 90% identical to SEQ ID NO:109, and specifically binding to HPV 66.

2. The array of claim 1 wherein each probe has a length between 41 and 60 nucleotides.

3. The array of claim 1 further comprising probes for HPV genotypes, 33, 35, 39, 45, 51, 52, 56, 58, -69, 6, 11, 34, 40, and 42.

4. The array of claim 1 wherein the probe molecules further each comprise a control sequence for binding the same target, said target being a labeled control.

5. A method for detecting and typing HPV in a sample, comprising contacting the sample with the array of claim 1.

6. The method of claim 5 further comprising the steps of amplifying HPV DNA from an HPV E1 gene with said mixture of primers and hybridizing the amplification product to a probe unique to each type to be detected.

7. A method for detecting and genotyping HPV in a sample, comprising the steps of:
   contacting the sample with a mixture of amplification primers, each hybridizing to one or more E1 regions, said mixture comprising pairs of primers directed to at least 20 genotypes of HPV;
   b) amplifying any HPV DNA in the sample using the primers to produce amplicons; and
   c) contacting the amplicons with probes unique for each genotype to be detected, said probes comprised in an array as defined in claim 1.

8. The method of claim 7 wherein the at least 20 different genotypes comprise at least one of HPV-16, -18, -31, -33, -35, -39, -45, -51, -56, -58, -66, -69 and HPV-6, -11, -34, -40, -42, -43, -44.

9. The method of claim 7 wherein said amplification primers comprise primer pairs selected from the following:

| HPV types | SEQ ID NO (F, R) | Sequence (Forward) | HPV types (Reverse) | Sequence |
|---|---|---|---|---|
| HPV-15, 37, 8080 | 218, 219 | BTCA TAT GCA TAT TGT ACC ATA GT | XX | CACCAGAATGGATAGT TAGAC |
| HPV-51, 82 | 9, 10 | BTCA AAT GCC CAT TGC ACC AT | HPV-3, 94 | CACCAGAGTGGATAGT TAGGC |
| HPV-51, 82 | 11, 12 | BTCA AAT GCC CAC TGA ATC AT | HPV-10 | CACCAGAGTGGATAGT CAGG |
| HPVa-81, 10 | 13, 14 | BTCA TAT GCC CAC TGC ACC A | HPV-28 | CACCAGAGTGGATAGT GAGAC |
| HPVa-81, 10 | 15, 16 | BTCG TAT GCC CAC TGC ACC | HPV-29, 72, 91 | CACCTGAATGGATAGT AAGAC |
| HPVa-28, 2A, 27 | 17, 18 | BGGT CAT ATG CAT ACT GTA CCA T | HPV-77, 61 | CTCCGGATTGGATAGTA AGAC |
| HPVb-28, 2A, 27 | 19, 20 | BTCG TAT GCA TAC TGT ACC AT | HPV-27, 90 | CACCAGAATGGATTGT AAGAC |

-continued

| HPV types | SEQ ID NO (F, R) | Sequence (Forward) | HPV types (Reverse) | Sequence |
|---|---|---|---|---|
| HPV-3, 57 | 21, 22 | BTCA TAT GCG TAC TGC ACC AT | HPV-71, 2A, 87 33, 58 | CACCAGAATGGATTGTT AGAC |
| HPV-90, 71, 54 | 23, 24 | BTCA TAT GCC CAT TGC ACC AT | HPV-57 | CACCAGAATGGATTGT GAGAC |
| HPVa-53, 41 | 25, 26 | BTCC AAT GCC CAC TGC AC | HPV-81, 89 | CACCAGAATGGATAGT AAGGC |
| HPVb-53, 41 | 27, 28 | BTCA AAT GCC CAC TGC AC | HPV-84, 86 | CACCAGAACTGGATAGT ACGAC |
| HPVa-39, 35, 31, 96, 48, 67 | 29, 30 | BTCA AAT GCC CAT TGT ACC AT | HPV-6A, 6B, 11 | CACCAGAATGGATAAC ACGCC |
| HPVb-39, 35, 31, 96, 48, 67 | 31, 32 | BTCA TAT GCC CAT TGT ACC AT | HPV-44, 55 | CACCAGAATGGATAAC AAGGC |
| HPV-12 | 33, 34 | BTCG AAG GCC CAT TGG ACC | HPV-13 | CACCAGAATGGATAAA AAGGC |
| HPV-16 | 35, 36 | BTCG TAG GCC CAT TGT ACC AT | HPV-32, 59, 34, 73 | CACCCGAATGGATACA AAGAC |
| HPV-36 | 37, 38 | BTCA AAG GCC CAT TGT ACC AT | HPV-42, 18, 45, CAND85 | CACCTGAGTGGATACA AAGAC |
| HPV-21, 93 | 39, 40 | BTCA AAC GCC CAT TGA ACC AT | HPV-40, 7 | CACCGGAATGGATAGC TAAAC |
| HPV-24, 63, RTRX7, 8, 18, 70 | 41, 42 | BTCA AAT GCC CAT TGT ACC AT | HPV-39, 70 | CGCCAGAATGGATACA ACGAT |
| HPV-47, 25, 19, 45, 30 | 43, 44 | BTCA AAT GCC CAT TGA ACC AT | HPV-26, 69 | CACCAGAATGGATAGT ACGAC |
| HPV-5 | 45, 46 | BTGA AAT GCC CAT TGG ACC AT | HPV-51, 30 | CACCAGAATGGATTAC ACGAC |
| HPV-26 | 47, 48 | BTCG AAC GCC CAT TGC AC | HPV-82 | CACCAGAATGGATTAC AAGAC |
| HPV-29, 52, 69, 44, 55, 32, 42, 91 | 49, 50 | BTCA TAT GCC CAT TGC ACC AT | HPV-53, 56, 66 | CACCAGAATGGATACA AAGAC |
| HPV-40, 7, 13, 11, 6A, 6B | 51, 52 | BTCA AT GCC CAC TGC ACC | HPV-67, 31 | CACCAGAATGGATAGA AAGAC |
| HPV-14D, 56 | 53, 54 | BTCA AAT GCC CAC TGC ACC | HPV-16, 35 | CGCCAGAATGGATACA AAGAC |
| HPV-77, 50, 4 | 55, 56 | BTCG TAT GCC CAC TGT ACC AT | HPV-52 | GGTACAACCCCAGAAT GGAT |
| HPV-65, 1A, 95 | 57, 58 | BTCA TAA GCC CAC TGA ACC AT | HPV-54 | GGTACAACCCCAGGAT GG |
| HPV-CAND85, 59, 73 | 59, 60 | GTCA AAC GCC CAT TGT ATC AT | HPV-1A | GGTACAACTTTGGAGT GGAT |
| HPV-92, 94 | 61, 62 | BTCA TAT GCC CAC TGT ATC AT | HPV-4, 65, 95, 63, 38 | GGACAAACACCTGATT GGAT |
| HPV-17, 60, 9 | 63, 64 | BTCA TAA GCA AAT TGT ATC AT | HPV-14D, 20, 21, 36, 5, 47, 12, RTRX7, 8 | GGTCCATATCCTGATTG GAT |

-continued

| HPV types | SEQ ID NO (F, R) | Sequence (Forward) | HPV types (Reverse) | Sequence |
|---|---|---|---|---|
| HPV-22, 75, 76, 49, 38, 58 | 65, 66 | BTCA TAA GCC CAT TGT ATC AT | HPV-60 | GGACCGTTTCCAGATTG GTT |
| HPV-23 | 67, 68 | BATC ATA AGC CCA TTG TAT CAT T | HPV-80, 15, 9, 22, 23, 96, 93, 24 17, 37, 48, 50 | GGAGAGTATCCTGAGT GGAT |
| HPV-34, 66 | 69, 70 | BTCA AAT GCC CAC TGT ACC AT | HPV-25, 19, 92 | GGCTCATATCCAGATTG GAT |
| HPV-33, 86, 84, 72, 61, 89 | 71, 72 | BTCA TAT GCC CAC TGT ACC AT | HPV-75, 76, 49 | GGAACTATCCTGATTG GAT |
| HPV-83, 87 | 73 | BTCA TAC GCC CAC TGC ACA | — | —. |

10. The method of claim 7 further comprising the step of contacting the probes with a positive control hybridizing to each probe.

11. The array of claim 3 further comprising probes specific for HPV genotypes 1, 2, 3, 4, 5, 8, 9, 10, 12, 13, 14, 15. 17, 19, 20, 21, 22, 23, 24, 25, 25, 27, 28, 30, 32, 36, 37, 38, 41, 47, 48, 49, 50, 52, 53, 54, 55, 57, 59, 60, 61, 63, 65, 67, 70, 71, 72, 73, 75, 76, 77, 80, 81, 82, 83, 84. CAND85, 86, 87, 89, 90, 91, 92, 93 94, 95, 96, and RTRX7.

* * * * *

UNITED STATES PATENT AND TRADEMARK OFFICE
CERTIFICATE OF CORRECTION

PATENT NO. : 7,875,428 B2  
APPLICATION NO. : 11/707832  
DATED : January 25, 2011  
INVENTOR(S) : Nader Pourmand et al.

It is certified that error appears in the above-identified patent and that said Letters Patent is hereby corrected as shown below:

In the Claims

Column 161, line 41, claim 3, the line that reads:
"genotypes, 33, 35, 39, 45, 51, 52, 56, 58, -69, 6, 11, 34, 40, and" should read --genotypes 33, 35, 39, 45, 51, 52, 56, 58, 69, 6, 11, 34, 40, and--

Column 162, line 19, claim 4, "target." should read --target,--

Column 162, line 29, claim 7, before the word contacting add --a)--

Column 162, line 40, claim 8, the line that reads:
"-39, -45, -51, -56, -58, -66, -69 and HPV-6, -11, -34, -40, -42," should read --39, -45, -51, -52, -56, -58, -66, -69 and HPV-6, -11, -34, -40, -42,--

Column 161, claim 9, under the table heading HPV types, the second occurrence of "HPVa-81, 10" should read --HPVb -81, 10--

Column 163, claim 9, in the line that reads:
"HPV – 40,7,13,11,6A, 6B   51, 52   BTCA AT GCC CAC TGC ACC"
the sequence (forward) should read --BTCA TAT GCC CAC TGC ACC--

Column 163, claim 9, in the line that reads:
"HPV – CAND85, 59, 73   59, 60   GTCA AAC GCC CAT TGT ATC AT"
the sequence (forward) should read --BTCA AAC GCC CAT TGT ATC AT--

Column 164, claim 9, in the line that reads:
"HPV- 84, 86 CACCAGAACTGGATAGTACGAC"
the sequence should read --CACCAGACTGGATAGTACGAC--

Signed and Sealed this  
Thirty-first Day of March, 2015

Michelle K. Lee  
*Director of the United States Patent and Trademark Office*

CERTIFICATE OF CORRECTION (continued)
U.S. Pat. No. 7,875,428 B2

Column 166, claim 9, in the line that reads:
"HPV- 75, 76, 49 GGAACTATCCTGATTGGAT"
the sequence should read --GGAACCTATCCTGATTGGAT--